(12) United States Patent
Cho et al.

(10) Patent No.: US 11,450,813 B2
(45) Date of Patent: Sep. 20, 2022

(54) ORGANIC OPTOELECTRONIC DIODE AND DISPLAY DEVICE

(71) Applicants: SAMSUNG SDI CO., LTD., Yongin-si (KR); SAMSUNG ELECTRONICS CO., LTD., Suwon-si (KR)

(72) Inventors: Pyeongseok Cho, Suwon-si (KR); Dongyeong Kim, Suwon-si (KR); Dong Wan Ryu, Suwon-si (KR); Byoungkwan Lee, Suwon-si (KR); Sung-Hyun Jung, Suwon-si (KR); Dalho Huh, Suwon-si (KR)

(73) Assignees: SAMSUNG SDI CO., LTD., Yongin-si (KR); SAMSUNG ELECTRONICS CO., LTD., Suwon-si (KR)

( * ) Notice: Subject to any disclaimer, the term of this patent is extended or adjusted under 35 U.S.C. 154(b) by 448 days.

(21) Appl. No.: 16/621,834

(22) PCT Filed: Jun. 15, 2018

(86) PCT No.: PCT/KR2018/006793
§ 371 (c)(1),
(2) Date: Dec. 12, 2019

(87) PCT Pub. No.: WO2018/236092
PCT Pub. Date: Dec. 27, 2018

(65) Prior Publication Data
US 2020/0176688 A1    Jun. 4, 2020

(30) Foreign Application Priority Data

Jun. 19, 2017 (KR) .................. 10-2017-0077414

(51) Int. Cl.
*H01L 51/50* (2006.01)
*H01L 51/00* (2006.01)
(Continued)

(52) U.S. Cl.
CPC ........ *H01L 51/0072* (2013.01); *C07D 487/04* (2013.01); *C09K 11/06* (2013.01);
(Continued)

(58) Field of Classification Search
None
See application file for complete search history.

(56) References Cited

U.S. PATENT DOCUMENTS

| 9,293,716 B2 | 3/2016 | Feldman et al. |
| 2011/0279020 A1 | 11/2011 | Inoue et al. |

(Continued)

FOREIGN PATENT DOCUMENTS

| CN | 103140564 B | 11/2015 |
| JP | 2003-133075 | 5/2003 |

(Continued)

OTHER PUBLICATIONS

International Search Report dated Sep. 21, 2018 for PCT/KR2018/006793 filed on Jun. 15, 2018.

*Primary Examiner* — Gregory D Clark
(74) *Attorney, Agent, or Firm* — Lee IP Law, P.C.

(57) ABSTRACT

Provided are an organic optoelectronic diode and a display device, the organic optoelectronic diode including a cathode and an anode facing each other; at least one organic layer disposed between the cathode and the anode, wherein the organic layer includes a composition for an organic optoelectronic device including a first compound for an organic optoelectronic device represented by a combination of Chemical Formula 1 and Chemical Formula 2, and a second compound for an organic optoelectronic device represented by Chemical Formula 3; and a dopant having a maximum emission wavelength of 570 nm to 750 nm. The detailed descriptions of Chemical Formula 1 to Chemical Formula 3 are the same as that defined in the specification.

13 Claims, 1 Drawing Sheet

(51) Int. Cl.
*C07D 487/04* (2006.01)
*C09K 11/06* (2006.01)
*H01L 51/52* (2006.01)
*H01L 51/56* (2006.01)

(52) U.S. Cl.
CPC ...... *H01L 51/0067* (2013.01); *H01L 51/0073* (2013.01); *C09K 2211/1018* (2013.01); *H01L 51/001* (2013.01); *H01L 51/5004* (2013.01); *H01L 51/5016* (2013.01); *H01L 51/5056* (2013.01); *H01L 51/5088* (2013.01); *H01L 51/5206* (2013.01); *H01L 51/5221* (2013.01); *H01L 51/56* (2013.01); *H01L 2251/301* (2013.01); *H01L 2251/308* (2013.01); *H01L 2251/5384* (2013.01); *H01L 2251/552* (2013.01); *H01L 2251/558* (2013.01)

(56) References Cited

U.S. PATENT DOCUMENTS

| | | | |
|---|---|---|---|
| 2015/0041785 A1* | 2/2015 | Sannomiya | H01L 51/5012 257/40 |
| 2017/0069848 A1* | 3/2017 | Zeng | C07D 487/04 |

FOREIGN PATENT DOCUMENTS

| | | |
|---|---|---|
| JP | 5211411 B2 | 3/2013 |
| JP | 5433677 B2 | 3/2014 |
| JP | 2015-106658 A | 6/2015 |
| KR | 10-2010-0057593 A | 5/2010 |
| KR | 10-2014-0096203 A | 8/2014 |
| KR | 10-2014-0113672 A | 9/2014 |
| KR | 10-2014-0143397 A | 12/2014 |
| KR | 10-2015-0003658 A | 1/2015 |
| KR | 10-1502316 B1 | 3/2015 |
| KR | 10-2015-0124902 A | 6/2015 |
| KR | 10-2015-0096593 A | 8/2015 |
| KR | 10-2015-0116776 A | 10/2015 |
| KR | 10-2016-0010373 A | 1/2016 |
| KR | 10-2016-0011522 A | 2/2016 |
| KR | 10-2016-0011582 A | 2/2016 |
| KR | 10-2016-0046076 A | 4/2016 |
| KR | 10-2016-0060569 A | 5/2016 |
| KR | 10-2016-0069934 A | 6/2016 |
| KR | 10-2016-0107406 A | 9/2016 |
| KR | 10-2016-0108798 A | 9/2016 |
| KR | 10-2017-0037276 A | 4/2017 |
| KR | 10-2017-0107919 A | 9/2017 |
| WO | WO 2012-153725 A1 | 11/2012 |
| WO | WO 2013-062075 A1 | 5/2013 |
| WO | WO 2013-146645 A1 | 10/2013 |
| WO | WO 2016-042997 A1 | 3/2016 |
| WO | WO 2016-194604 A1 | 12/2016 |

* cited by examiner

【Figure 1】
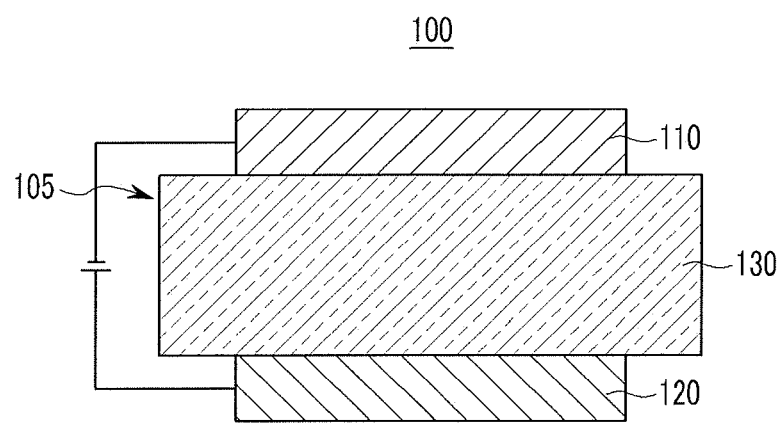
【Figure 2】
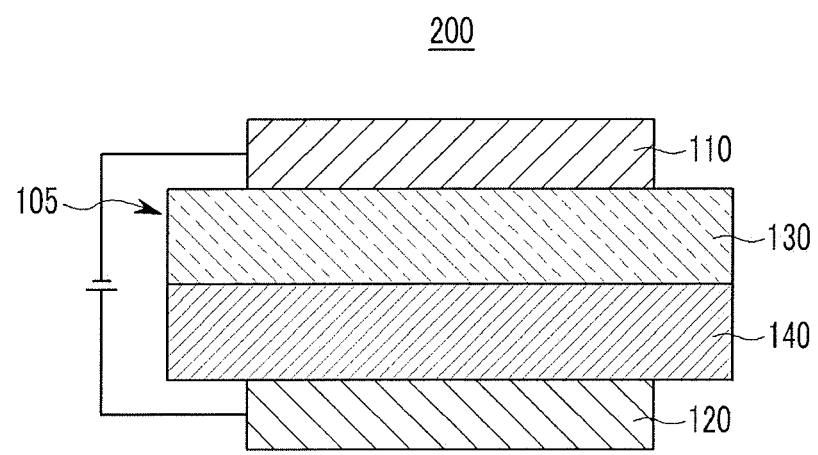

ORGANIC OPTOELECTRONIC DIODE AND DISPLAY DEVICE

CROSS REFERENCE TO RELATED APPLICATIONS

This is the U.S. national phase application based on PCT/KR2018/006793 filed on Jun. 15, 2018, which is based on Korean Patent Application No. 10-2017-0077414, filed Jun. 19, 2017, the entire contents of all of which are hereby incorporated by reference.

TECHNICAL FIELD

An organic optoelectronic device and a display device are disclosed.

BACKGROUND ART

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectronic diode may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode is a device converting electrical energy into light by applying current to an organic light emitting material, and has a structure in which an organic layer is disposed between an anode and a cathode. Herein, the organic layer may include a light emitting layer and optionally an auxiliary layer, and the auxiliary layer may be for example at least one layer selected from a hole injection layer, a hole transport layer, an electron blocking layer, an electron transport layer, an electron injection layer, and a hole blocking layer.

Performance of an organic light emitting diode may be affected by characteristics of the organic layer, and among them, may be mainly affected by characteristics of an organic material of the organic layer.

Particularly, development for an organic material capable of increasing hole and electron mobility and simultaneously increasing electrochemical stability is needed so that the organic light emitting diode may be applied to a large-size flat panel display.

DISCLOSURE

Technical Problem

An embodiment provides an organic optoelectronic device having high efficiency and a long life-span.

Another embodiment provides a display device including the organic optoelectronic device.

Technical Solution

According to an embodiment, an organic optoelectronic device includes an anode and a cathode facing each other and at least one organic layer disposed between the anode and the cathode, wherein the organic layer includes a composition for an organic optoelectronic device including a first compound for an organic optoelectronic device represented by a combination of Chemical Formula 1 and Chemical Formula 2 and a second compound for an organic optoelectronic device represented by Chemical Formula 3; and a dopant having a maximum emission wavelength of 570 to 750 nm.

[Chemical Formula 1]

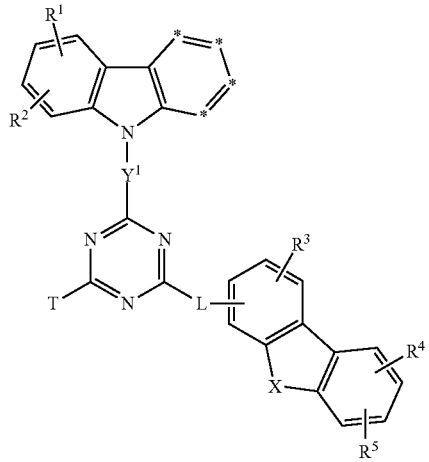

[Chemical Formula 2]

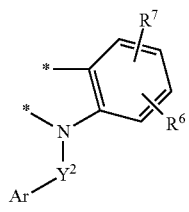

[Chemical Formula 3]

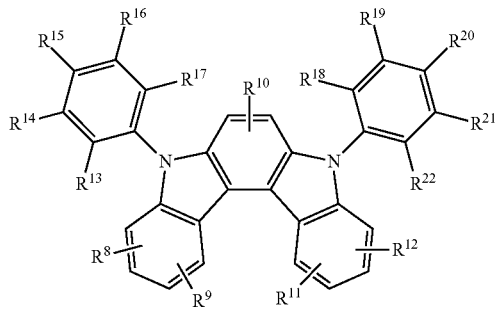

In Chemical Formula 1 to Chemical Formula 3,

X is O or S,

T is a substituted or unsubstituted C6 to C18 aryl group, a substituted or unsubstituted dibenzofuranyl group, or a substituted or unsubstituted dibenzothiophenyl group, Ar is a substituted or unsubstituted C6 to C30 aryl group, L, $Y^1$, and $Y^2$ are independently a single bond, or a substituted or unsubstituted C6 to C20 arylene group, adjacent two *'s of Chemical Formula 1 are linked to *'s of Chemical Formula 2, in Chemical Formula 1, *'s that are not linked to *'s of Chemical Formula 2 are independently $CR^a$, $R^a$ and $R^1$ to $R^{12}$ are independently hydrogen, deuterium, a cyano group, a substituted or unsubstituted C1 to C20 alkyl group, or a substituted or unsubstituted C6 to C18 aryl group, $R^{13}$ to $R^{22}$ are independently hydrogen, deuterium, a cyano group, an amino group, a substituted or unsubstituted C1 to C20 alkyl group, a substituted or unsubstituted C2 to C20 alkenyl group, a substituted or unsubstituted C6 to C18 aryl group, or a substituted or unsubstituted carbazolyl group, $R^{13}$ to $R^{22}$ are independently present or adjacent groups thereof are linked to each other to form a substituted or unsubstituted aromatic ring or a substituted or unsubstituted heteroaromatic ring, and when $R^{13}$ to $R^{22}$ are independently present, at least one of $R^{13}$ to $R^{22}$ is a substituted or unsubstituted C6 to C18 aryl group, or a substituted or unsubstituted carbazolyl group.

According to another embodiment, a display device including the organic optoelectronic device is provided.

Advantageous Effects

An organic optoelectronic device having high efficiency and a long life-span may be realized.

DESCRIPTION OF THE DRAWINGS

FIGS. 1 and 2 are cross-sectional views showing organic light emitting diodes according to embodiments.

DESCRIPTION OF SYMBOLS

100, 200: organic light emitting diode
105: organic layer
110: cathode
120: anode
130: light emitting layer
140: hole auxiliary layer

BEST MODE

Hereinafter, embodiments of the present invention are described in detail. However, these embodiments are exemplary, the present invention is not limited thereto and the present invention is defined by the scope of claims.

In the present specification, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C2 to C30 heteroaryl group, a C1 to C20 alkoxy group, a C1 to C10 trifluoroalkyl group, a cyano group, or a combination thereof.

In one example of the present invention, "substituted" refers to replacement of at least one hydrogen of a substituent or a compound by deuterium, a cyano group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, or a C2 to C30 heteroaryl group. In addition, in a specific example of the present invention, "substituted" refers to replacement of at least one hydrogen of a substituent or a compound by deuterium, a cyano group, a C1 to C20 alkyl group, a C6 to C30 aryl group, or C2 to C30 heteroaryl group. In addition, in a specific example of the present invention, "substituted" refers to replacement of at least one hydrogen of a substituent or a compound by deuterium, a cyano group, a C1 to C5 alkyl group, a C6 to C18 aryl group, a dibenzofuranyl group, or a dibenzothiophenyl group. In addition, in a specific example of the present invention, "substituted" refers to replacement of at least one hydrogen of a substituent or a compound by deuterium, a cyano group, a C1 to C5 alkyl group, a C6 to C18 aryl group, a dibenzofuranyl group, or a dibenzothiophenyl group. In addition, in a specific example of the present invention, "substituted" refers to replacement of at least one hydrogen of a substituent or a compound by deuterium, a cyano group, a methyl group, an ethyl group, a propanyl group, a butyl group, a phenyl group, a biphenyl group, a terphenyl group, a naphthyl group, a triphenyl group, a fluorenyl group, a dibenzofuranyl group, or dibenzothiophenyl group.

In the present specification when a definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have one to four carbon atoms in the alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, or two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, "a heterocyclic group" is a generic concept of a heteroaryl group, and may include at least one heteroatom selected from N, O, S, P, and Si instead of carbon (C) in a cyclic compound such as an aryl group, a cycloalkyl group, a fused ring thereof, or a combination thereof. When the heterocyclic group is a fused ring, the entire ring or each ring of the heterocyclic group may include one or more heteroatoms.

For example, "a heteroaryl group" may refer to an aryl group including at least one heteroatom selected from N, O, S, P, and Si. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heterocyclic group may be a pyridinyl group, a pyrimidinyl group, a pyrazinyl group, a pyridazinyl group, a triazinyl group, a quinolinyl group, an isoquinolinyl group, a quinazolinyl group, and the like.

More specifically, the substituted or unsubstituted C6 to C30 aryl group and/or the substituted or unsubstituted C2 to C30 heterocyclic group may be a substituted or unsubstituted phenyl group, a substituted or unsubstituted naphthyl group, a substituted or unsubstituted anthracenyl group, a substituted or unsubstituted phenanthrenyl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-terphenyl group, a substituted or unsubstituted chrysenyl group, a substituted or unsubstituted triphenylene group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted benzoquinolinyl group, a substituted or unsubstituted benzoisoquinolinyl group, a substituted or unsubstituted benzoquinazolinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied and that a hole formed in the anode may be easily injected into the light emitting layer and transported in the light emitting layer due to conductive characteristics according to a highest occupied molecular orbital (HOMO) level.

In addition, electron characteristics refer to an ability to accept an electron when an electric field is applied and that electron formed in the cathode may be easily injected into the light emitting layer and transported in the light emitting layer due to conductive characteristics according to a lowest unoccupied molecular orbital (LUMO) level.

Hereinafter, an organic light emitting diode as one example of an organic optoelectronic device according to an embodiment is described referring to drawings.

FIGS. 1 and 2 are cross-sectional views of each organic light emitting diode according to an embodiment.

Referring to FIG. 1, an organic light emitting diode 100 according to an embodiment includes an anode 120 and a cathode 110 facing each other and an organic layer 105 disposed between the anode 120 and cathode 110.

The organic layer according to an embodiment of the present invention includes a composition for an organic optoelectronic device including a first compound for an organic optoelectronic device represented by a combination of Chemical Formula 1 and Chemical Formula 2 and a second compound for an organic optoelectronic device represented by Chemical Formula 3; and a dopant having a maximum emission wavelength of 600 nm to 650 nm.

[Chemical Formula 1]

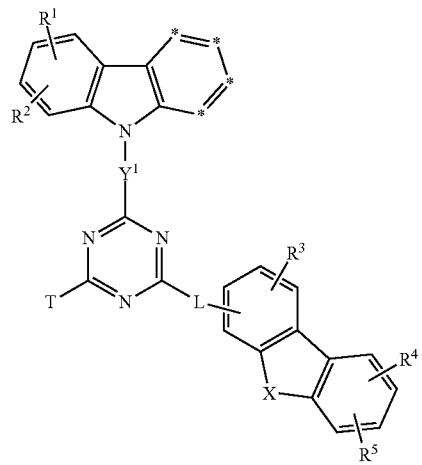

[Chemical Formula 2]

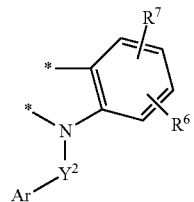

[Chemical Formula 3]

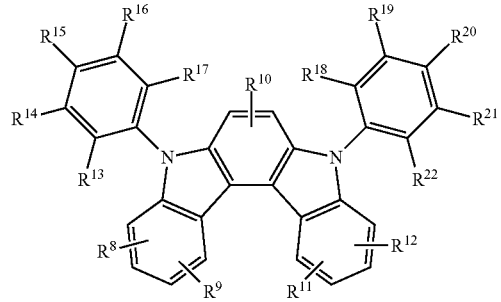

In Chemical Formula 1 to Chemical Formula 3,

X is O or S,

T is a substituted or unsubstituted C6 to C18 aryl group, a substituted or unsubstituted dibenzofuranyl group, or a substituted or unsubstituted dibenzothiophenyl group, Ar is a substituted or unsubstituted C6 to C30 aryl group, L, $Y^1$, and $Y^2$ are independently a single bond, or a substituted or unsubstituted C6 to C20 arylene group, adjacent two *'s of Chemical Formula 1 are linked to *'s of Chemical Formula 2, in Chemical Formula 1, *'s that are not linked to *'s of Chemical Formula 2 are independently $CR^a$, $R^a$ and $R^1$ to $R^{12}$ are independently hydrogen, deuterium, a cyano group, a substituted or unsubstituted C1 to C20 alkyl group, or a substituted or unsubstituted C6 to C18 aryl group, $R^{13}$ to $R^{22}$ are independently hydrogen, deuterium, a cyano group, an amino group, a substituted or unsubstituted C1 to C20 alkyl group, a substituted or unsubstituted C2 to C20 alkenyl group, a substituted or unsubstituted C6 to C18 aryl group, or a substituted or unsubstituted carbazolyl group, $R^{13}$ to $R^{22}$ are independently present or adjacent groups thereof are linked to each other to form a substituted or unsubstituted aromatic ring or a substituted or unsubstituted heteroaromatic ring, when $R^{13}$ to $R^{22}$ are independently present, at least one of $R^{13}$ to $R^{22}$ is a substituted or unsubstituted C6 to C18 aryl group, or a substituted or unsubstituted carbazolyl group.

In particular, the second compound for the organic optoelectronic device is desirably a compound that exhibits current density of 1500 mA/cm$^2$ to 2500 mA/cm$^2$ measured at a voltage of 7 V in the following HOD (Hole Only Device) device.

HOD device: ITO/Compound C (500 Å)/second compound for an organic optoelectronic device of the present invention (400 Å)/Al (1200 Å)

Compound C: N-(biphenyl-4-yl)-9,9-dimethyl-N-(4-(9-phenyl-9H-carbazol-3-yl)phenyl)-9H-fluoren-2-amine The organic optoelectronic device of the present invention includes a phosphorescent dopant having a maximum emission wavelength of 570 nm to 750 nm. That is, it includes a phosphorescent dopant having a maximum emission wavelength out of the green region. For example, the maximum emission wavelength may be 570 nm to 750 nm that is a wavelength of a reddish region, and may be 570 nm to 720 nm, 580 nm to 700 nm, 590 nm to 700 nm, or 600 nm to 650 nm.

When the maximum emission wavelength of the mixture of the first compound for the organic optoelectronic device and the second compound for the organic optoelectronic device is 450 nm to 550 nm, long life-span characteristics of an organic optoelectronic device that emits light in the red region and includes a phosphorescent dopant having a maximum emission wavelength of 570 nm to 750 nm may be included may be ensured, as in the present invention. In order that the maximum emission wavelength of the mixture of the first compound for the organic optoelectronic device and the second compound for the organic optoelectronic device is 450 nm to 550 nm, a difference a LUMO energy level of the first compound for the organic optoelectronic device and a HOMO energy level of the second compound for the first compound for the organic optoelectronic device of an organic optoelectronic device should be 2.30 eV to 3.00 eV.

On the other hand, in the present specification, HOD is an organic light emitting diode manufactured to include a two-layer organic thin layer, and the specific structure is as follows.

ITO/Compound C (500 Å)/second compound for an organic optoelectronic device (400 Å)/Al (1200 Å)

Compound C: N-(biphenyl-4-yl)-9,9-dimethyl-N-(4-(9-phenyl-9H-carbazol-3-yl)phenyl)-9H-fluoren-2-amine In a device configured as HOD in the present specification, a current density measured at a voltage of 7 V is obtained as a calculation value by measuring a current flowing a unit device with a current-voltage meter (Keithley 2400), while a voltage is increased from −6 V to 8 V with a respect to an organic light emitting diode including the second compound for the organic optoelectronic device in one organic thin layer as aforementioned and then, dividing the current at 7 V by an area.

In the HOD device, the current density measured at a voltage of 7 V may be specifically 2000 mA/cm$^2$ to 2500 mA/cm$^2$ and more specifically, 2000 mA/cm$^2$ to 2300 mA/cm$^2$.

In other words, when the HOD device has the current density, since the second compound for the organic optoelectronic device according to the present invention along with the first compound for the organic optoelectronic device as a host improves hole transportation capability in a red phosphorescence device, the HOD device may exhibit excellent life-span and luminous efficiency.

In an example embodiment of the present invention, the first compound for the organic optoelectronic device included in the composition for the organic optoelectronic device may have a LUMO energy level ranging from −3.0 eV to −3.3 eV, and the second compound for the organic optoelectronic device may have a HOMO energy level ranging from −5.5 eV to −6.0 eV. Herein, a maximum emission wavelength of the mixture of the first compound for the organic optoelectronic device and the second compound for the organic optoelectronic device may be 450 nm to 550 nm as described above. In addition, a difference between HOMO energy levels of the first compound for the organic optoelectronic device and the second compound for the organic optoelectronic device may be 0.2 eV to 0.5 eV.

In a specific example embodiment of the present invention, a difference between HOMO energy levels of the first compound for the organic optoelectronic device and the second compound for the organic optoelectronic device may be 0.2 eV to 0.4 eV, and desirably 0.2 eV to 0.3 eV.

The energy level is calculated by using a value measured by an Electro chemical analyzer (EpsilonEC & C3 cell stand, WinATech) as a reference, and herein, a working electrode is manufactured by dispersing a measuring material in a solvent, dropping the solution in a carbon electrode to form a film, Ag/AgCl is used as a reference electrode, and Pt is used as a counter electrode. The electrolyte solution is prepared by using 0.1 M tetrabutylammonium perchlorate, and the energy level of the measuring material is calculated by using a measurement value of Ferrocene of −4.8 V as a reference.

In an example embodiment of the present invention, the first compound for the organic optoelectronic device may be represented by one of Chemical Formula 1A, Chemical Formula 1B, Chemical Formula 1C, Chemical Formula 1D, Chemical Formula 1E, and Chemical Formula 1F.

[Chemical Formula 1A]
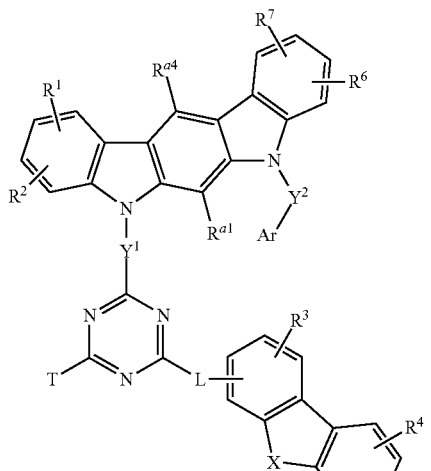
[Chemical Formula 1B]
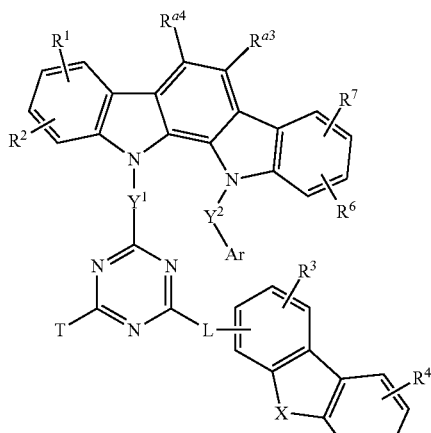
[Chemical Formula 1C]
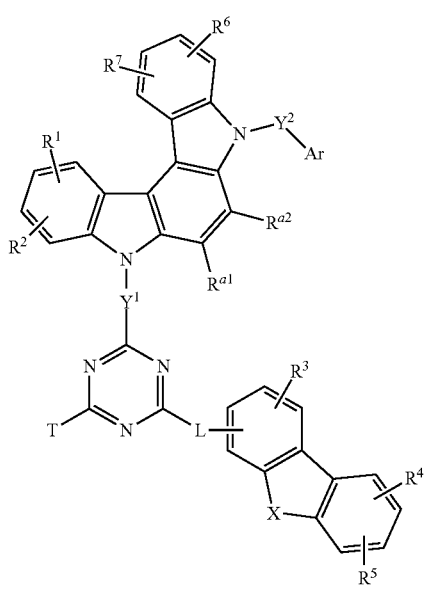
[Chemical Formula 1D]
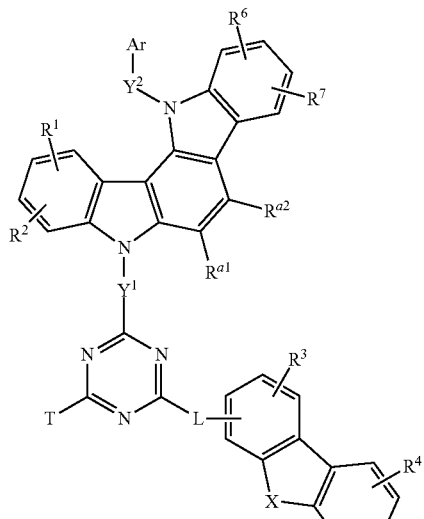
[Chemical Formula 1E]
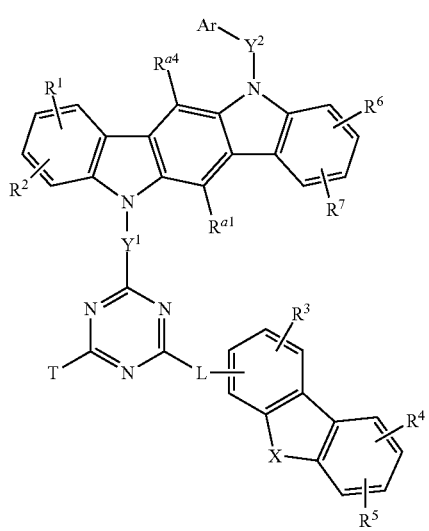
[Chemical Formula 1F]
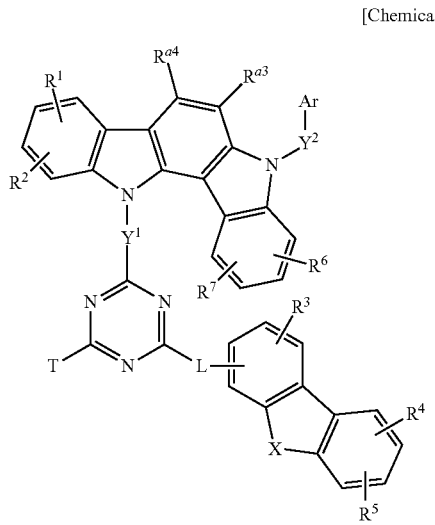

In Chemical Formula 1A, Chemical Formula 1B, Chemical Formula 1C, Chemical Formula 1D, Chemical Formula 1E, and Chemical Formula 1F, X, T, Ar, L, $Y^1$, $Y^2$, and $R^1$ to $R^7$ are the same as described above, and $R^{a1}$ to $R^{a4}$ are the same as $R^1$ to $R^2$.

In a specific example of the present invention, "substituted" of Chemical Formulae 1 and 2 refers to replacement of at least one hydrogen of a substituent or a compound by deuterium, a cyano group, a phenyl group, a biphenyl group, or a naphthyl group.

In a specific example embodiment of the present invention, the first compound for the organic optoelectronic device may be represented by Chemical Formula 1B or Chemical Formula 1C, for example Chemical Formula 1B may be represented by one of Chemical Formula 1B-1 to Chemical Formula 1B-4, and Chemical Formula 1C may be represented by one of Chemical Formula 1C-1 to Chemical Formula 1C-4.

[Chemical Formula 1B-1]

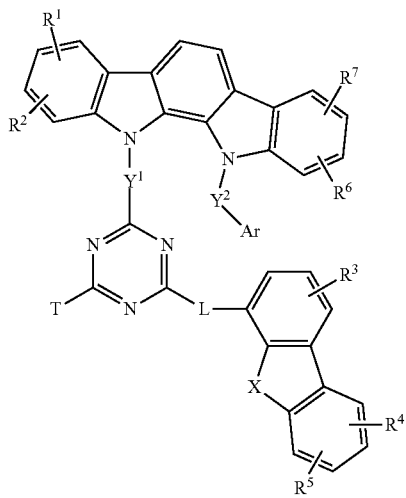

[Chemical Formula 1B-2]

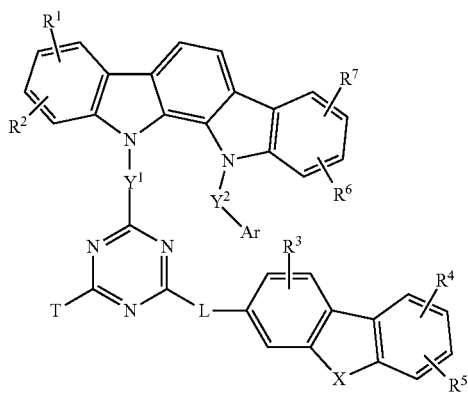

[Chemical Formula 1B-3]

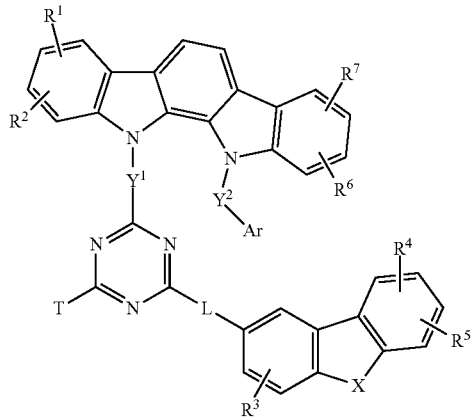

[Chemical Formula 1B-4]

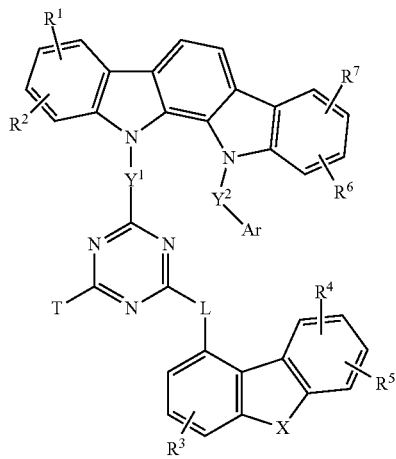

[Chemical Formula 1C-1]

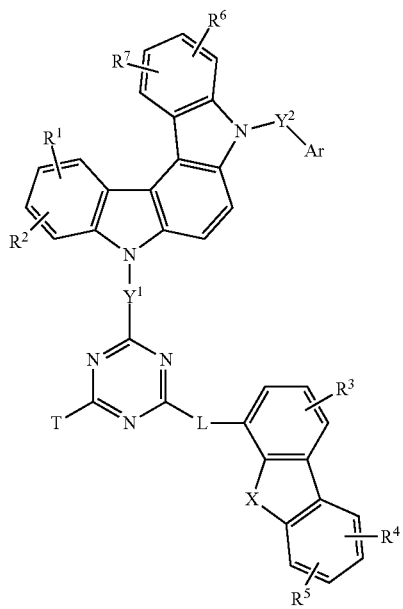

[Chemical Formula 1C-2]

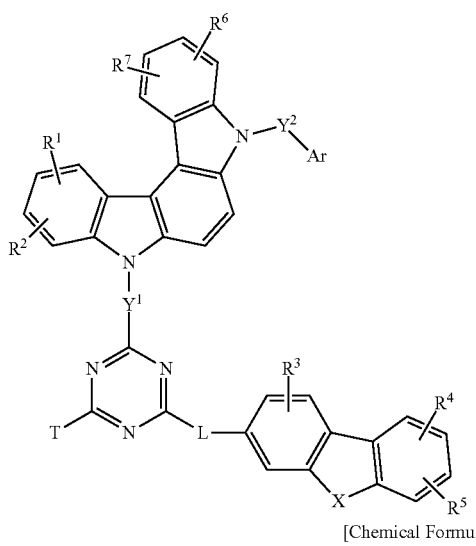

[Chemical Formula 1C-3]

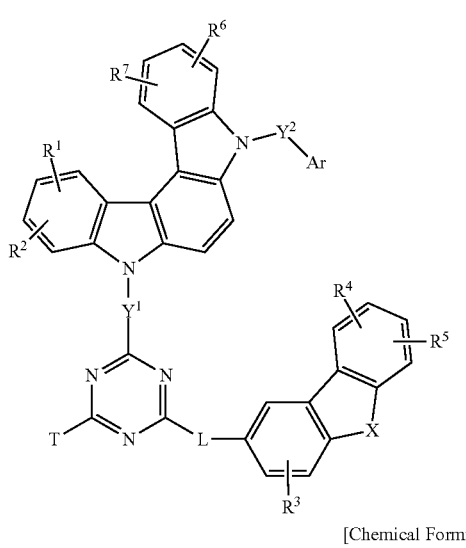

[Chemical Formula 1C-4]

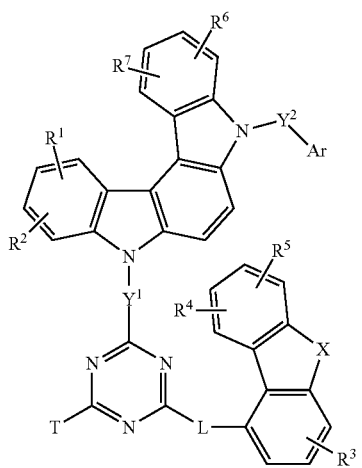

In Chemical Formula 1B-1 to Chemical Formula 1B-4, and Chemical Formula 1C-1 to Chemical Formula 1C-4, X, T, Ar, L, $Y^1$, $Y^2$, and $R^1$ to $R^7$ are the same as described above.

The first compound for the organic optoelectronic device may desirably be represented by one of Chemical Formula 1B-2, Chemical Formula 1B-3, Chemical Formula 1C-2, and Chemical Formula 1C-3, and may more desirably be represented by one of Chemical Formula 1B-2 or Chemical Formula 1C-2.

T of Chemical Formula 1 may be specifically a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, or a substituted or unsubstituted dibenzothiophenyl group, and desirably a substituted or unsubstituted phenyl group, a substituted or unsubstituted biphenyl group, a substituted or unsubstituted naphthyl group, or a substituted or unsubstituted terphenyl group and may be for example selected from substituents of Group I.

[Group I]

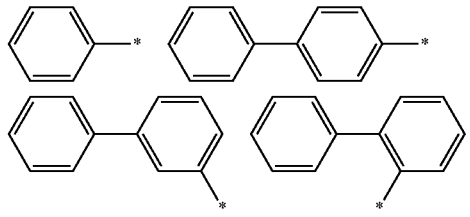
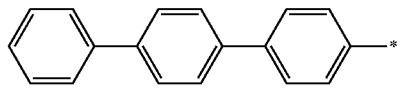
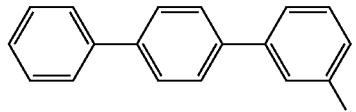
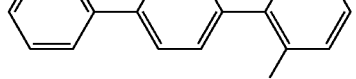
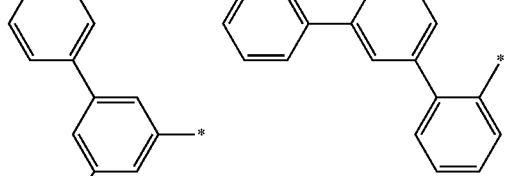
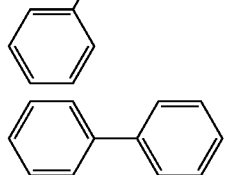
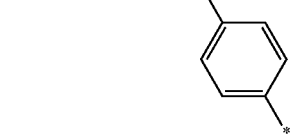

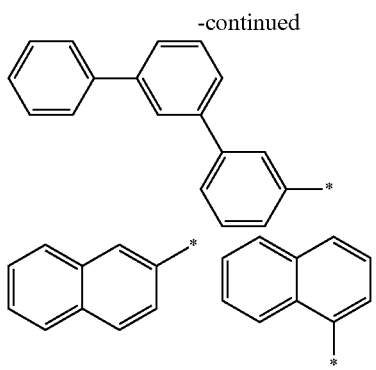

T of Chemical Formula 1 may more desirably be a phenyl group.

Ar of Chemical Formula 2 may desirably be a substituted or unsubstituted phenyl group, a substituted or unsubstituted biphenyl group, a substituted or unsubstituted naphthyl group, or a substituted or unsubstituted terphenyl group, for example substituents of Group I.

Ar of Chemical Formula 2 may more desirably be a phenyl group.

L, $Y^1$, and $Y^2$ of Chemical Formula 1 may be a single bond, a substituted or unsubstituted phenylene group, or a substituted or unsubstituted biphenylene group, and may be for example a single bond or selected from linking groups of Group II.

[Group II]

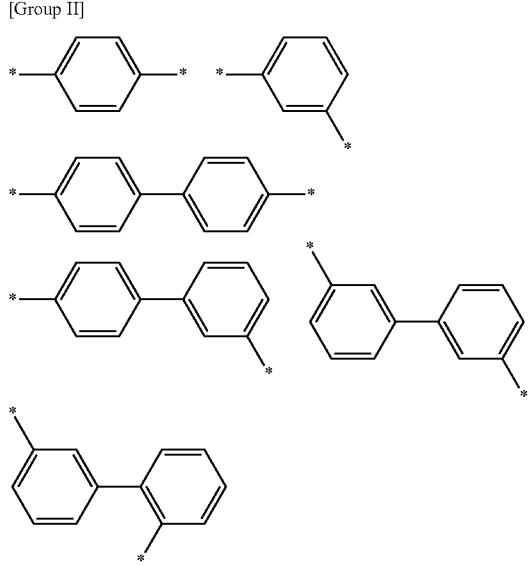

L, $Y^1$, and $Y^2$ of Chemical Formula 1 may more desirably be a single bond.

$R^1$ to $R^7$ of Chemical Formula 1 and Chemical Formula 2 may desirably be hydrogen, or a phenyl group, and $R^1$, $R^2$, $R^6$, and $R^7$ may more desirably be all hydrogen, and $R^3$ and $R^4$ may be hydrogen or a phenyl group.

In an example embodiment of the present invention, the second compound for the organic optoelectronic device may be represented by Chemical Formula 3, and may be represented by one of Chemical Formula 3A-1, Chemical Formula 3A-2, Chemical Formula 3B-1, Chemical Formula 3B-2, Chemical Formula 3B-3, Chemical Formula 3B-4, and Chemical Formula 3B-5 according to $R^{13}$ to $R^{22}$ of Chemical Formula 3.

In a specific example of the present invention, "substituted" of Chemical Formula 3 refers to replacement of at least one hydrogen of a substituent or a compound by deuterium, a cyano group, a phenyl group, a biphenyl group, or a naphthyl group.

Specifically, when each of $R^{13}$ to $R^{22}$ of Chemical Formula 3 is independently present, at least one of $R^{13}$ to $R^{22}$ may be a substituted or unsubstituted C6 to C18 aryl group, or a substituted or unsubstituted carbazolyl group, and may be for example represented by Chemical Formula 3A-1 or Chemical Formula 3A-2 according to a substitution direction of the substituted or unsubstituted C6 to C18 aryl group and the substituted or unsubstituted carbazolyl group.

[Chemical Formula 3A-1]

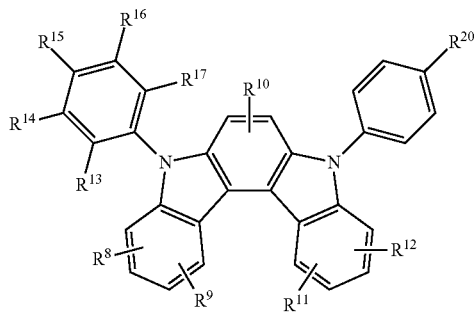

[Chemical Formula 3A-2]

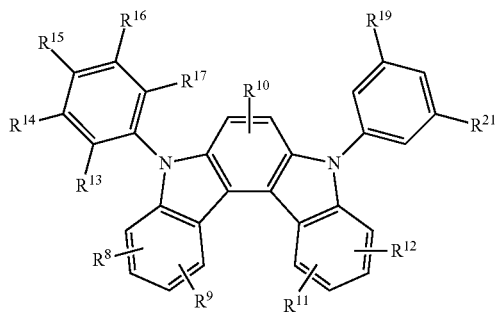

In Chemical Formula 3A-1 and Chemical Formula 3A-2, $R^8$ to $R^{17}$ are independently hydrogen, deuterium, a cyano group, an amino group, a substituted or unsubstituted C1 to C20 alkyl group, a substituted or unsubstituted C2 to C20 alkenyl group, a substituted or unsubstituted C6 to C18 aryl group, or a substituted or unsubstituted carbazolyl group, $R^{13}$ to $R^{17}$ are independently present or adjacent groups thereof are linked to each other to form a substituted or unsubstituted aromatic ring or a substituted or unsubstituted aromatic heteroaromatic ring, and $R^{19}$ to $R^{21}$ is a substituted or unsubstituted C6 to C18 aryl group, or a substituted or unsubstituted carbazolyl group.

$R^8$ to $R^{12}$ of Chemical Formula 3A-1 and Chemical Formula 3A-2 may be hydrogen, or a phenyl group, and may more desirably be all hydrogen.

In addition, $R^{13}$ to $R^{17}$ of Chemical Formula 3A-1 and Chemical Formula 3A-2 may independently be hydrogen, a substituted or unsubstituted phenyl group or a substituted or unsubstituted biphenyl group and adjacent groups of $R^{13}$ to $R^{17}$ are linked to each other to form a substituted or unsubstituted naphthyl group, wherein the substituent may be a phenyl group, a biphenyl group, or a naphthyl group. Further, in an example embodiment of the present invention, $R^{13}$ to $R^{17}$ are all hydrogen, at least one of $R^{14}$ to $R^{16}$ may be a phenyl group or a biphenyl group, and in another example embodiment, $R^{13}$ to and $R^{17}$ are all hydrogen or $R^{13}$, $R^{14}$, $R^{16}$, and $R^{17}$ may all be hydrogen and $R^{15}$ may be a phenyl group.

Further, at least one of $R^{19}$ to $R^{21}$ of Chemical Formula 3A-1 and Chemical Formula 3A-2 may be a substituted or unsubstituted phenyl group, a substituted or unsubstituted biphenyl group, a substituted or unsubstituted naphthyl group, a substituted or unsubstituted terphenyl group, or a substituted or unsubstituted carbazolyl group, and may be for example selected from substituents of Group III.

[Group III]

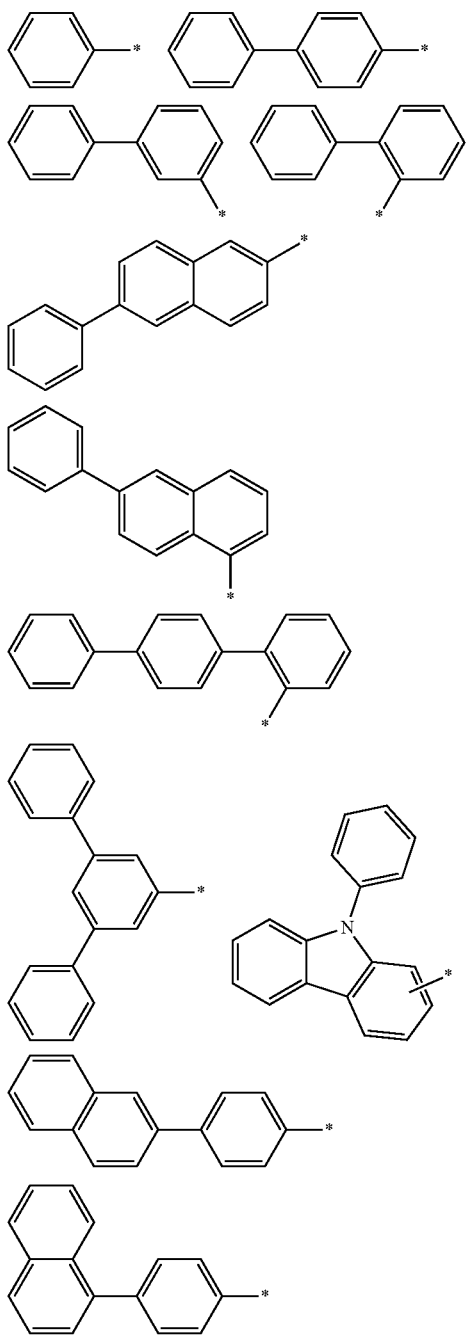

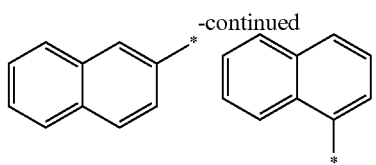

In an example embodiment of the present invention, at least one of $R^{19}$ to $R^{21}$ of Chemical Formula 3A-1 and Chemical Formula 3A-2 may be a phenyl group or a carbazolyl group and $R^{20}$ may be a phenyl group or a carbazolyl group.

Meanwhile, when adjacent groups of $R^{13}$ to $R^{17}$ or $R^{18}$ to $R^{22}$ of Chemical Formula 3 are linked to form a substituted or unsubstituted aromatic ring or a substituted or unsubstituted heteroaromatic ring, a phenyl ring including $R^{13}$ to $R^{17}$ or $R^{18}$ to $R^{22}$ may form a substituted or unsubstituted naphthyl group, a substituted or unsubstituted anthracenyl group, a substituted or unsubstituted triphenylene group, or a substituted or unsubstituted carbazolyl group, and may be for example represented by one of Chemical Formula 3B-1, Chemical Formula 3B-2, Chemical Formula 3B-3, Chemical Formula 3B-4, and Chemical Formula 3B-5.

[Chemical Formula 3B-1]

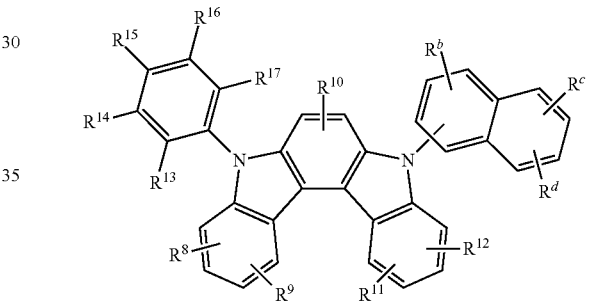

[Chemical Formula 3B-2]

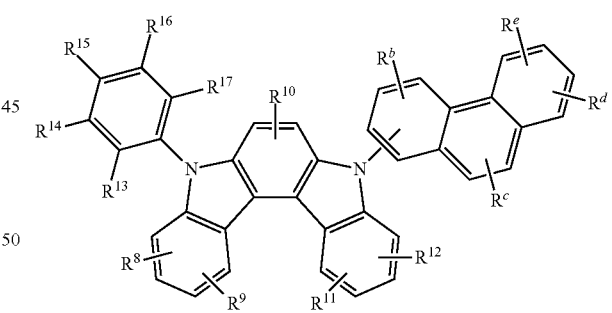

[Chemical Formula 3B-3]

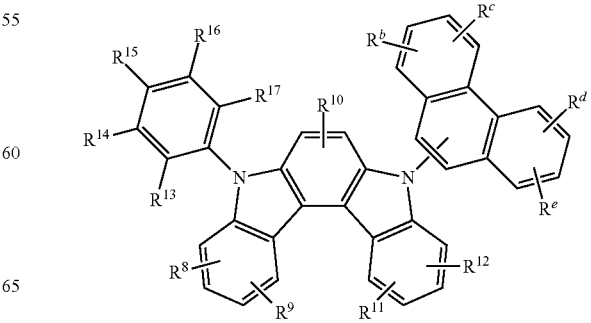

-continued

[Chemical Formula 3B-4]

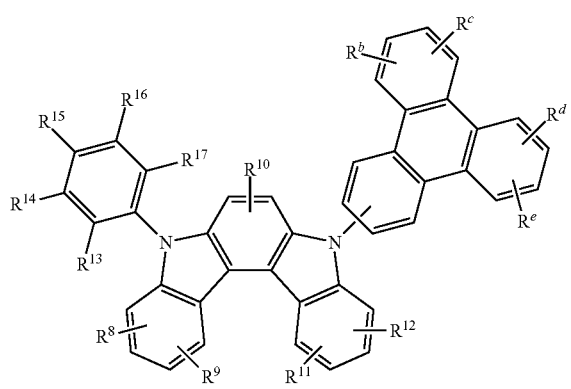

[Chemical Formula 3B-5]

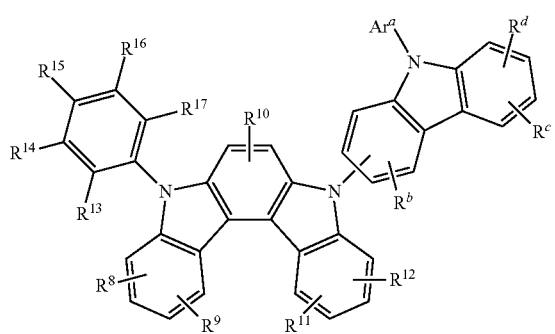

In Chemical Formula 3B-1, Chemical Formula 3B-2, Chemical Formula 3B-3, Chemical Formula 3B-4, and Chemical Formula 3B-5, $R^8$ to $R^{17}$ are the same as described above, $R^b$, $R^c$, $R^d$, and $R^e$ are independently hydrogen, deuterium, a cyano group, a substituted or unsubstituted C1 to C20 alkyl group, or a substituted or unsubstituted C6 to C18 aryl group, and Ara is a substituted or unsubstituted C6 to C18 aryl group.

$R^{13}$ to $R^{17}$ of Chemical Formula 3B-1, Chemical Formula 3B-2, Chemical Formula 3B-3, Chemical Formula 3B-4, and Chemical Formula 3B-5 may independently be hydrogen, a substituted or unsubstituted phenyl group, a substituted or unsubstituted biphenyl group, or a substituted or unsubstituted naphthyl group or adjacent groups thereof may be linked with each other to form a substituted or unsubstituted naphthyl group. Herein, "substituted" refers to substitution with a phenyl group, a biphenyl group, or a naphthyl group.

In a specific example embodiment of the present invention, the second compound for the organic optoelectronic device may be represented by Chemical Formula 3A, and desirably Chemical Formula 3A-1.

Herein, $R^{20}$ of Chemical Formula 3A-1 may be a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, or a substituted or unsubstituted carbazolyl group, and in a more specific example embodiment, it may be a phenyl group, or a carbazolyl group.

The composition for the organic optoelectronic device according to a more specific example embodiment of the present invention may include the first compound for the organic optoelectronic device represented by Chemical Formula 1B-2 or Chemical Formula 1C-2 and the second compound for the organic optoelectronic device represented by Chemical Formula 3A-1. Herein, X of Chemical Formula 1B-2 and Chemical Formula 1C-2 may be O or S, T may be a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, or a substituted or unsubstituted dibenzothiophenyl group, Ar is a substituted or unsubstituted phenyl group, a substituted or unsubstituted biphenyl group, a substituted or unsubstituted naphthyl group, or a substituted or unsubstituted terphenyl group, L, $Y^1$, and $Y^2$ may independently be a single bond, a substituted or unsubstituted phenylene group, or a substituted or unsubstituted biphenylene group, $R^1$ to $R^7$ may independently be hydrogen, a substituted or unsubstituted C1 to C5 alkyl group, or a substituted or unsubstituted phenyl group, $R^8$ to $R^{12}$ of Chemical Formula 3A-1 may be hydrogen, or a substituted or unsubstituted phenyl group, $R^{13}$ to $R^{17}$ may independently be hydrogen, a substituted or unsubstituted phenyl group, or a substituted or unsubstituted biphenyl group, adjacent groups of $R^{13}$ to $R^{17}$ may be linked with each other to form a substituted or unsubstituted naphthyl group, and $R^{20}$ may be a substituted or unsubstituted phenyl group, a substituted or unsubstituted biphenyl group, a substituted or unsubstituted naphthyl group, a substituted or unsubstituted terphenyl group, or a substituted or unsubstituted carbazolyl group.

The compound for the organic optoelectronic device represented by the combination of Chemical Formula 1 and Chemical Formula 2 may be for example selected from compounds of Group 1 and the compound for the organic optoelectronic device represented by Chemical Formula 3 may be for example selected from compounds of Group 2, but are not limited thereto.

[Group 1]

[A-1]

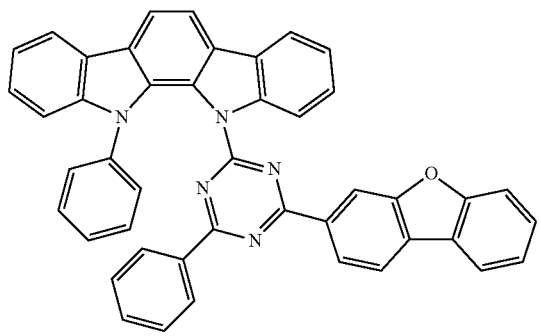

[A-2]

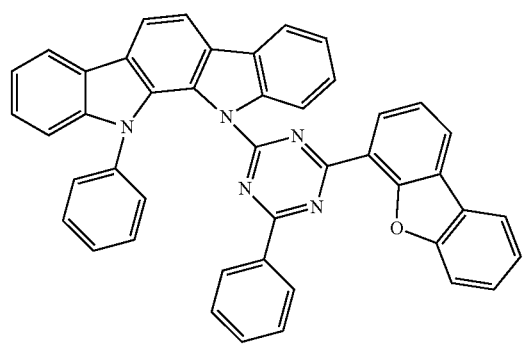

[A-3]
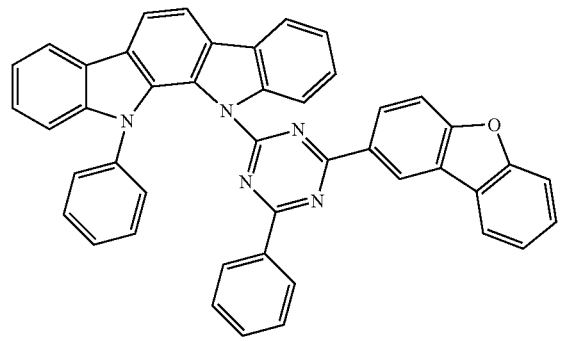
[A-4]
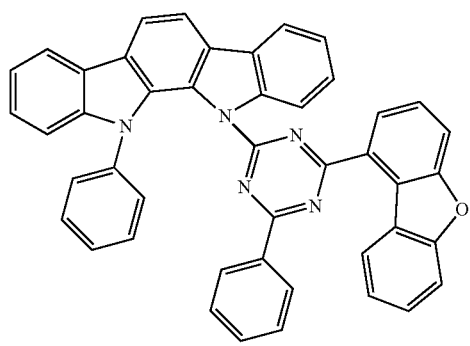
[A-5]
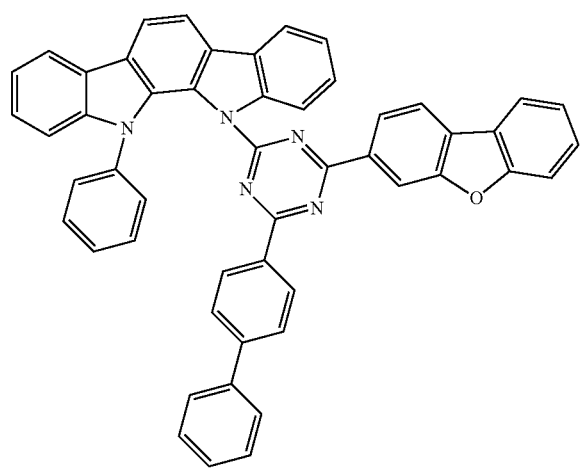
[A-6]
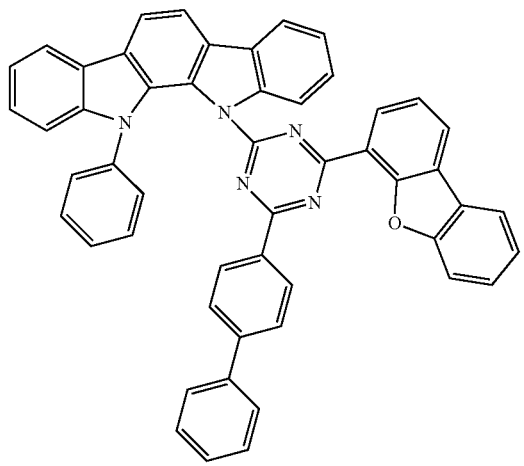
[A-7]
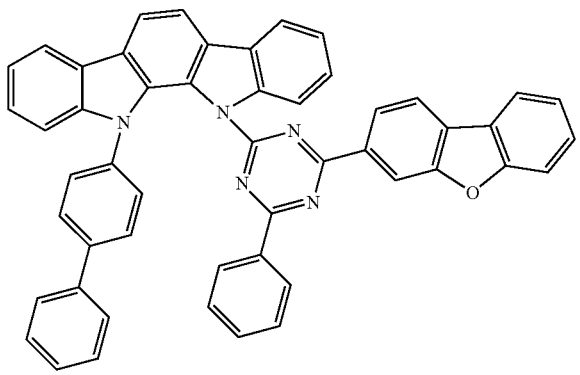
[A-8]
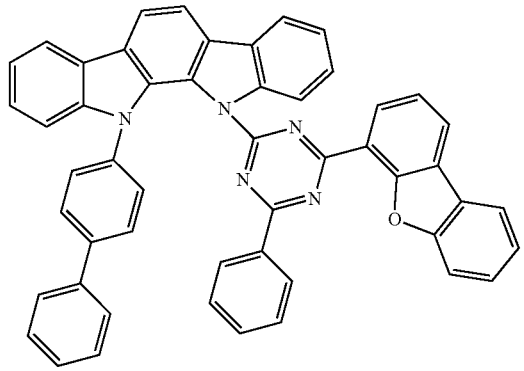

-continued
[A-9]
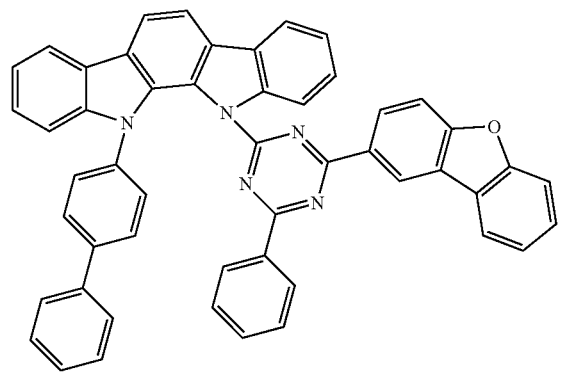
[A-10]
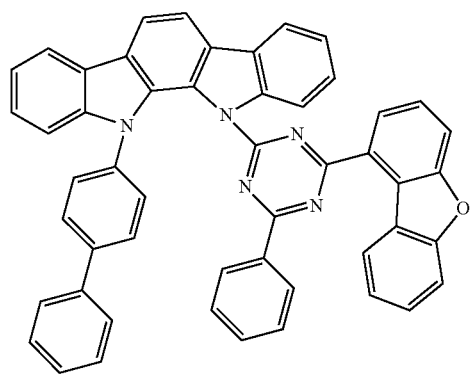
[A-11]
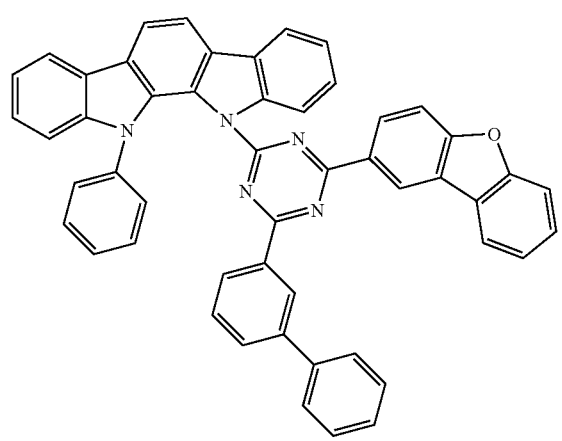
-continued
[A-12]
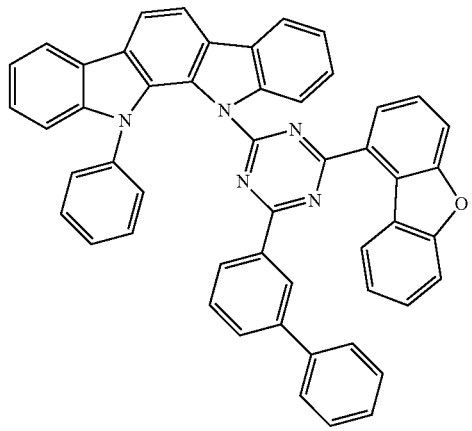
[A-13]
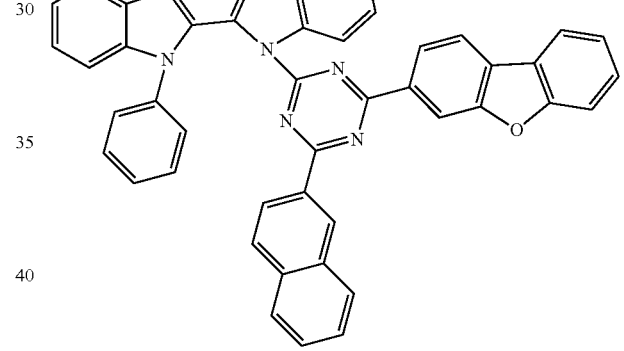
[A-14]
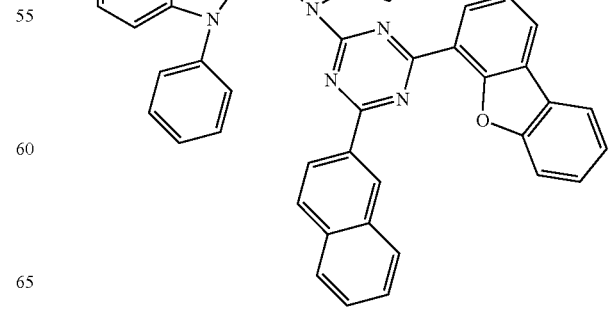

[A-15]
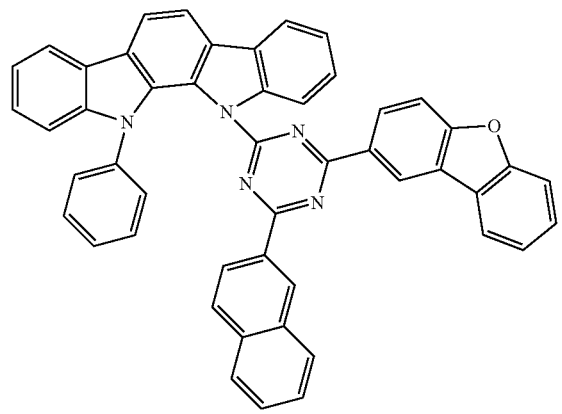
[A-16]
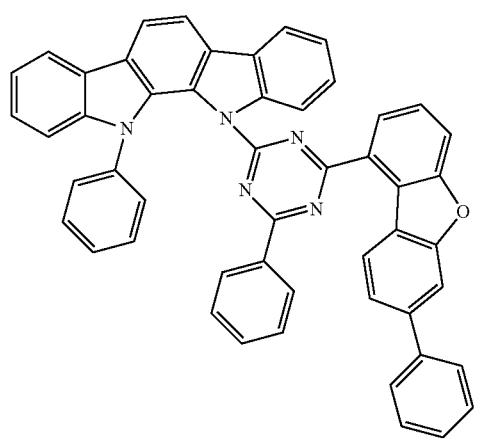
[A-17]
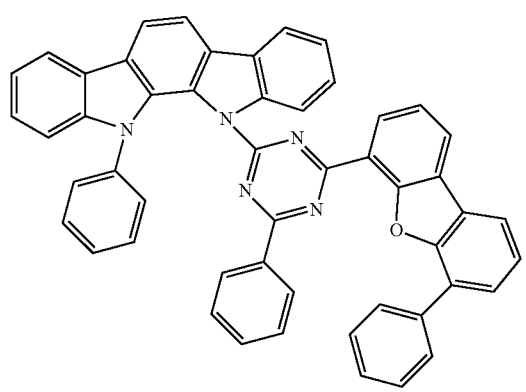
[A-18]
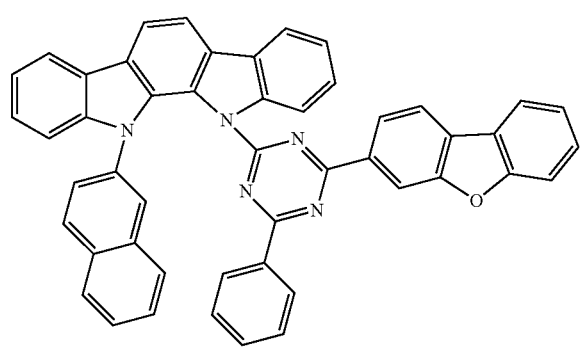
[A-19]
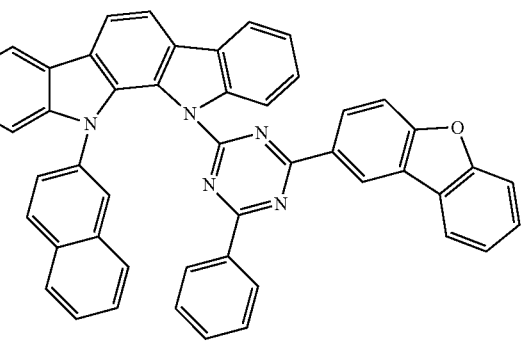
[A-20]
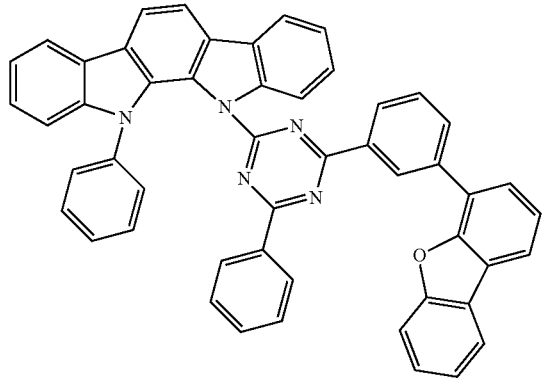
[A-21]
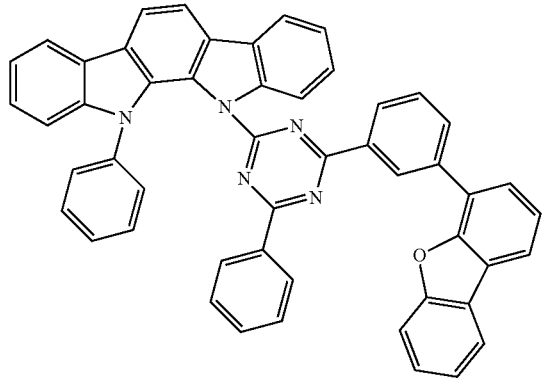
[A-22]
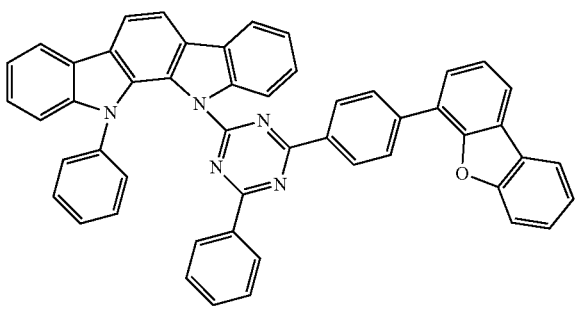

[A-23]
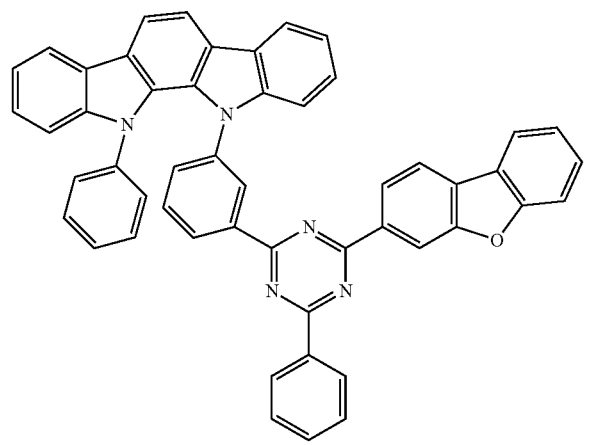
[A-26]
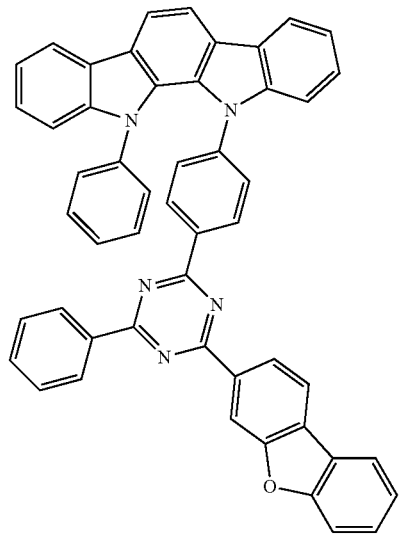
[A-24]
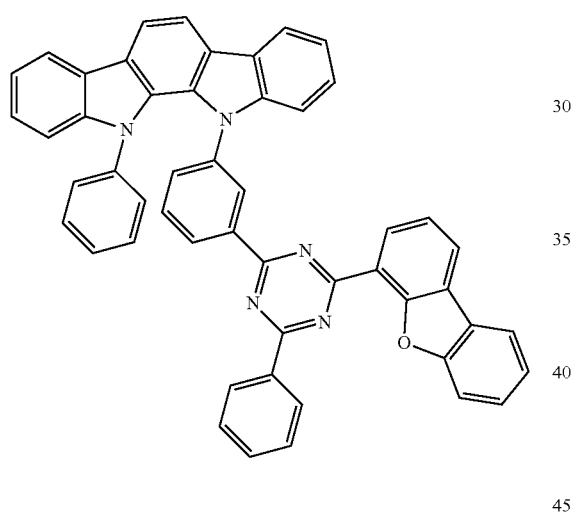
[A-27]
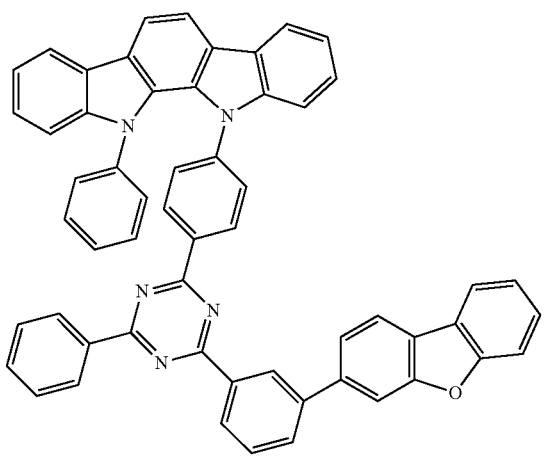
[A-25]
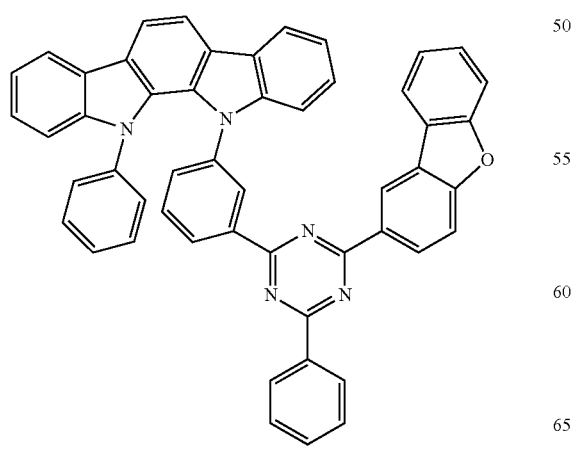
[A-28]
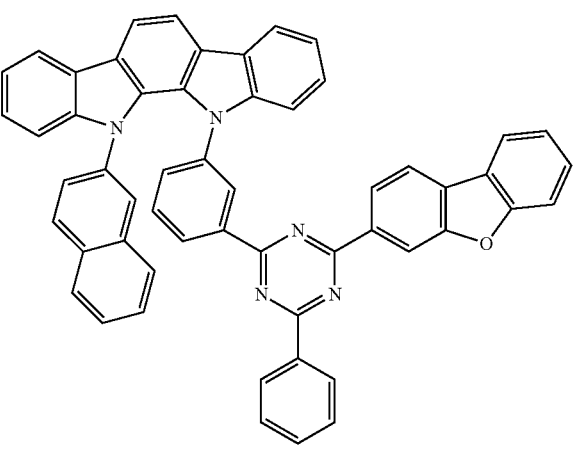

[A-29]
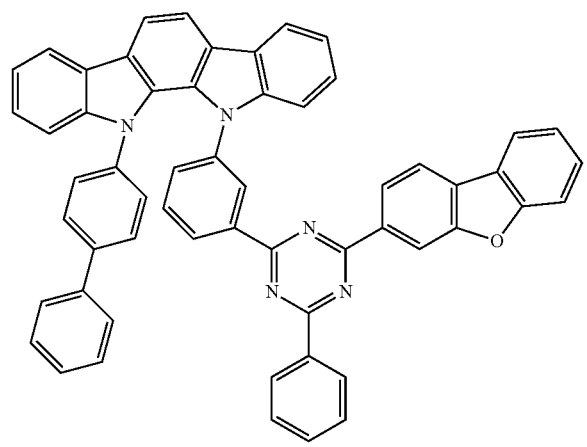
[A-32]
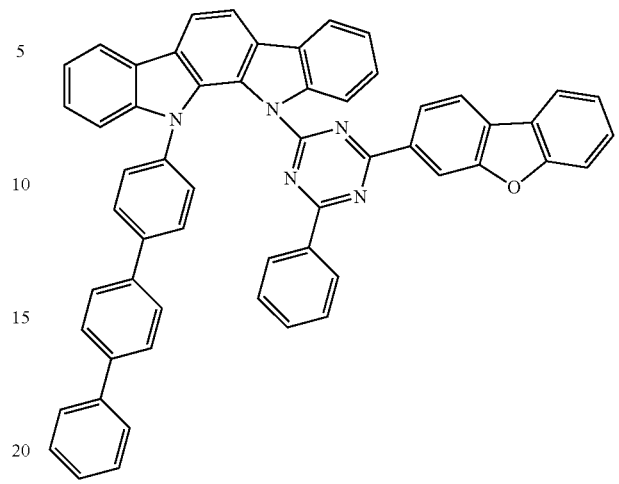
[A-30]
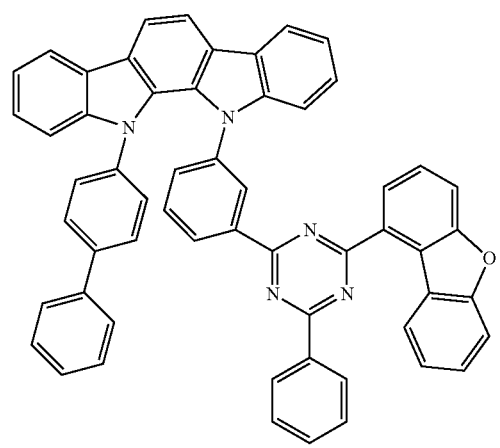
[A-33]
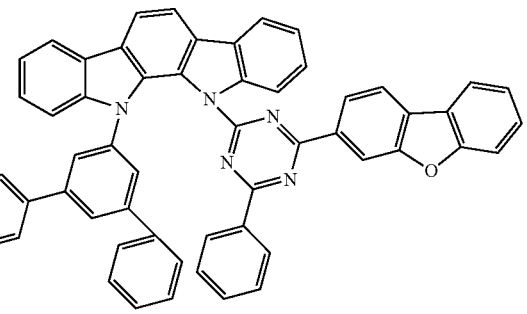
[A-31]
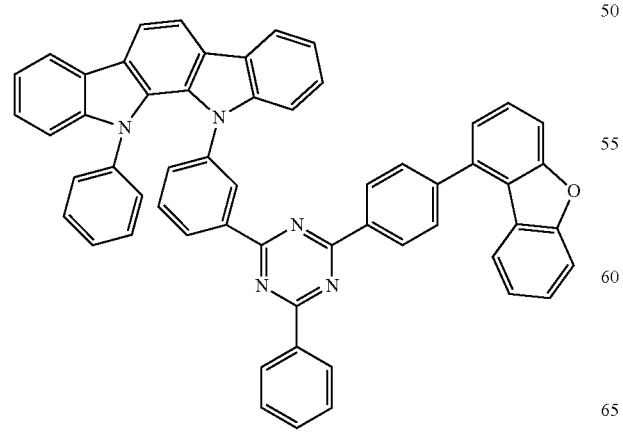
[A-34]
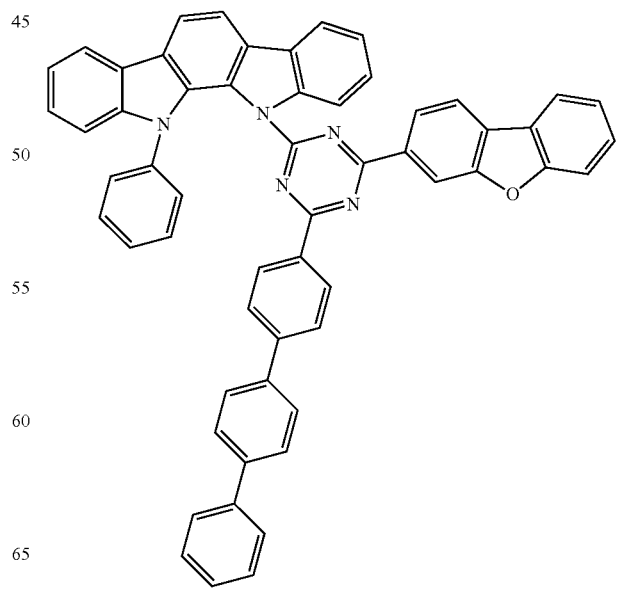

[A-35]
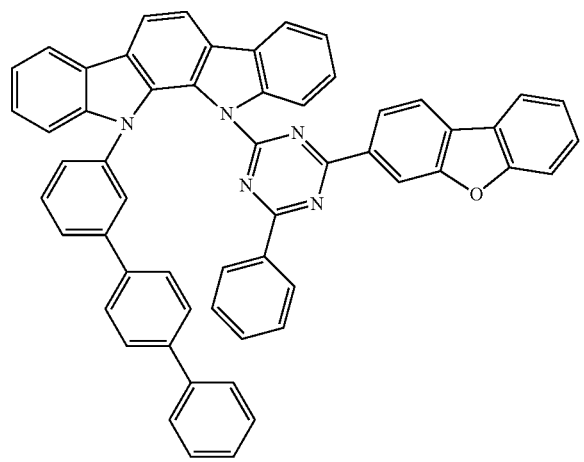
[A-36]
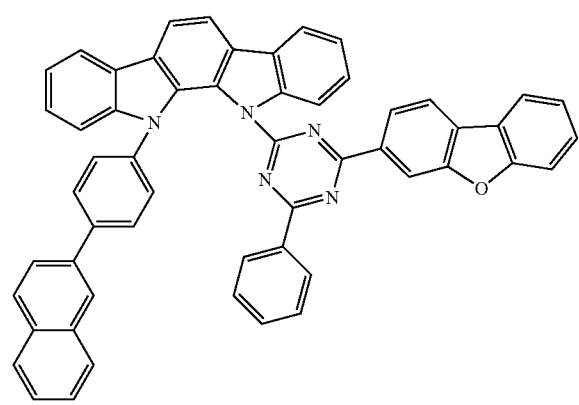
[A-37]
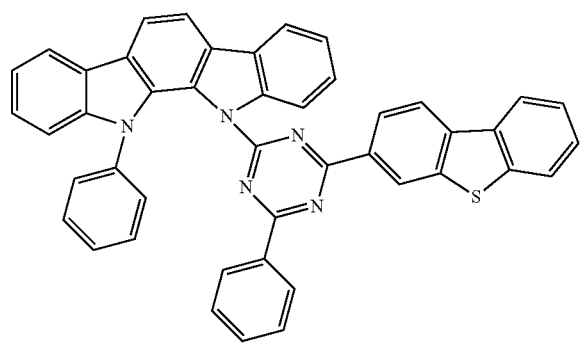
[A-38]
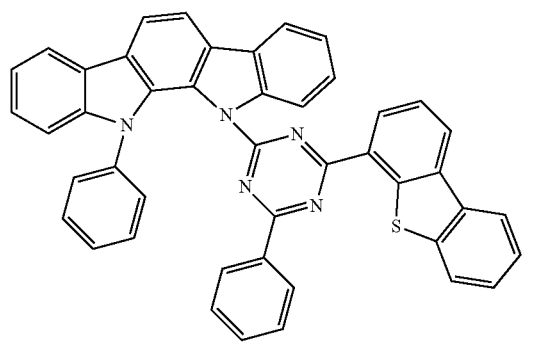
[A-39]
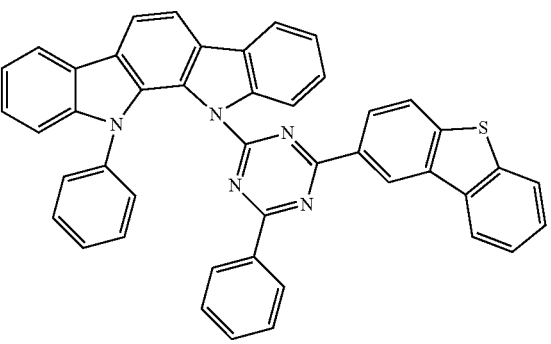
[A-40]
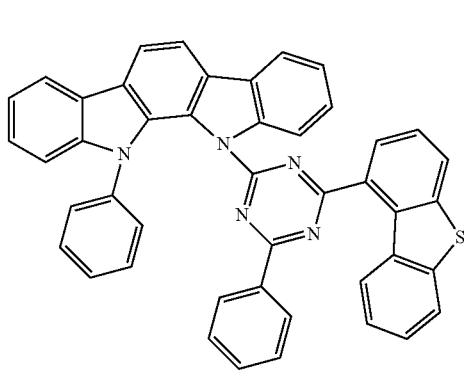
[A-41]
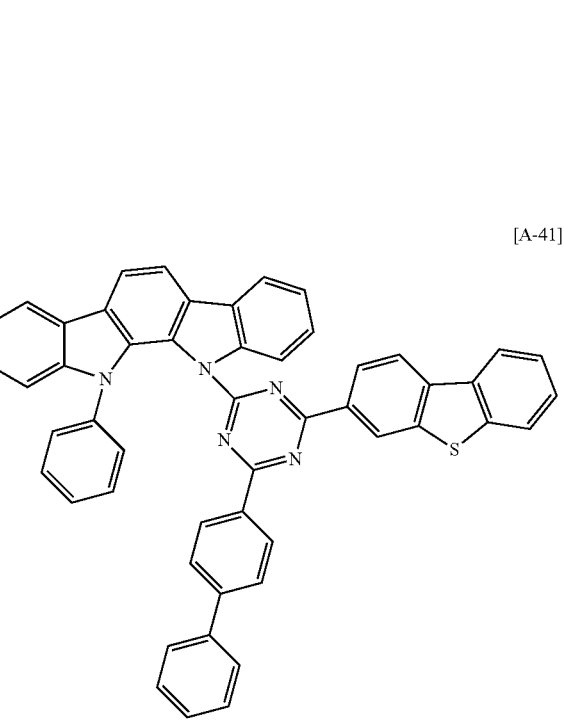

[A-42]
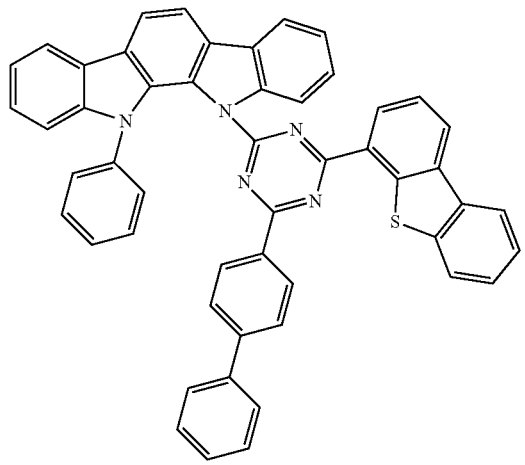
[A-43]
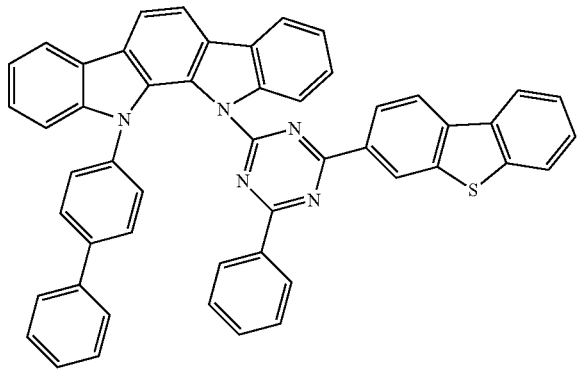
[A-44]
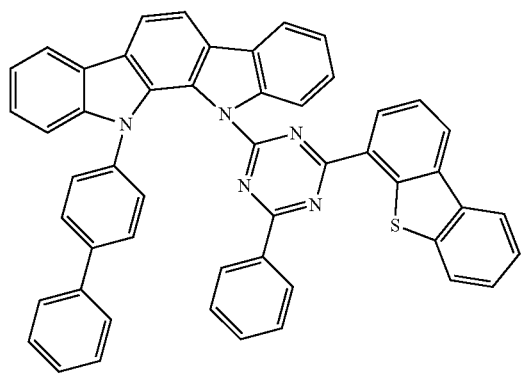
[A-45]
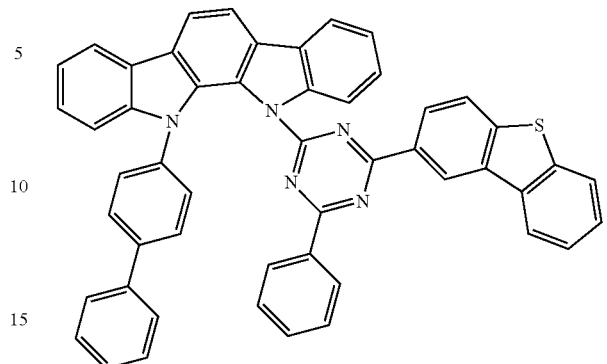
[A-46]
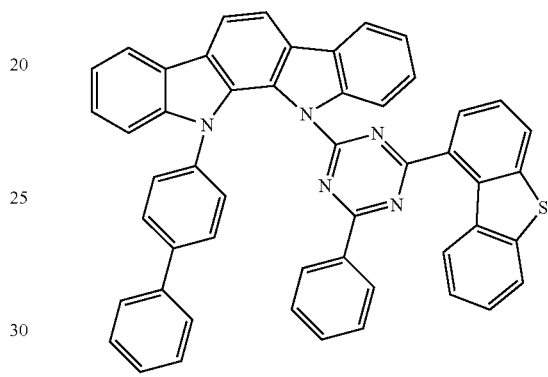
[A-47]
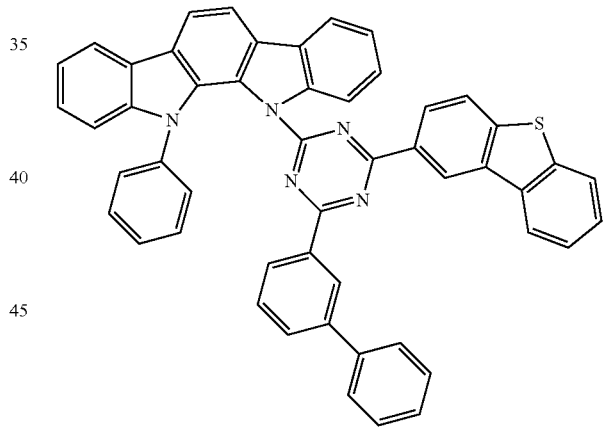
[A-48]
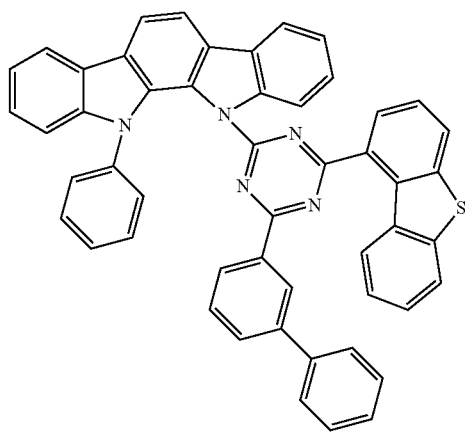

[A-49]
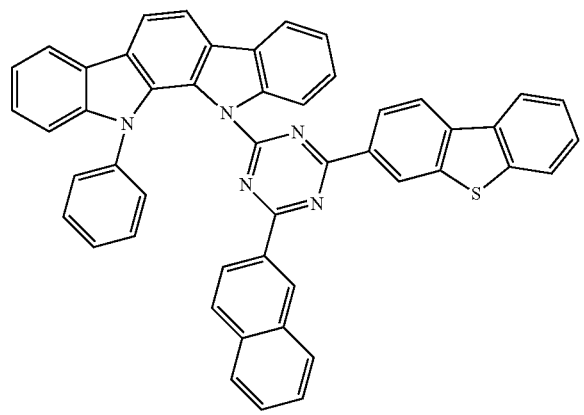
[A-50]
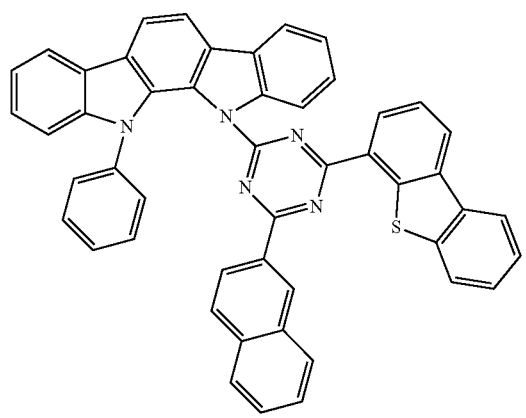
[A-51]
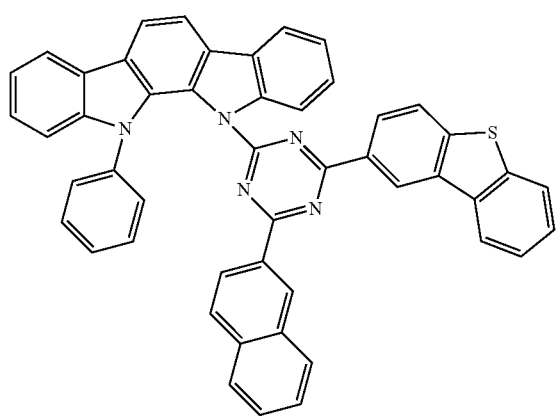
[A-52]
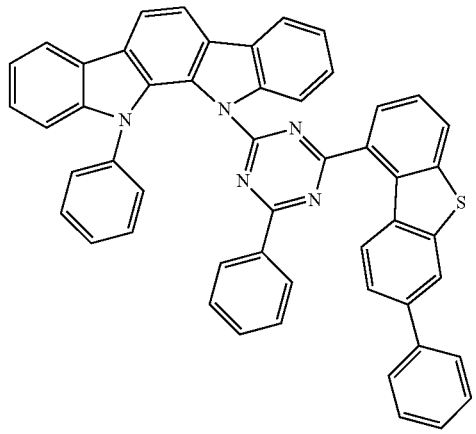
[A-53]
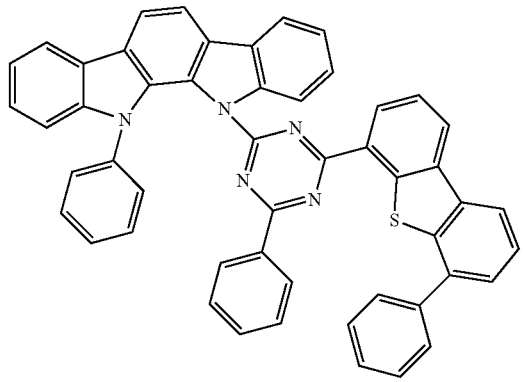
[A-54]
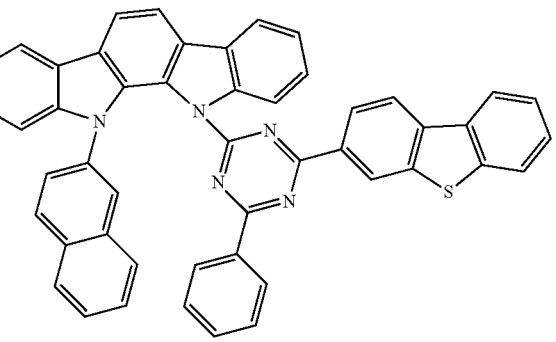
[A-55]

-continued
[A-56]
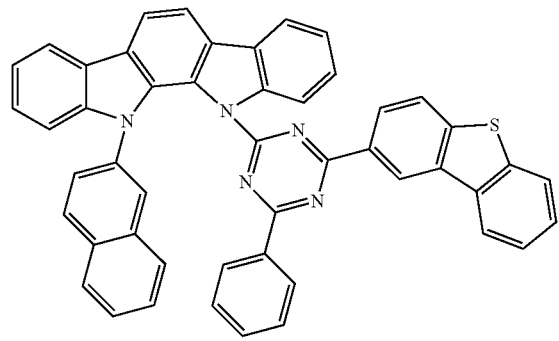
[A-57]
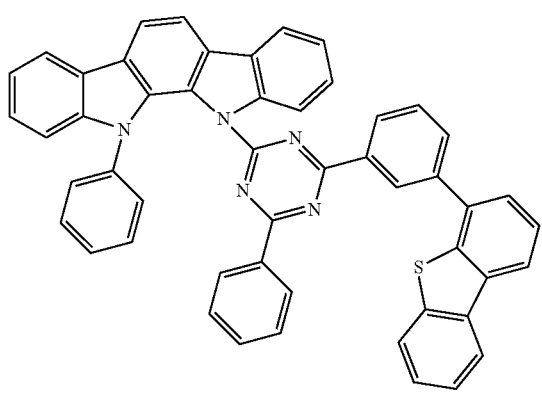
[A-58]
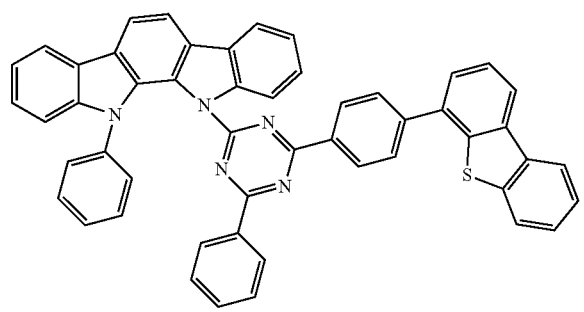
[A-59]
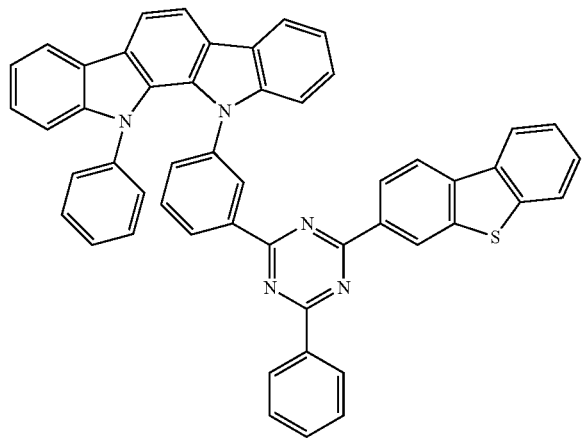
[A-60]
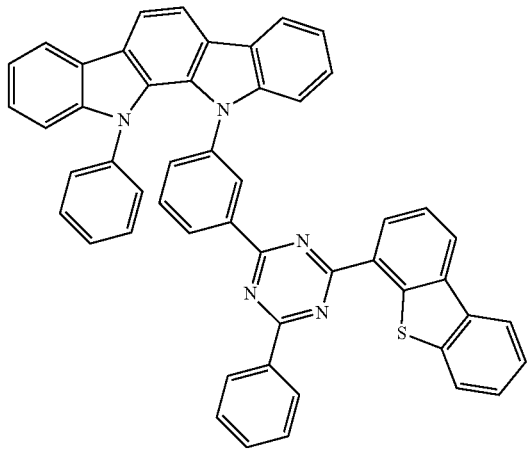
[A-61]
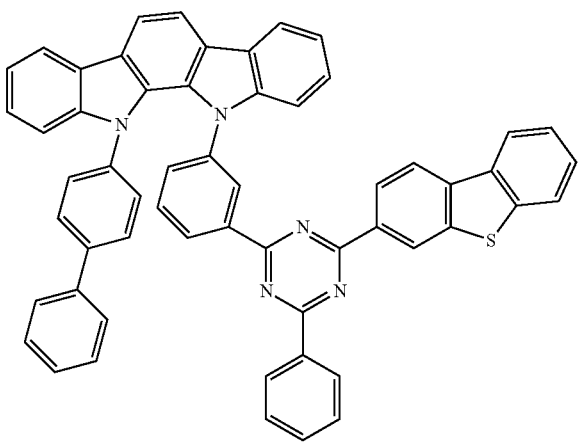
[A-62]
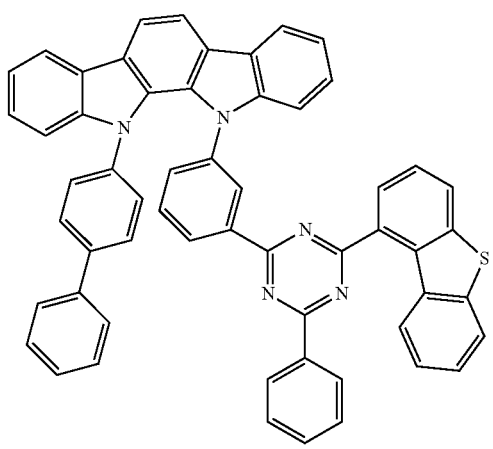

[A-63]
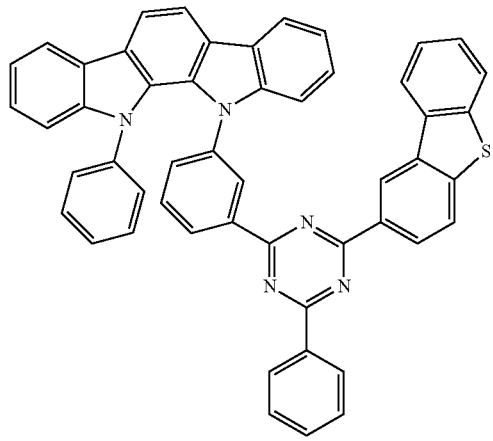
[A-66]
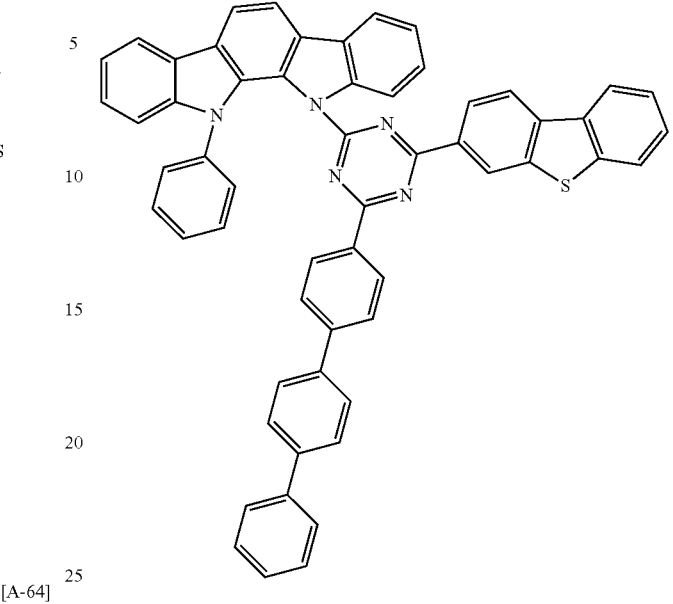
[A-64]
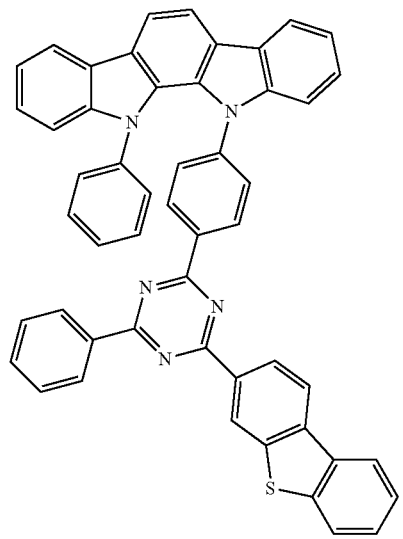
[A-67]
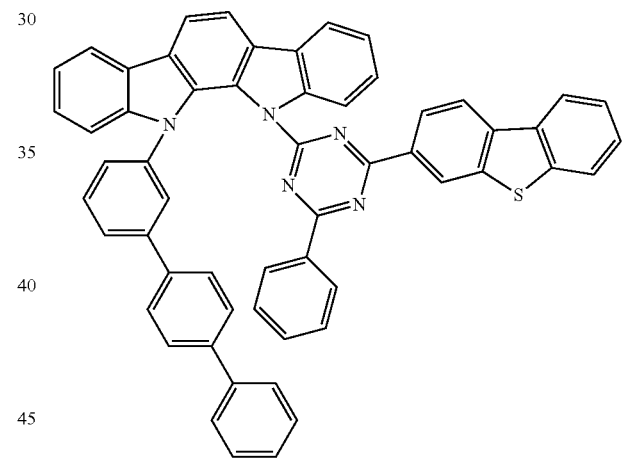
[A-65]
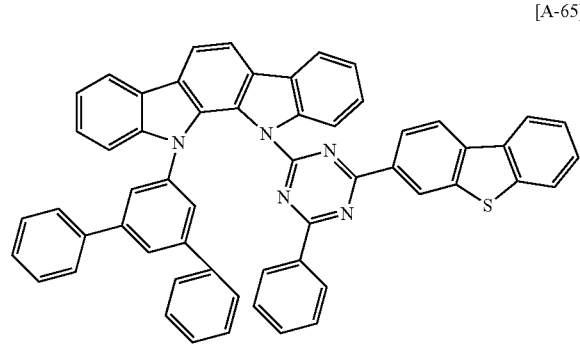
[A-68]
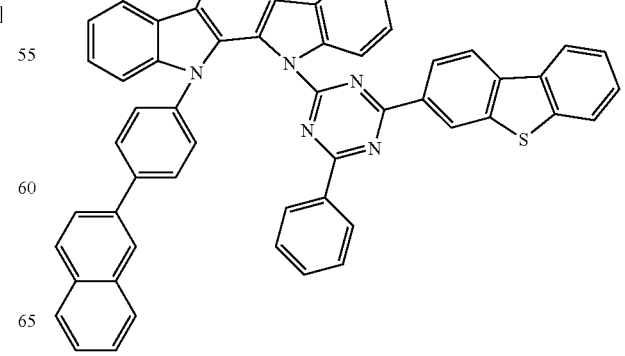

[A-69]
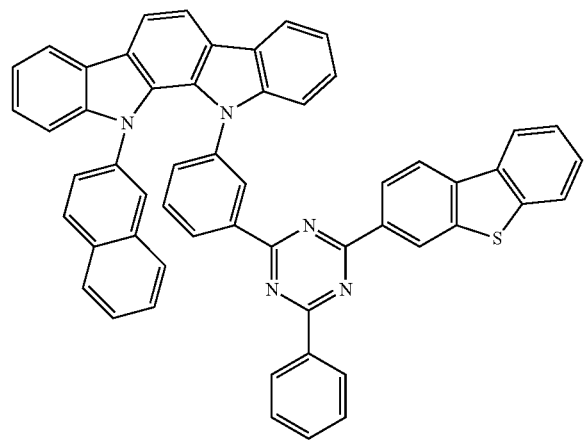
[A-72]
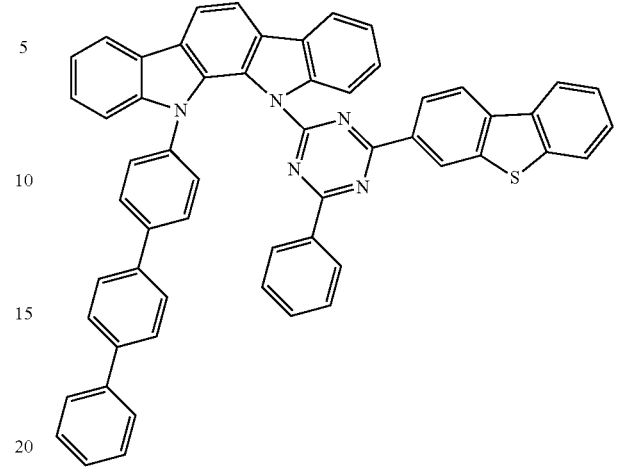
[A-70]
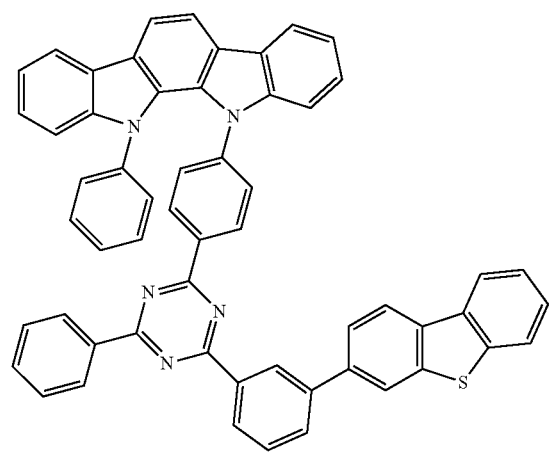
[A-73]
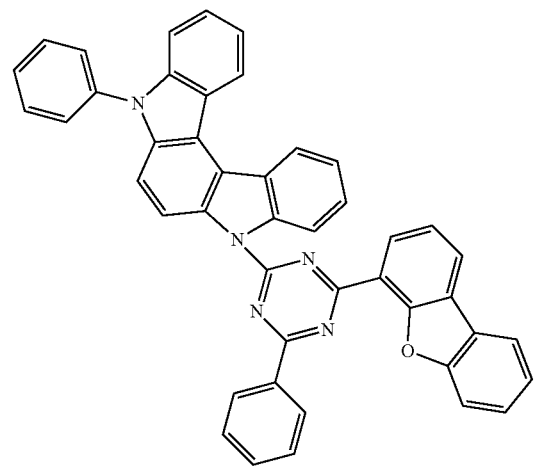
[A-71]
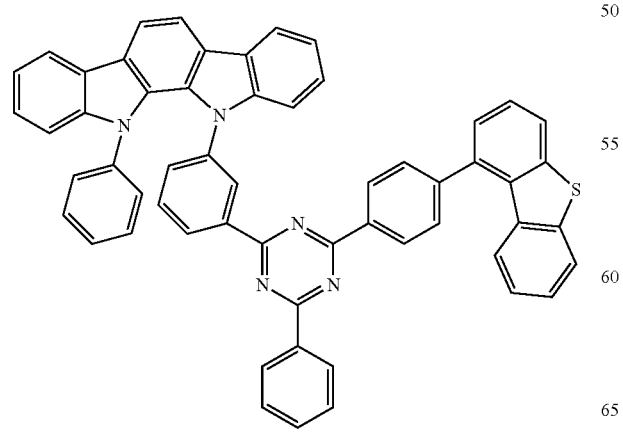
[A-74]
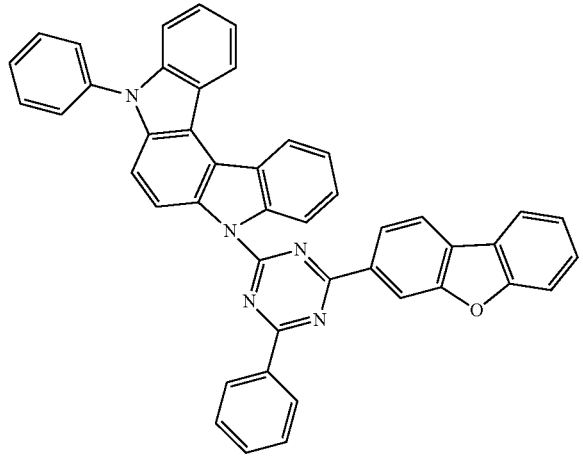

[A-75]
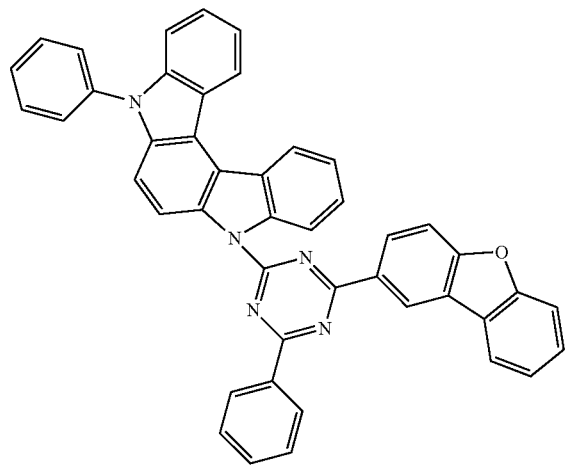
[A-78]
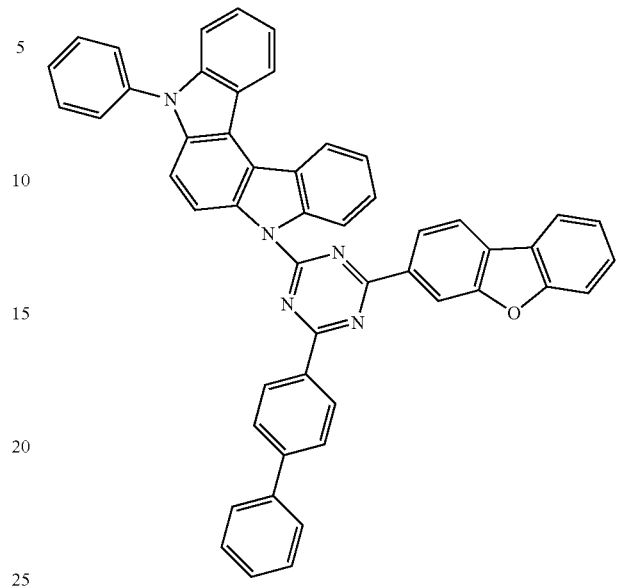
[A-76]
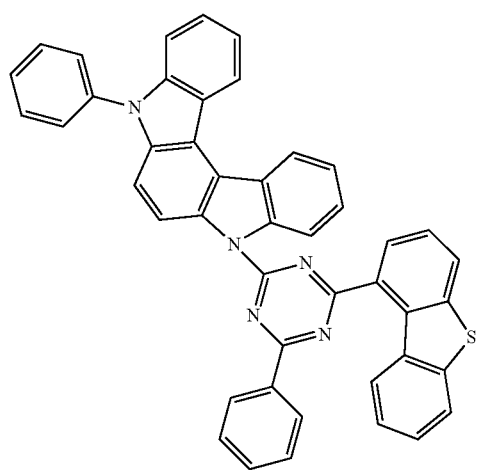
[A-79]
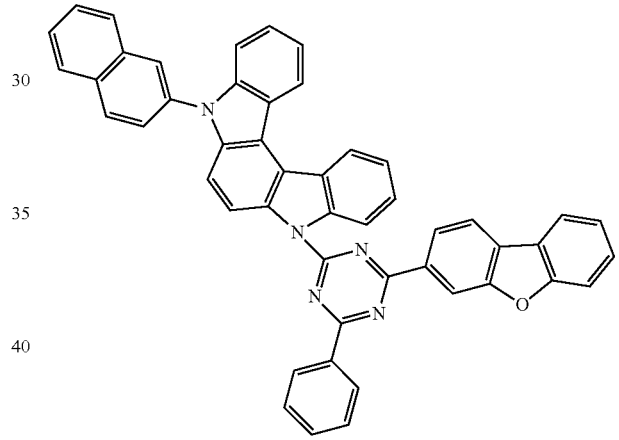
[A-77]
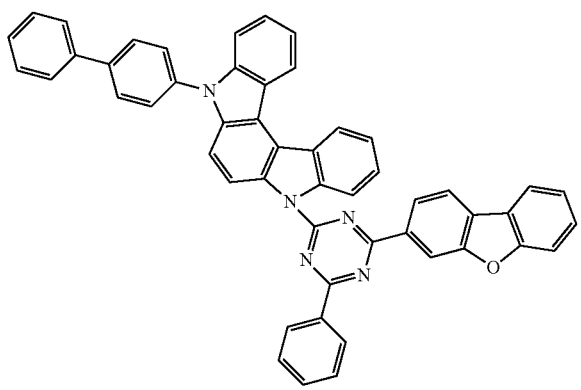
[A-80]
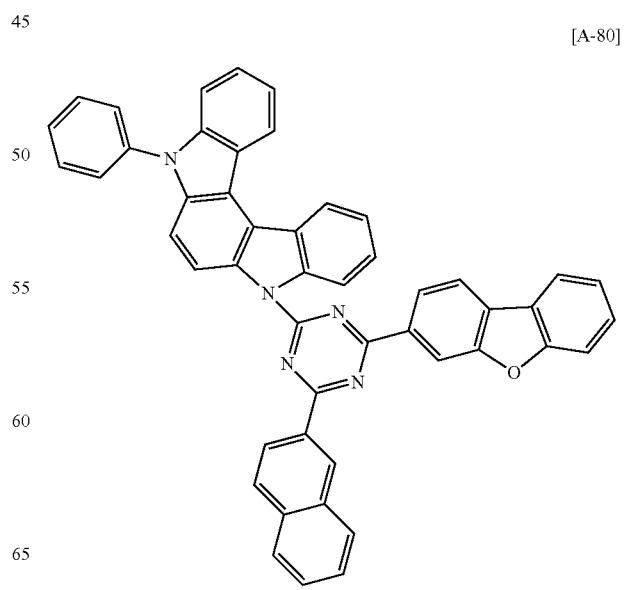

[A-81]
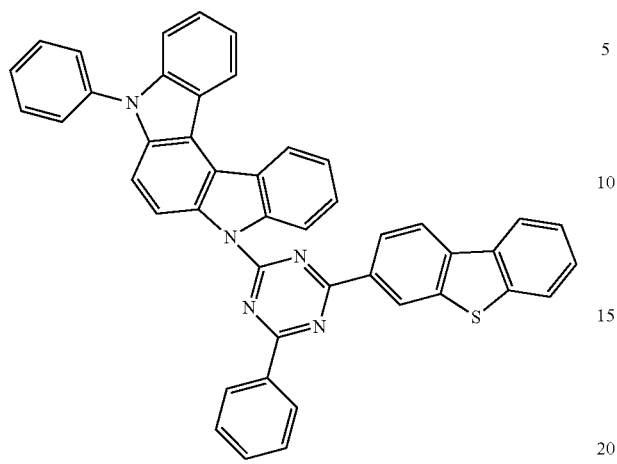
[A-82]
[A-83]
[A-84]
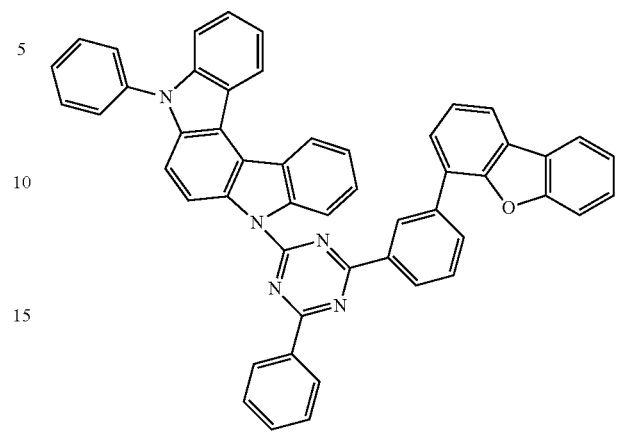
[A-85]
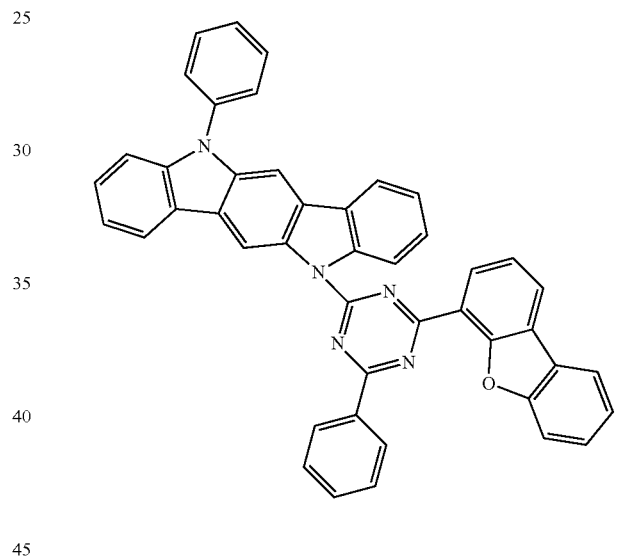
[A-86]
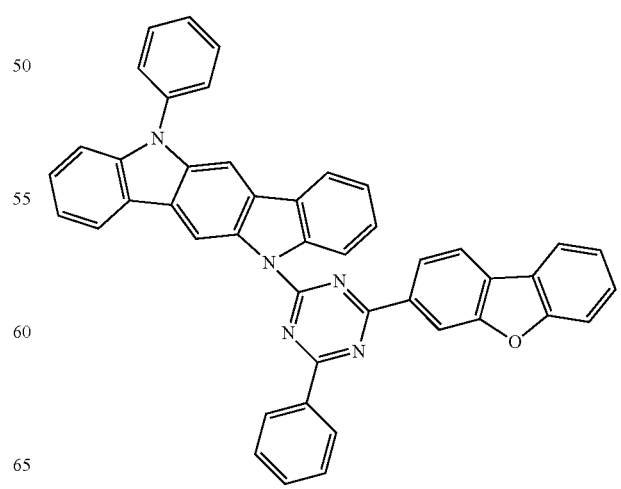

[A-87]
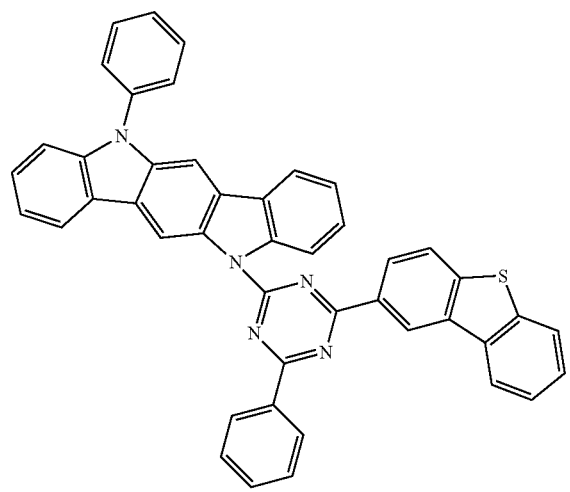
[A-88]
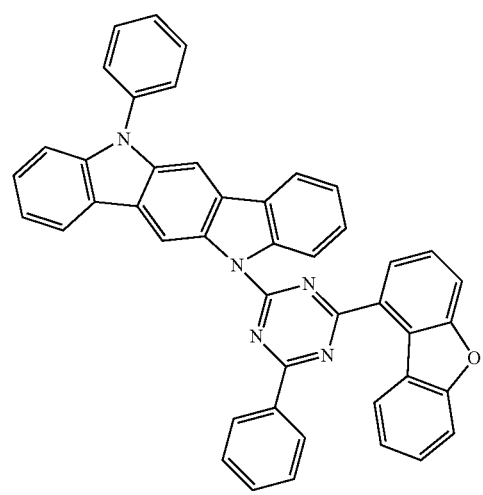
[A-89]
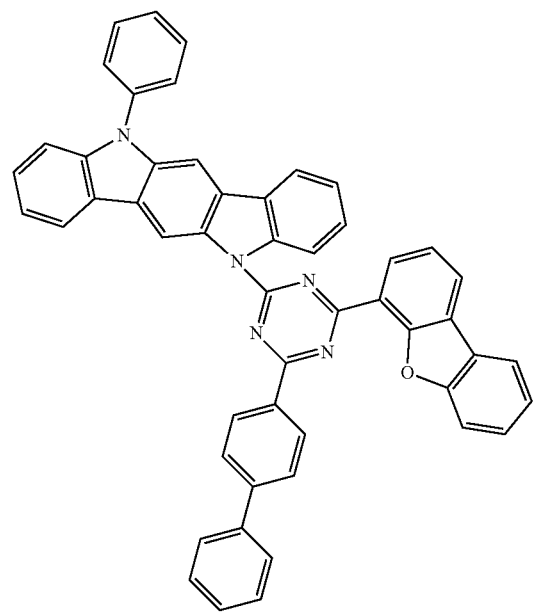
[A-90]
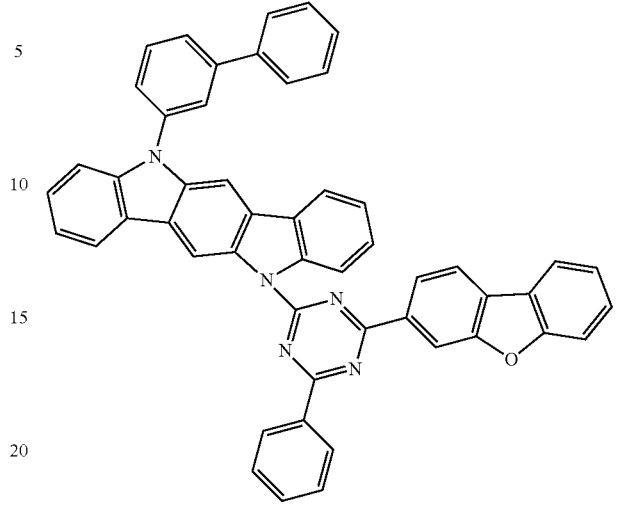
[A-91]
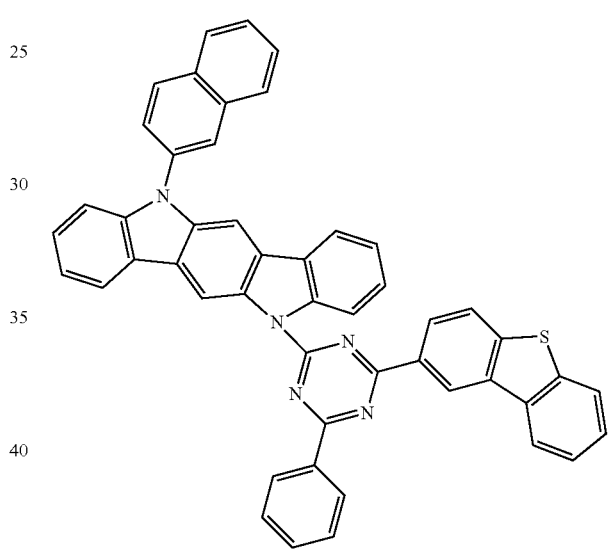
[A-92]
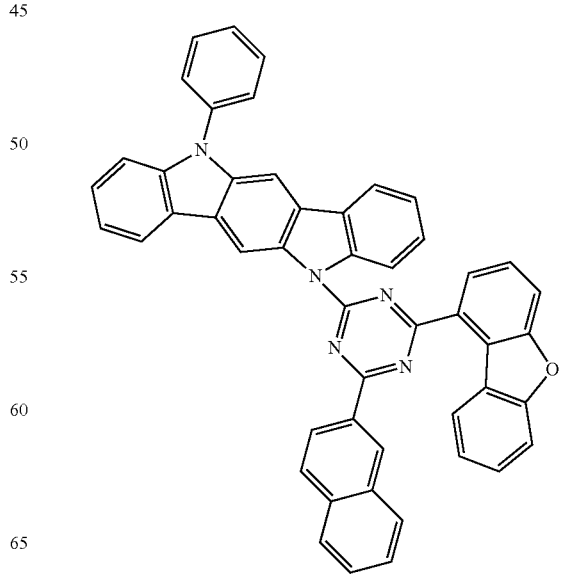

[A-93]
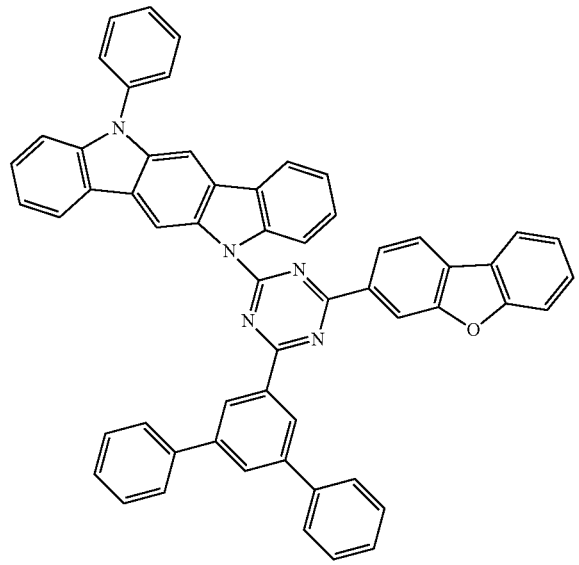
[A-95]
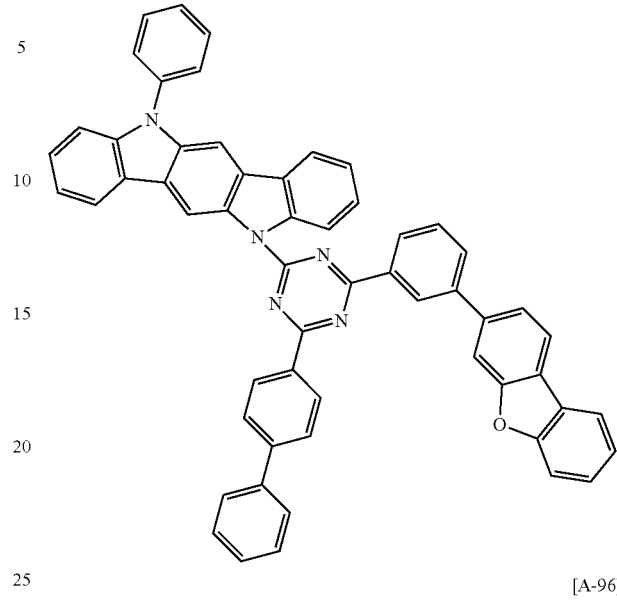
[A-96]
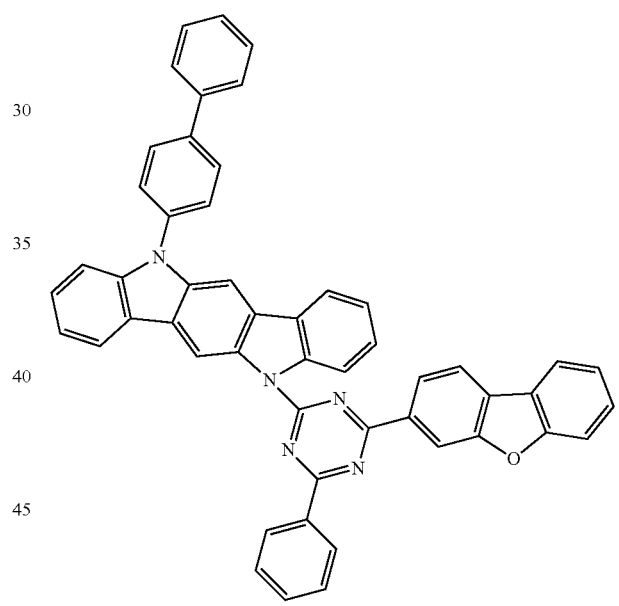
[A-94]
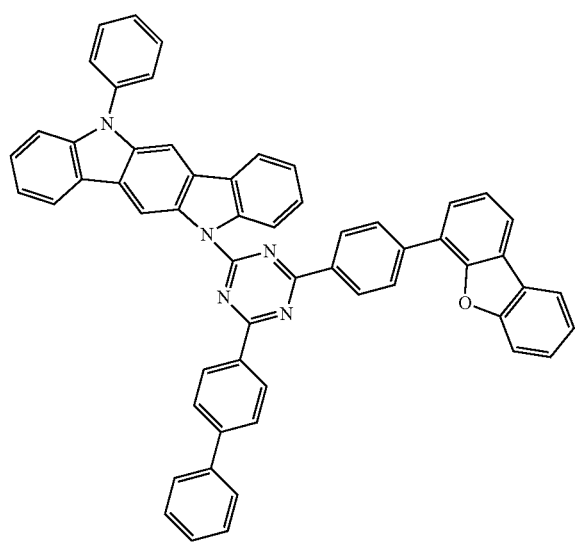
[A-97]
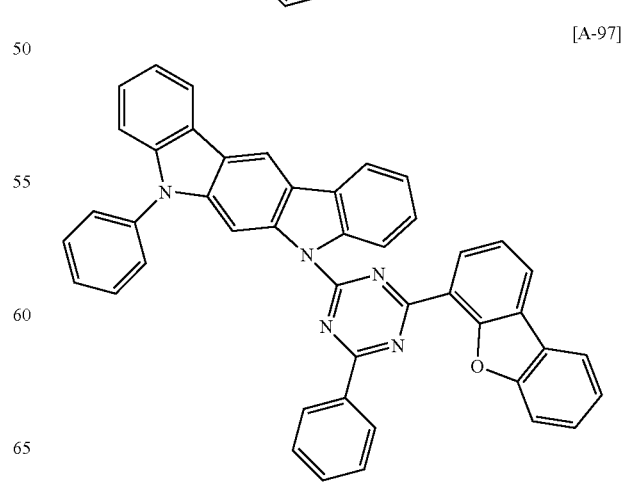

[A-98]
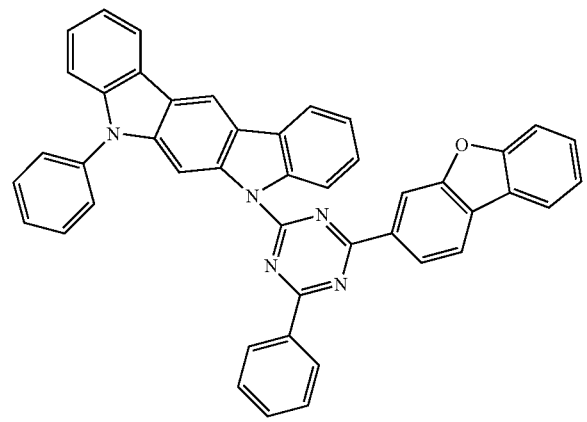
[A-99]
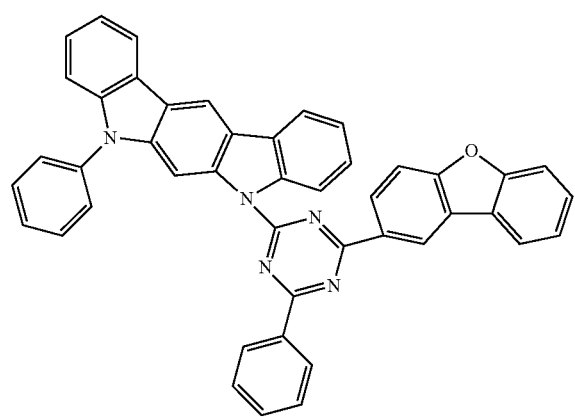
[A-100]
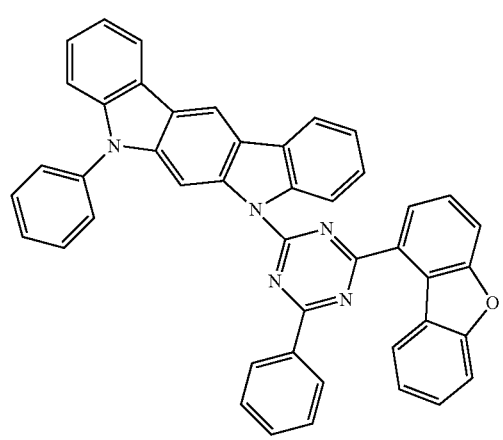
[A-101]
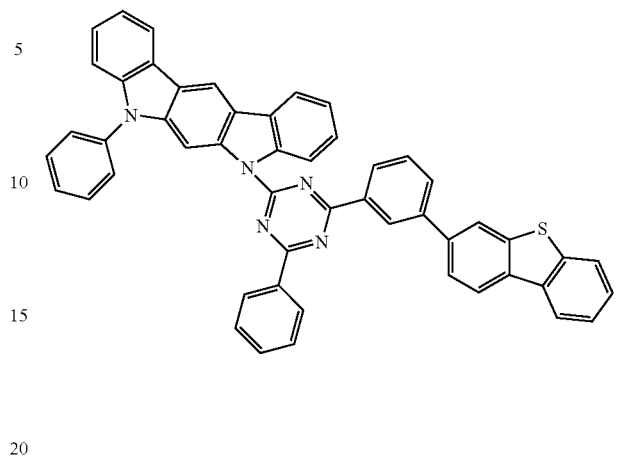
[A-102]
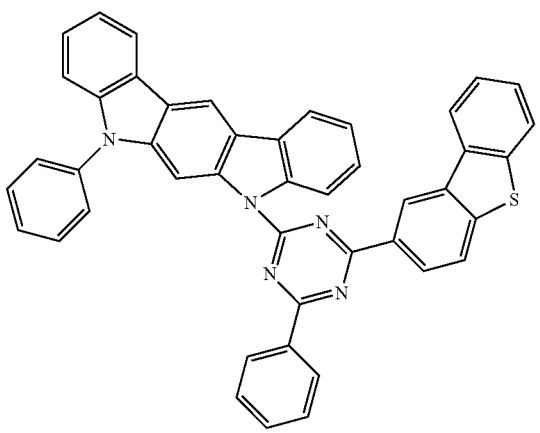
[A-103]
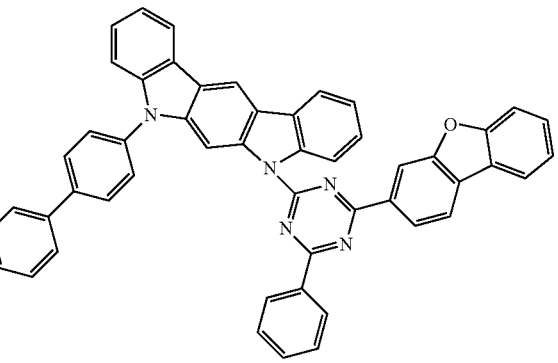

[A-104]
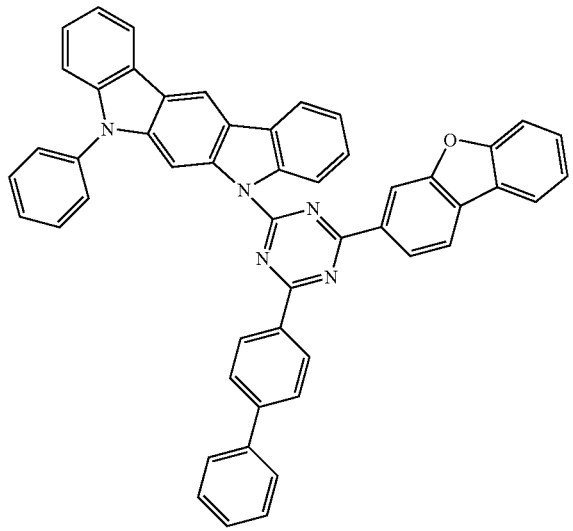
[A-105]
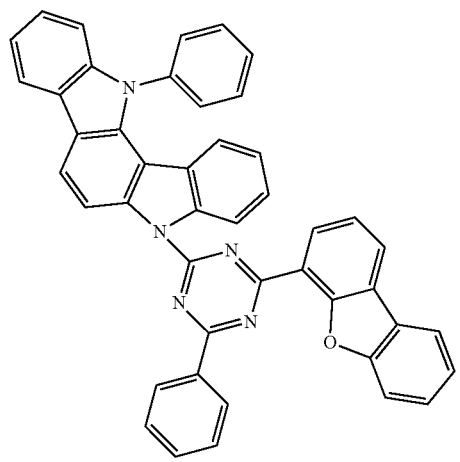
[A-106]
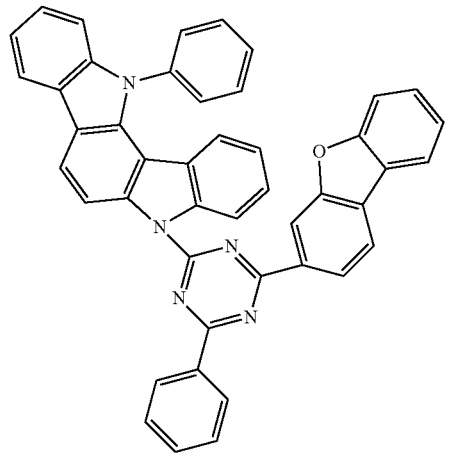
[A-107]
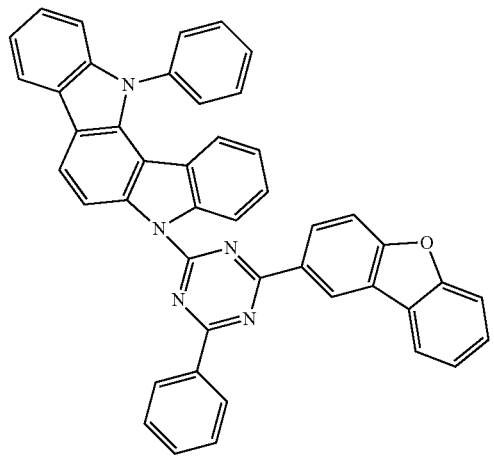
[A-108]
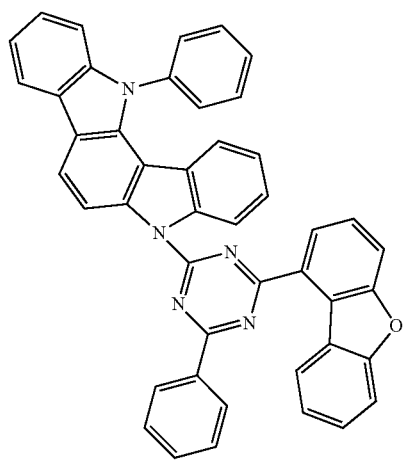
[A-109]
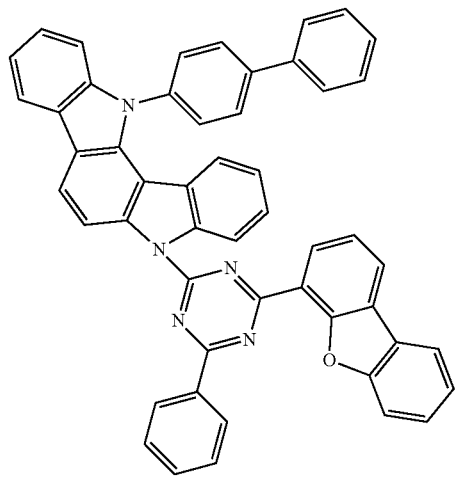

-continued
[A-110]
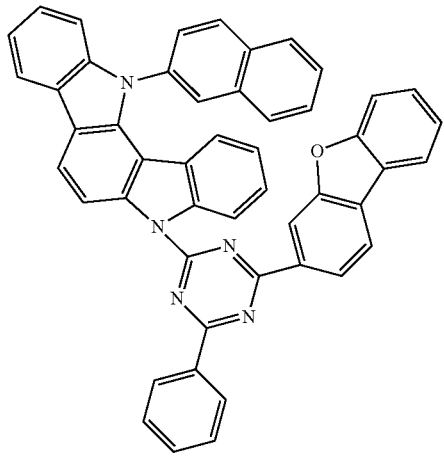
[A-113]
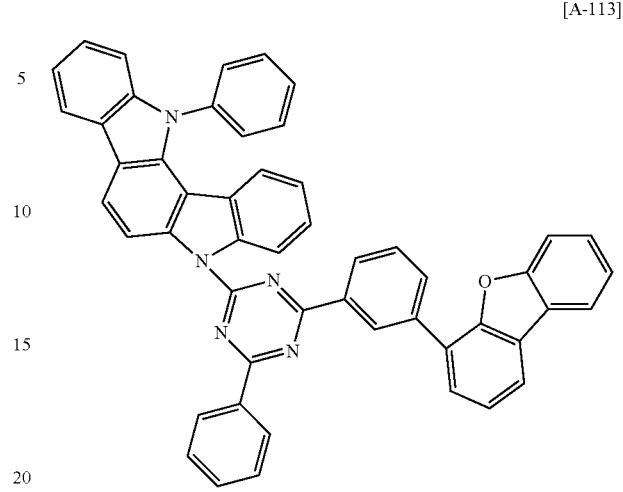
[A-111]
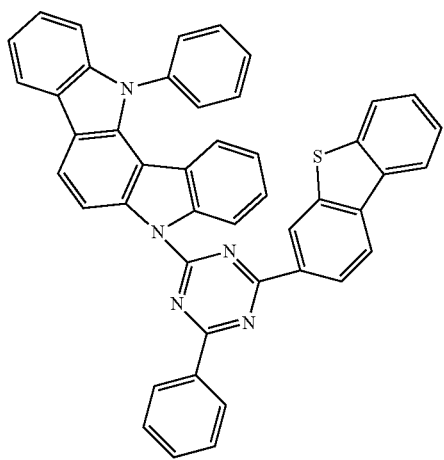
[A-114]
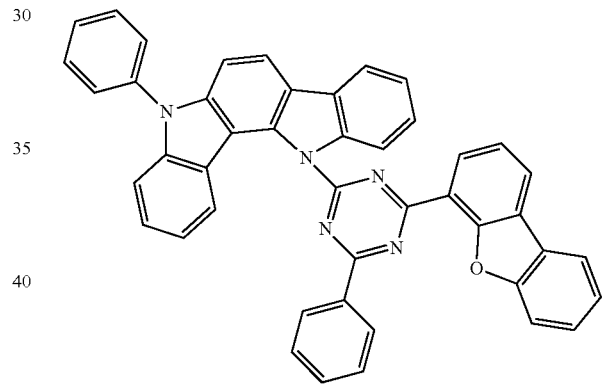
[A-112]
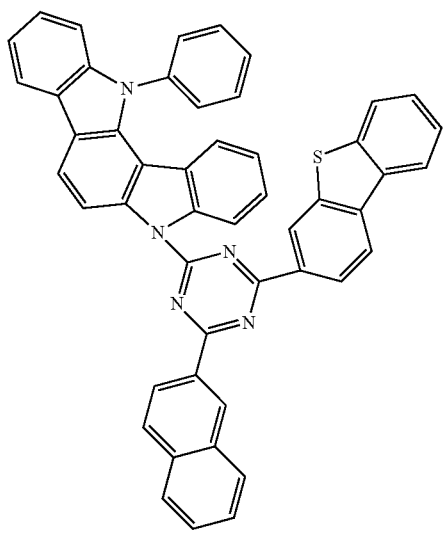
[A-115]
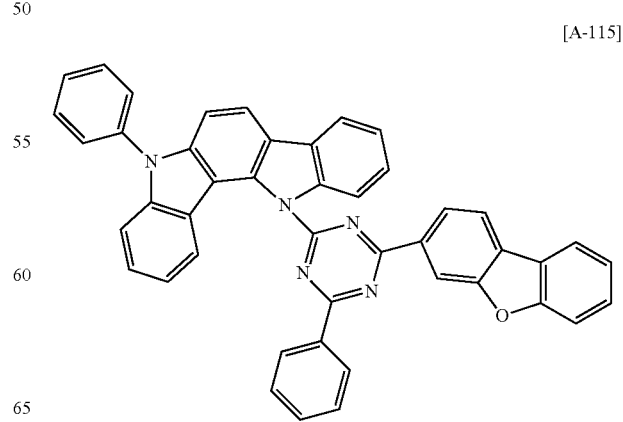

[A-116]
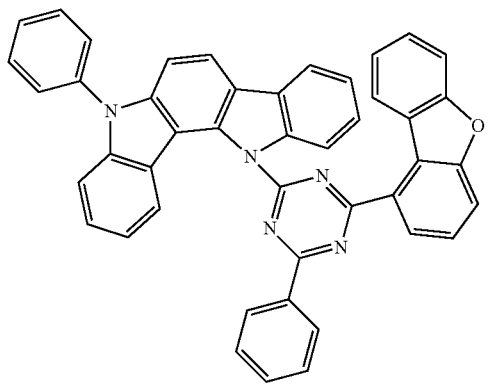
[A-119]
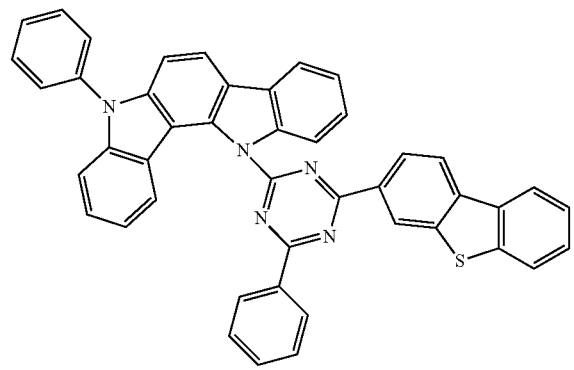
[A-117]
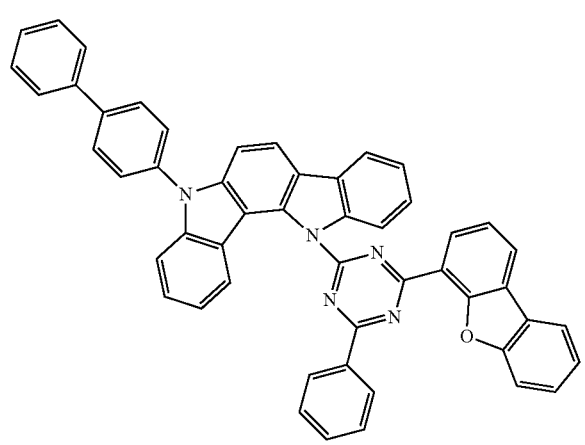
[A-120]
[Group 2]
[B-1]
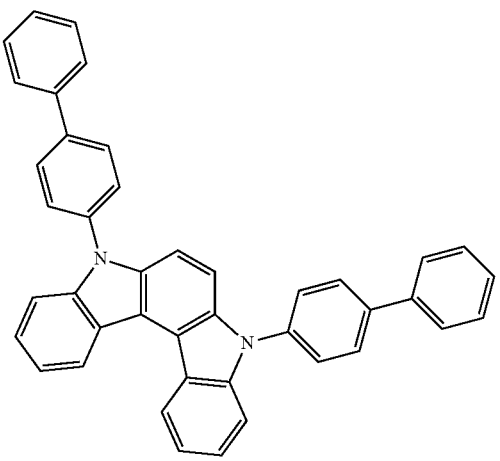
[A-118]

-continued
[B-2]
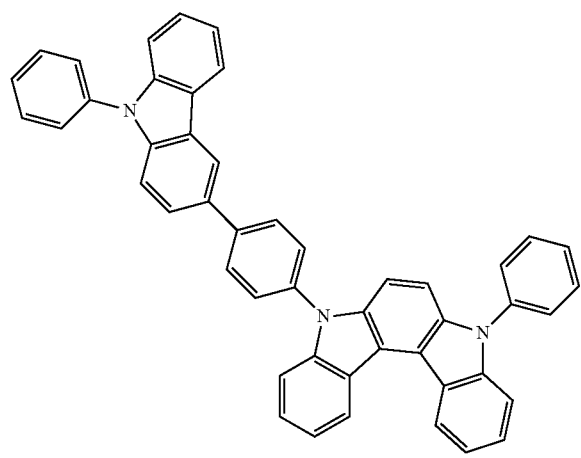
[B-3]
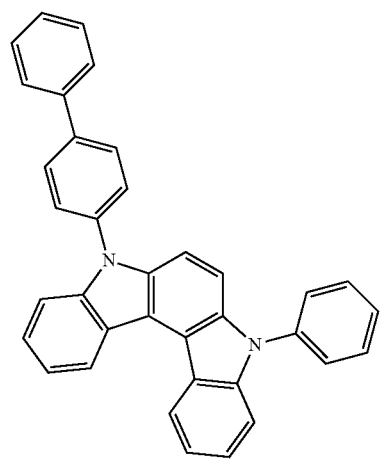
[B-4]
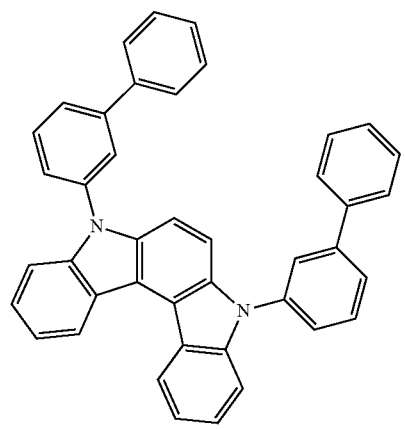
[B-5]
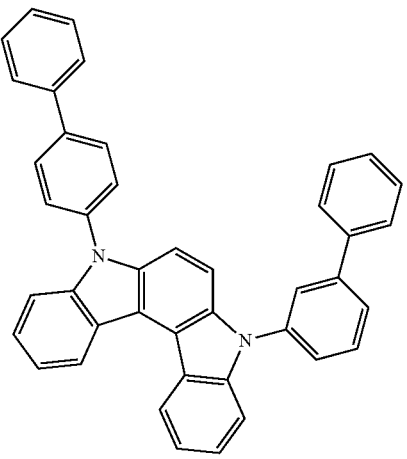
[B-6]
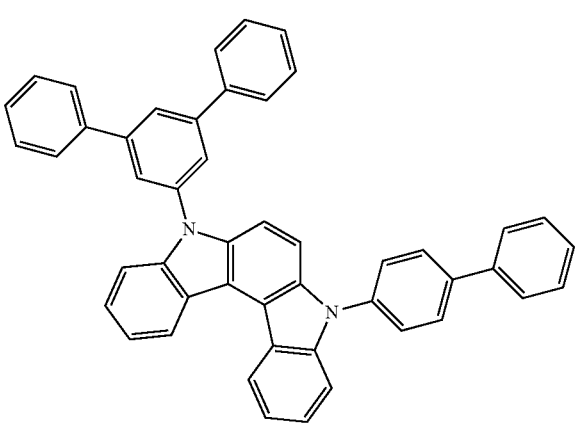
[B-7]
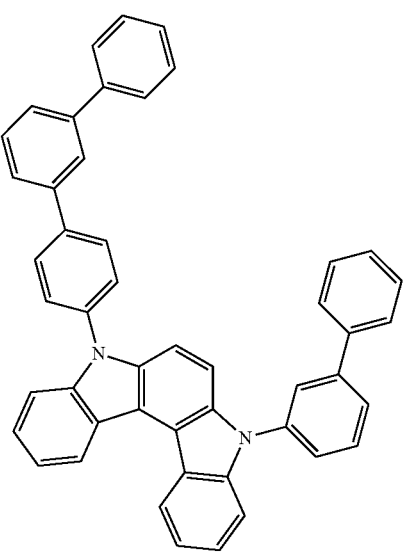

[B-8]
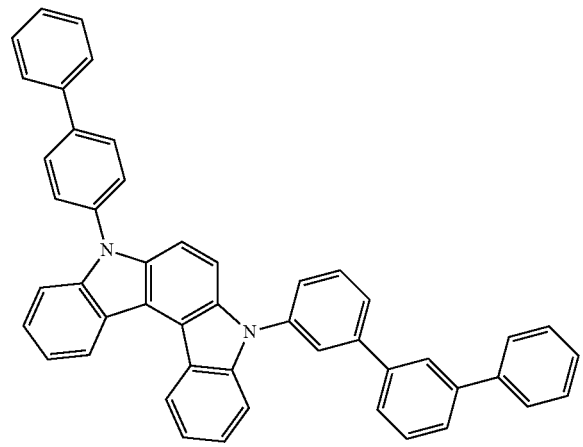
[B-9]
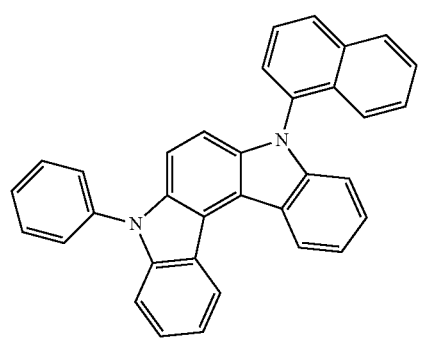
[B-10]
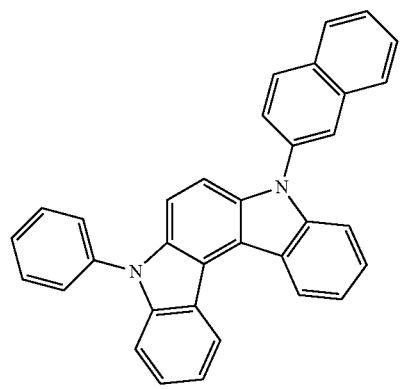
[B-11]
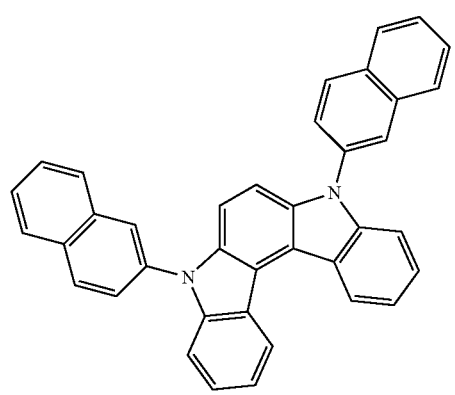
[B-12]
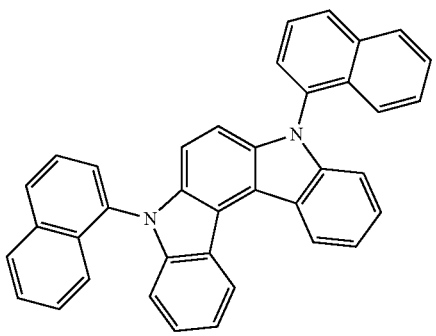
[B-13]
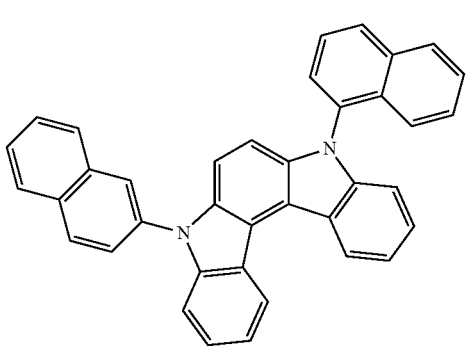
[B-14]
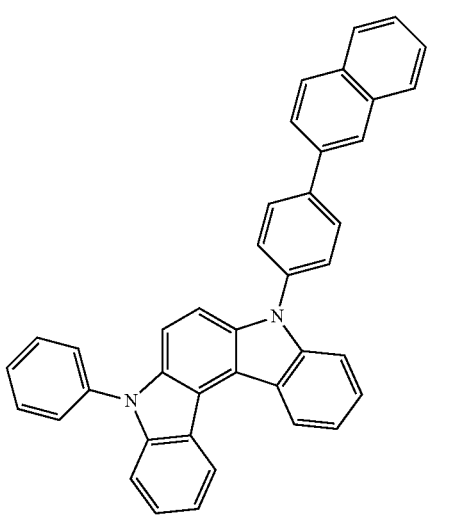
[B-15]
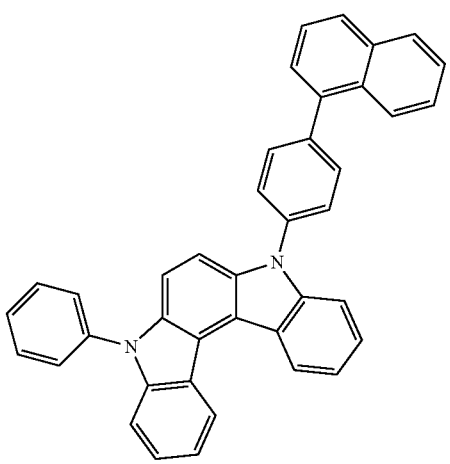

-continued
[B-16]
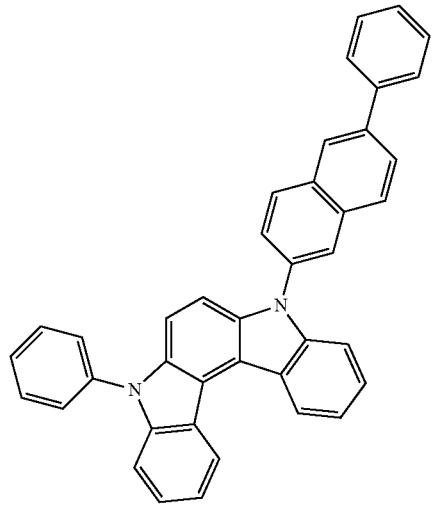
[B-17]
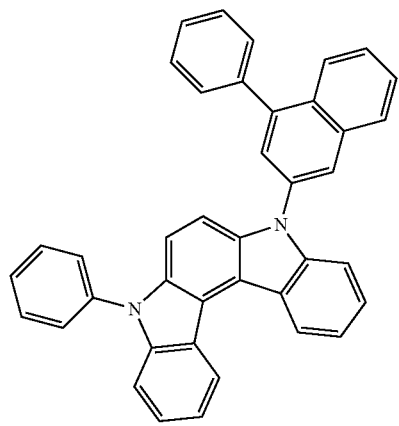
[B-18]
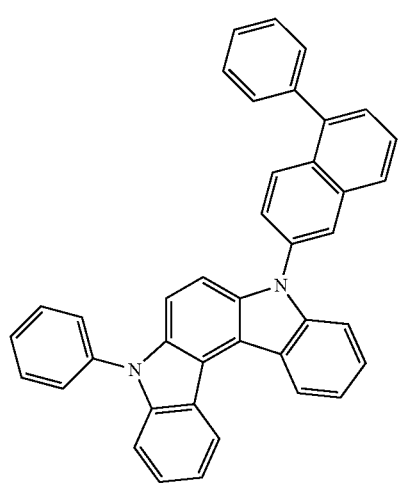
-continued
[B-19]
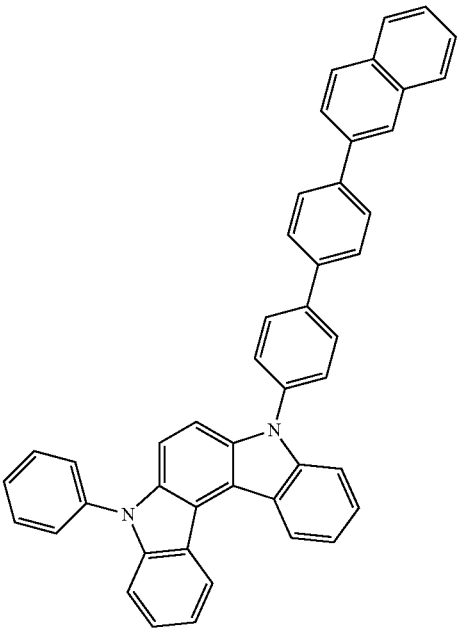
[B-20]
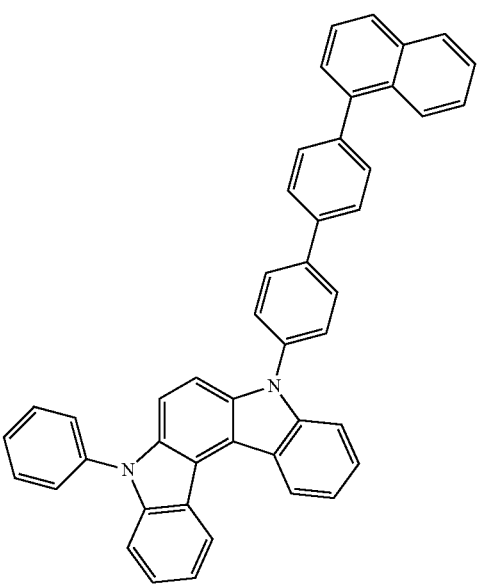
[B-21]
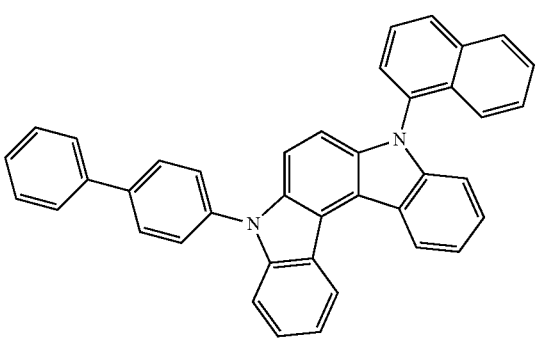

[B-22]
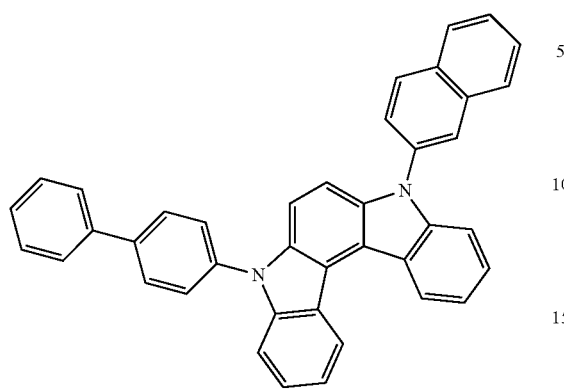
[B-23]
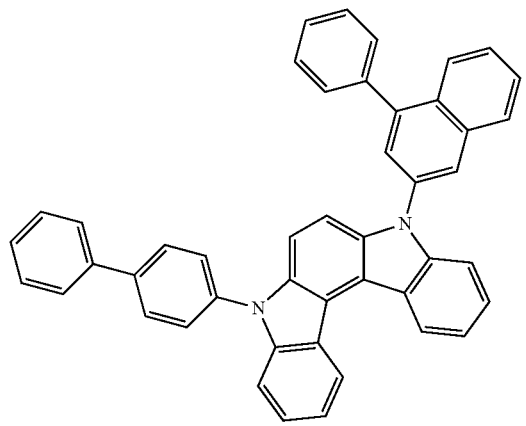
[B-24]
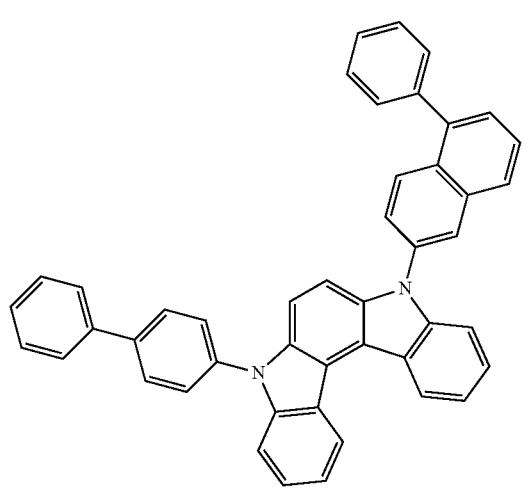
[B-25]
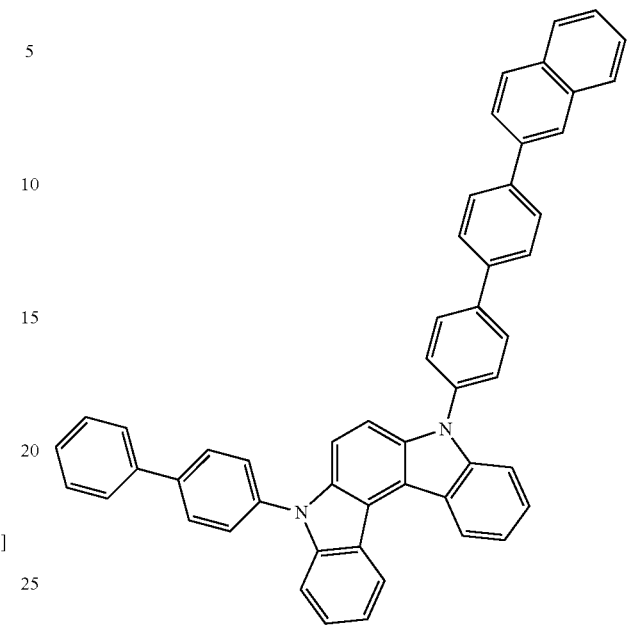
[B-26]
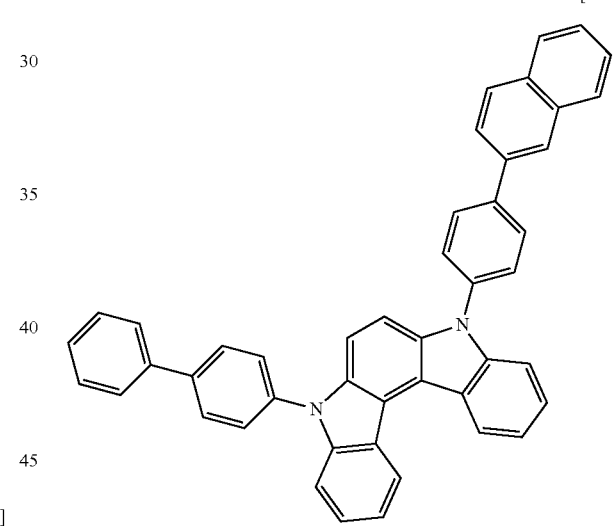
[B-27]
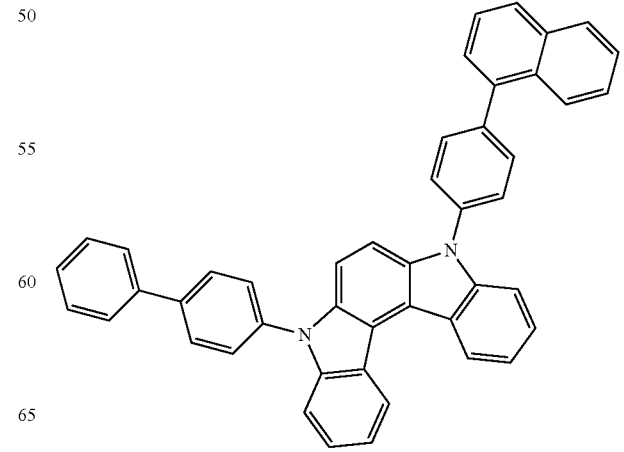

-continued
[B-28]
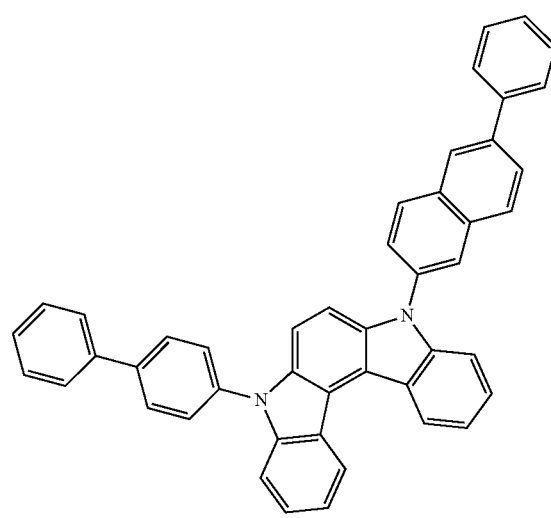
[B-29]
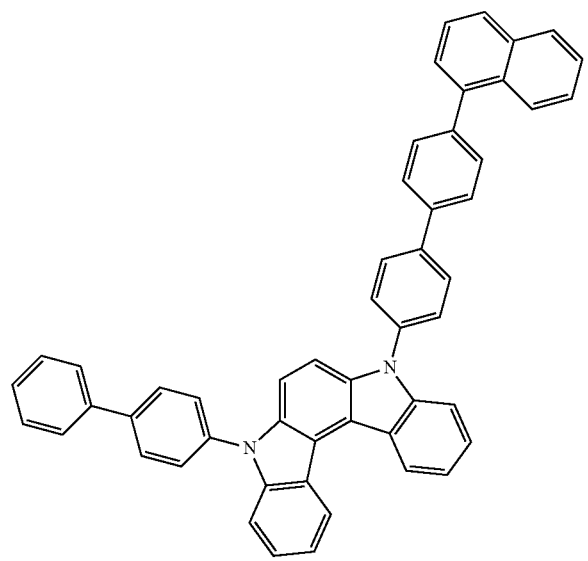
[B-30]
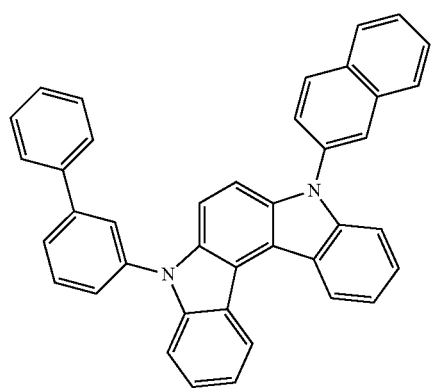
-continued
[B-31]
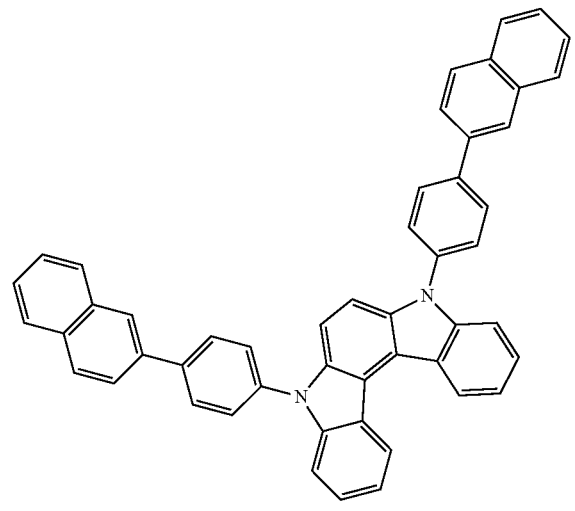
[B-32]
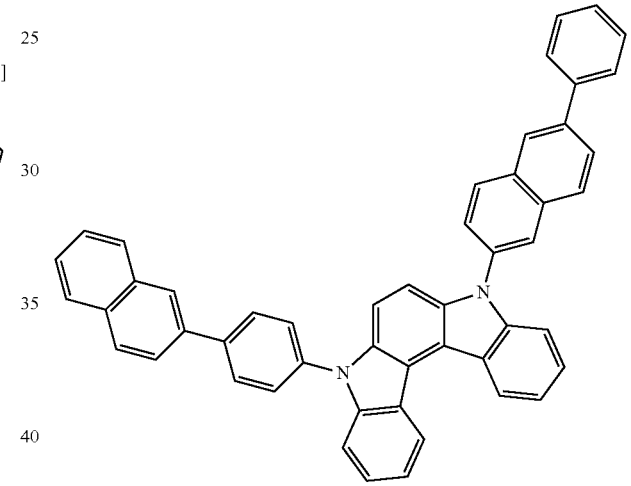
[B-33]
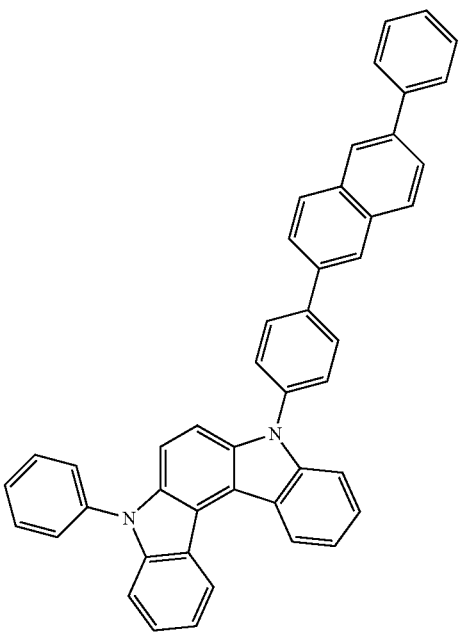

-continued
[B-34]
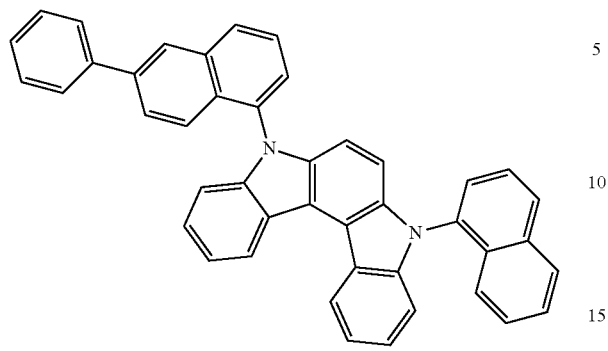
[B-35]
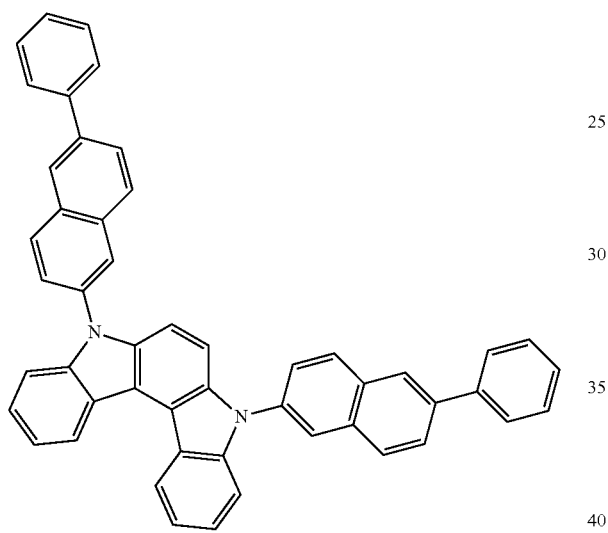
[B-36]
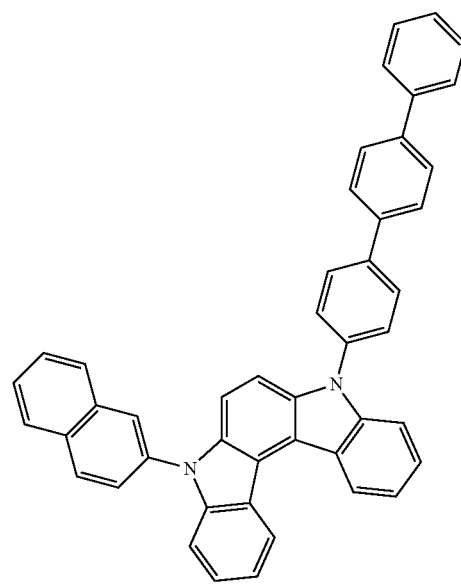
-continued
[B-37]
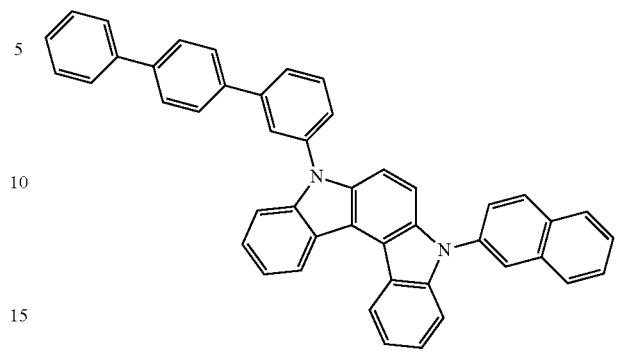
[B-38]
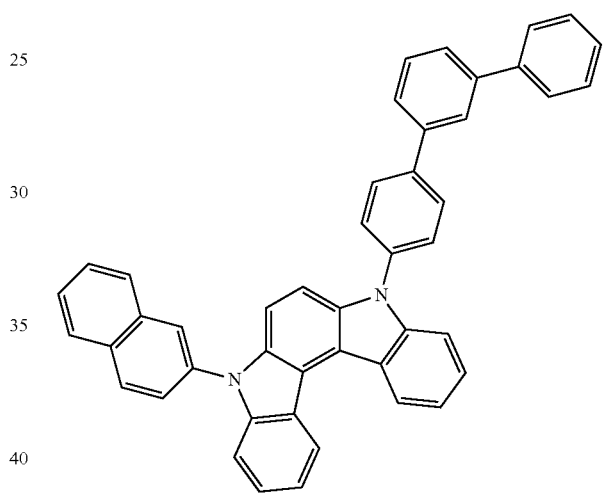
[B-39]
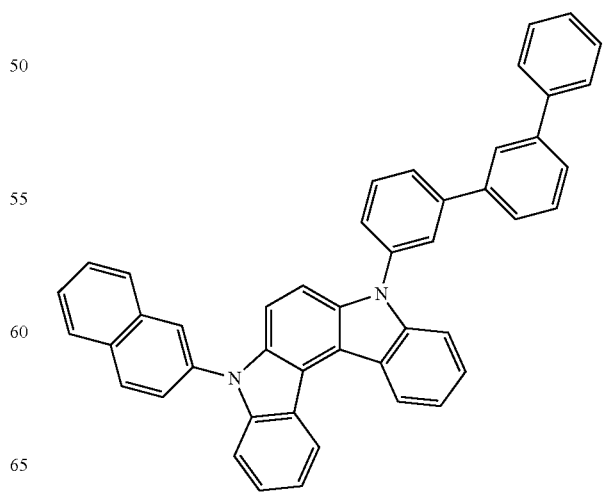

[B-40]
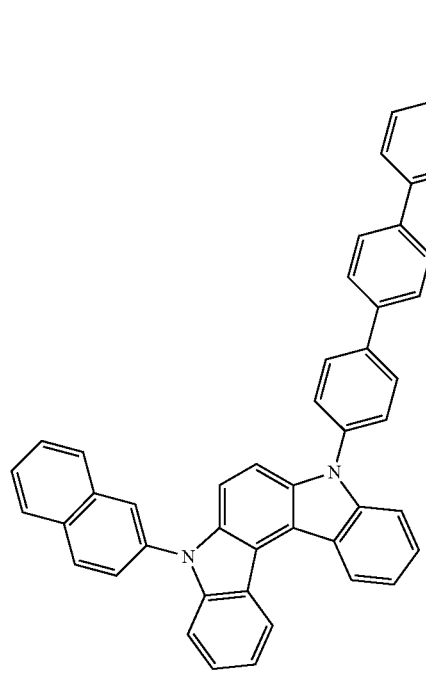
[B-42]
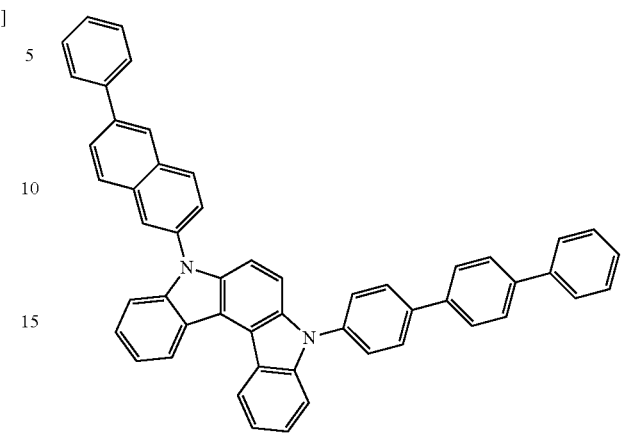
[B-43]
[B-41]
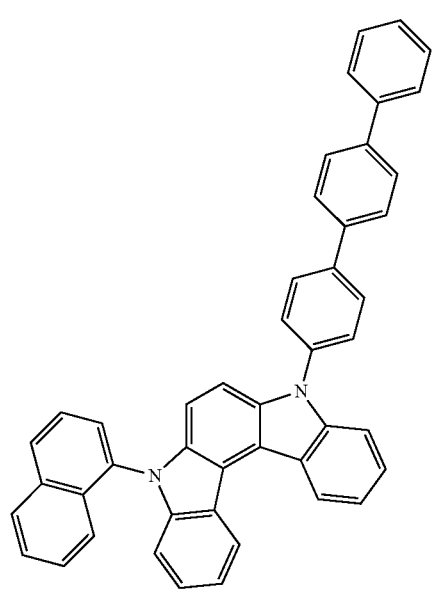
[B-44]
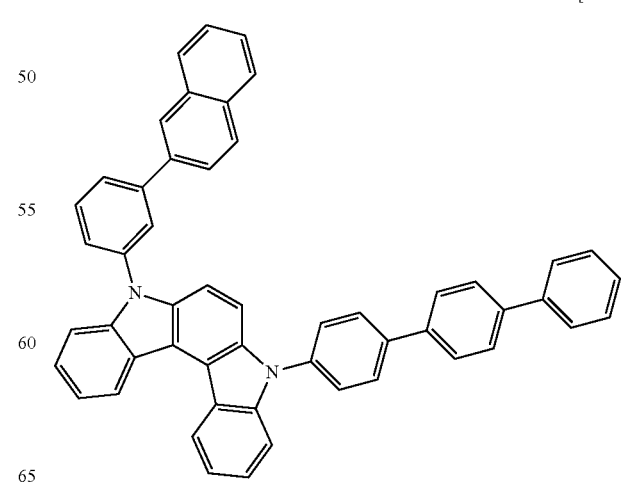

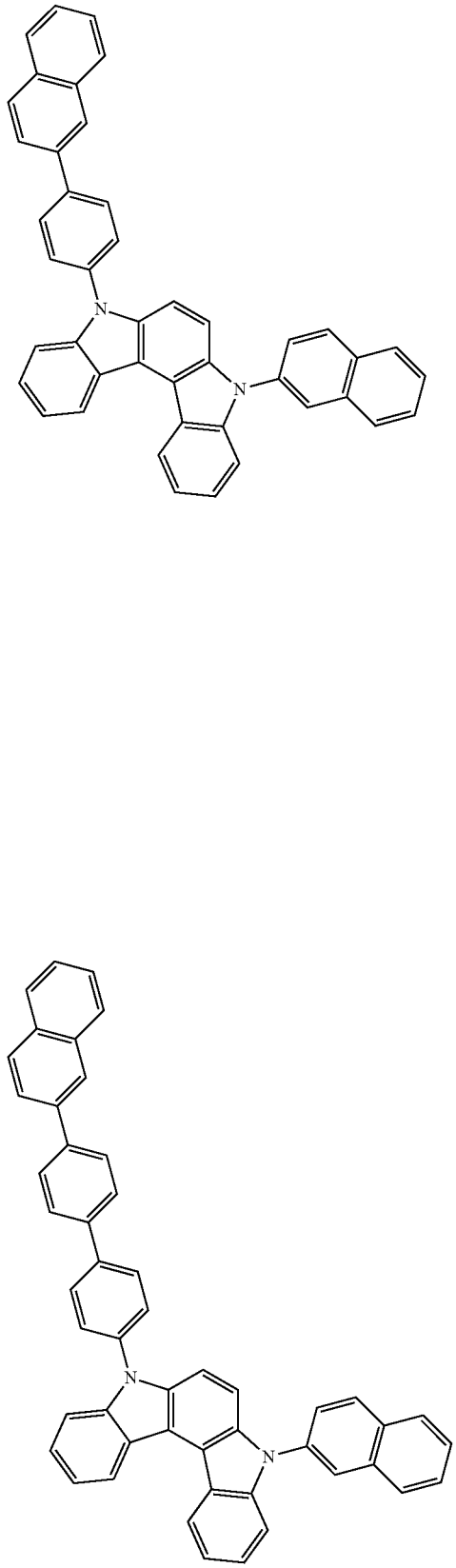
[B-45]
[B-46]
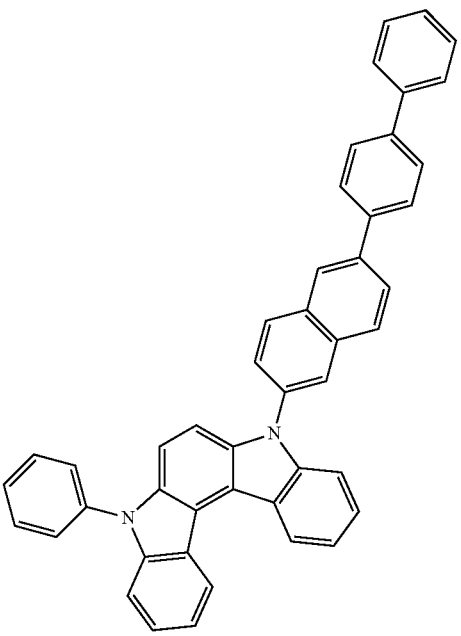
[B-47]
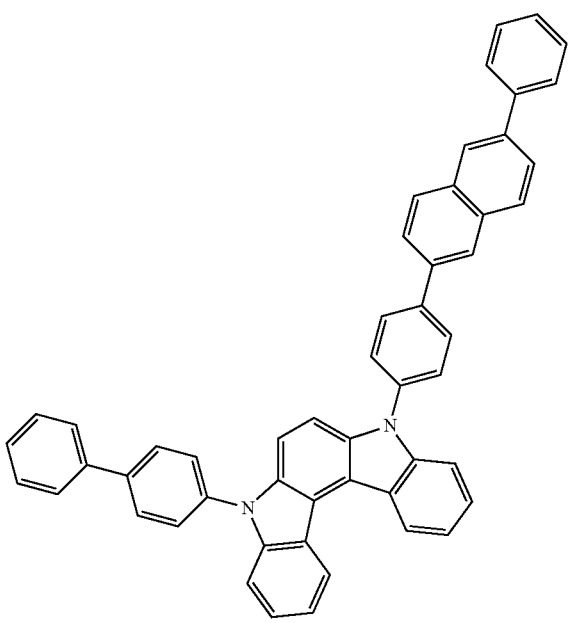
[B-48]
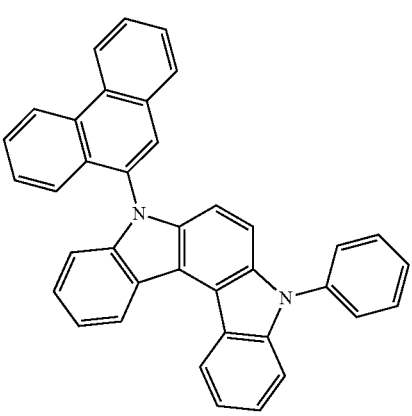
[B-49]

[B-50]
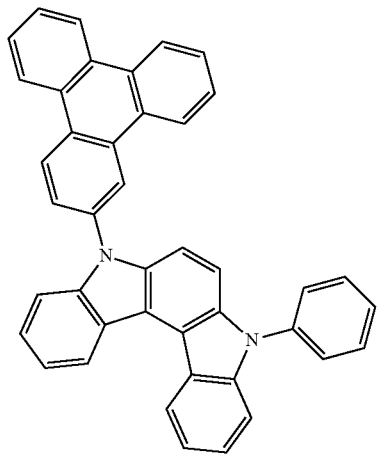
[B-51]
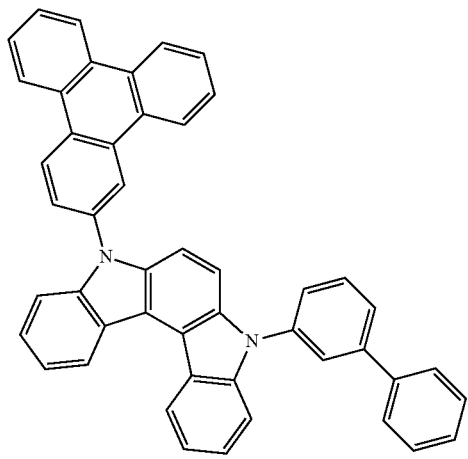
[B-52]
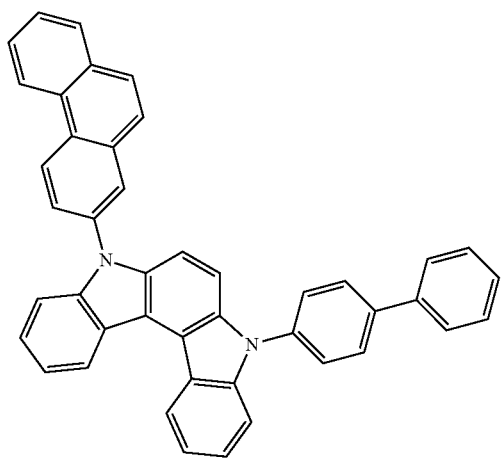
[B-53]
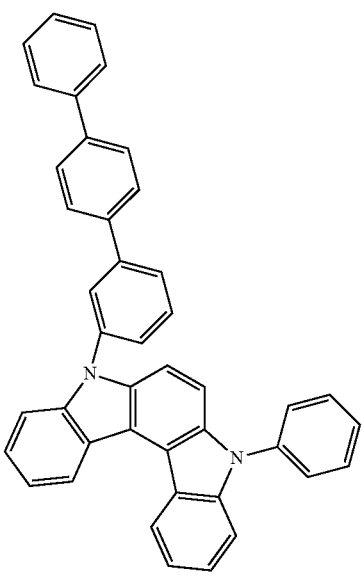
[B-54]
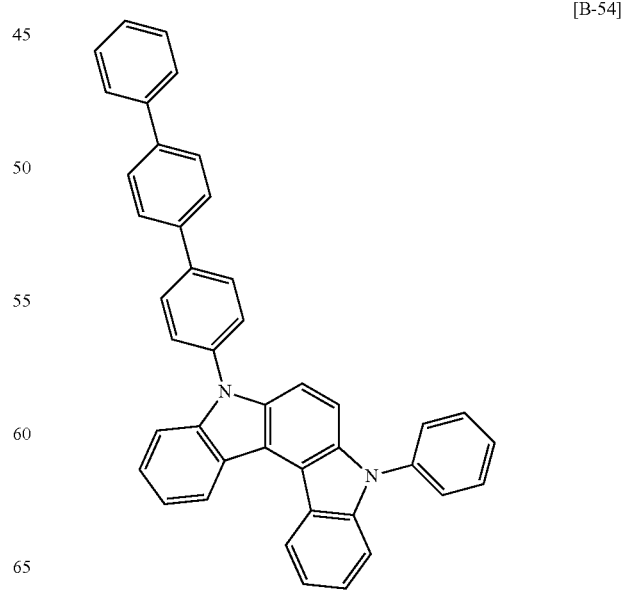

[B-55]
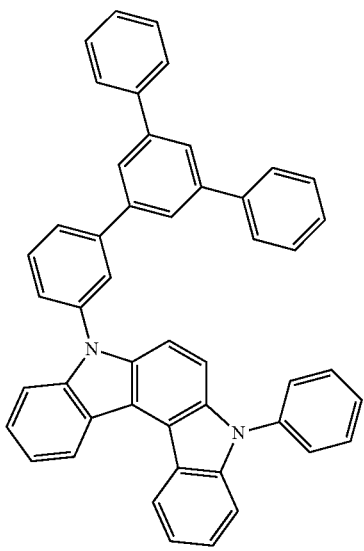

[B-56]
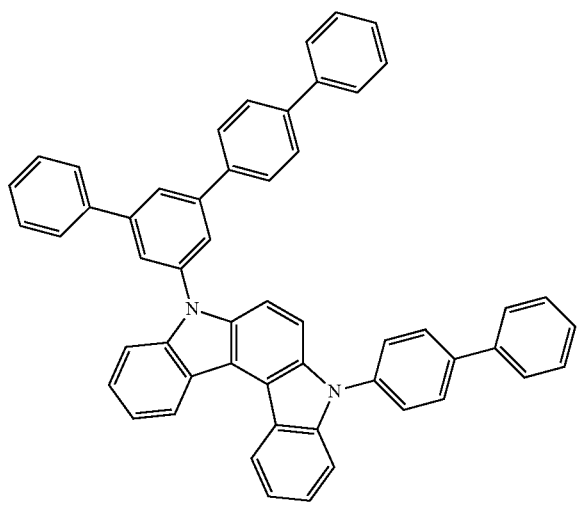

[B-57]
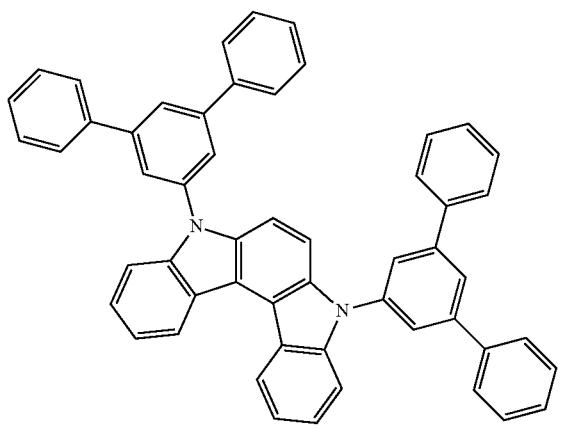

The aforementioned organic layer 105 includes a light emitting layer 130, and the composition for the organic optoelectronic device may be included as a host, for example a red host of the light emitting layer.

The anode 120 may be made of a conductor having a large work function to help hole injection and may be for example made of a metal, a metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example made of a metal, a metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

FIG. 2 is a cross-sectional view showing an organic light emitting diode according to another embodiment.

Referring to FIG. 2, an organic light emitting diode 200 further include a hole auxiliary layer 140 in addition to the light emitting layer 130. The hole auxiliary layer 140 may further increase hole injection and/or hole mobility and block electrons between the anode 120 and the light emitting layer 130. The hole auxiliary layer 140 may be, for example a hole transport layer, a hole injection layer, and/or an electron blocking layer, and may include at least one layer.

The organic layer 105 of FIG. 1 or 2 may further include an electron injection layer, an electron transport layer, an electron transport auxiliary layer, a hole transport layer, a hole transport auxiliary layer, a hole injection layer, or a combination thereof even if they are not shown. The compound for the organic optoelectronic device of the present invention may be included in these organic layers. The organic light emitting diodes 100 and 200 may be manufactured by forming an anode or a cathode on a substrate, forming an organic layer using a dry film formation method such as a vacuum deposition method (evaporation), sputtering, plasma plating, and ion plating or a wet coating method such as spin coating, dipping, and flow coating, and forming a cathode or an anode thereon.

The aforementioned first compound for the organic optoelectronic device and second compound for the organic optoelectronic device may variously provide various compositions, and mobility of charges may be controlled by controlling the ratio of compounds. When the composition of the present invention is used as a host, a combination ratio thereof may be different according to types and properties of a used dopant and the first compound for the organic optoelectronic device and the second compound for the organic optoelectronic device may be for example included in a weight ratio of 1:10 to 10:1. Specifically, they may be included in a weight ratio of 2:8 to 8:2, 2:8 to 7:3, 2:8 to 6:4, 2:8 to 5:5, 3:7 to 8:2, 3:7 to 7:3, 3:7 to 6:4, for example 3:7 to 5:5. For more specific examples, a mixing ratio of the first compound for the organic optoelectronic device and the second compound for the organic optoelectronic device may be 3:7, 4:6 or 5:5.

The composition may further include one or more host compound in addition to the first compound for the organic optoelectronic device and the second compound for the organic optoelectronic device.

The dopant may be a red phosphorescent dopant.

The dopant is mixed in a small amount to cause light emission, and may be generally a material such as a metal complex that emits light by multiple excitation into a triplet or more. The dopant may be, for example an inorganic, organic, or organic/inorganic compound, and one or more kinds thereof may be used.

The dopant may be for example a phosphorescent dopant and examples of the phosphorescent dopant may be an organometallic compound including Ir, Pt, Os, Ti, Zr, Hf, Eu, Tb, Tm, Fe, Co, Ni, Ru, Rh, Pd, or a combination thereof. The phosphorescent dopant may be for example a compound represented by Chemical Formula Z, but is not limited thereto.

$$L_2MX$$  [Chemical Formula Z]

In Chemical Formula Z, M is a metal, and L and X are the same or different, and are a ligand to form a complex compound with M.

The M may be for example Ir, Pt, Os, Ti, Zr, Hf, Eu, Tb, Tm, Fe, Co, Ni, Ru, Rh, Pd, or a combination thereof and the L and X may be for example a bidendate ligand.

The organic optoelectronic device of the present invention includes a phosphorescent dopant having a maximum emission wavelength of 570 nm to 750 nm. That is, it includes a phosphorescent dopant having a maximum emission wavelength out of the green region. For example, the maximum emission wavelength may be 570 nm to 720 nm, 580 nm to 700 nm, 590 nm to 700 nm, 600 nm to 700 nm, or 600 nm to 650 nm which is a wavelength of a reddish region.

The phosphorescent dopant having the maximum emission wavelength of 570 nm to 750 nm according to present invention may be an iridium (Ir) complex or a platinum (Pt) complex and the platinum (Pt) complex may be for example represented by Chemical Formula 4-1. In addition, the iridium (Ir) complex may be for example represented by Chemical Formula 4-2.

[Chemical Formula 4-1]

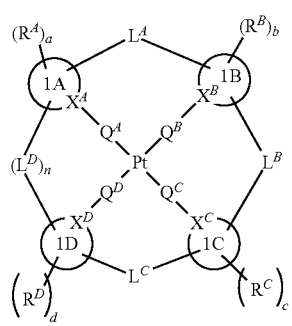

In Chemical Formula 4-1, $X^A$, $X^B$, $X^C$, and $X^D$ are elements that form unsaturated rings with each of 1A, 1B, 1C, and 1D, and independently C or N, 1A, 1B, 1C, and 1D are independently a substituted or unsubstituted C6 to C30 aryl group, or a substituted or unsubstituted C2 to C30 heterocyclic group, $L^A$, $L^B$, $L^C$, $L^D$, $Q^A$, $Q^B$, $Q^C$, and $Q^D$ are independently a single bond, O, S, a substituted or unsubstituted C1 to C30 alkylene group, a substituted or unsubstituted C2 to C30 alkenylene group, a substituted or unsubstituted C6 to C30 arylene group, or a substituted or unsubstituted C2 to C30 heteroarylene group, $R^A$, $R^B$, $R^C$, and $R^D$ are independently hydrogen, deuterium, a cyano group, a halogen, silane group, phosphine group, amine group, a substituted or unsubstituted C1 to C30 alkyl group, a substituted or unsubstituted C6 to C30 aryl group, or a substituted or unsubstituted C2 to C30 heteroaryl group, $R^A$, $R^B$, $R^C$, and $R^D$ are independently present or adjacent groups thereof are linked with each other to form a ring, n is one of integers of 0 to 5, and a, b, c, and d are independently one of integers of 0 to 3.

[Chemical Formula 4-2]

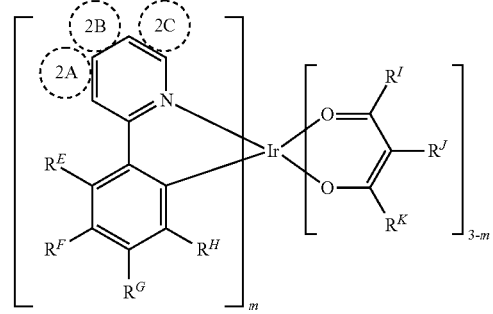

In Chemical Formula 4-2, 2A, 2B, and 2C are independently a substituted or unsubstituted benzene ring, at least one of 2A, 2B, and 2C forms a fused ring with an adjacent complex compound, $R^E$, $R^F$, $R^G$, $R^H$, $R^I$, $R^J$ and $R^K$ are independently hydrogen, deuterium, a cyano group, a halogen, a silane group, a phosphine group, an amine group, a substituted or unsubstituted C1 to C10 alkyl group, a substituted or unsubstituted C6 to C30 aryl group, or a substituted or unsubstituted C2 to C30 heteroaryl group, $R^E$, $R^F$, $R^G$, $R^H$, $R^I$, $R^J$, and $R^K$ are independently present or adjacent groups thereof are linked with each other to form a ring, and m is one of integers of 1 to 3.

In an example embodiment of the present invention, the platinum (Pt) complex may be represented by Chemical Formula 4-1a or Chemical Formula 4-1b.

[Chemical Formula 4-1a]

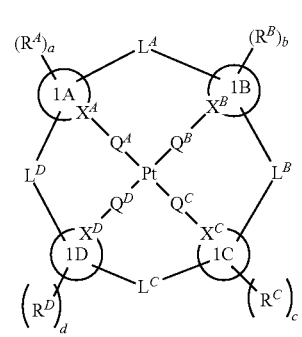

-continued

[Chemical Formula 4-1b]

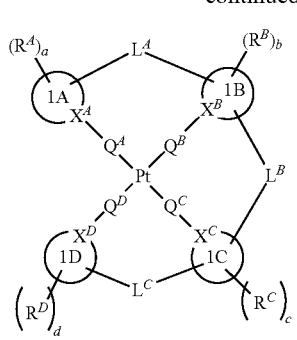

In Chemical Formula 4-1a and Chemical Formula 4-1b, definitions of $X^A$, $X^B$, $X^C$, $X^D$, 1A, 1B, 1C, 1D, $L^A$, $L^B$, $L^C$, $L^D$, $Q^A$, $Q^B$, $Q^C$, $Q^D$, $R^A$, $R^B$, $R^C$, $R^D$, a, b, c, and d are the same as described above.

In a specific example embodiment of the present invention, 1A, 1B, 1C, and 1D may independently be a substituted or unsubstituted C6 to C20 aryl group, or a substituted or unsubstituted C2 to C20 heterocyclic group, more specifically, a substituted or unsubstituted phenyl group, a substituted or unsubstituted naphthyl group, a substituted or unsubstituted anthracenyl group, a substituted or unsubstituted phenanthrenyl group, a substituted or unsubstituted triphenylenyl group, a substituted or unsubstituted pyridinyl group, a substituted or unsubstituted benzimidazolyl group, a substituted or unsubstituted benzothiazole group, a substituted or unsubstituted benzoxazole group, a substituted or unsubstituted pyrrolyl group, a substituted or unsubstituted pyrazolyl group, a substituted or unsubstituted imidazolyl group, a substituted or unsubstituted oxazolyl group, and may be for example selected from groups of Group IV, and groups of Group IV may be further substituted.

[Group IV]

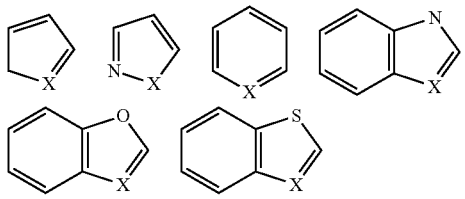

In Group IV, X is an element that forms an unsaturated ring with each of 1A, 1B, 1C, and 1 D, and independently C or N. Additional substituents may be deuterium, a cyano group, a halogen, a C1 to C10 alkyl group, or a C1 to C10 fluoroalkyl group.

More desirably, 1A, 1B, 1C, and 1D may be a substituted or unsubstituted phenyl group, a substituted or unsubstituted pyridinyl group, a substituted or unsubstituted benzimidazolyl group, a substituted or unsubstituted benzothiazole group, a substituted or unsubstituted pyrrolyl group, or a substituted or unsubstituted pyrazolyl group.

In a specific example embodiment of the present invention, when a, b, c and d are 2 or greater, each of substituents $R^A$, $R^B$, $R^C$ and $R^D$ may be the same or different.

Meanwhile, specific examples of the present invention include structures where adjacent groups of $R^A$, $R^B$, $R^C$, and $R^D$ are fused to form a ring. For example, Compound 3-5 or Compound 3-8 of Group 3 may be exemplified.

In an example embodiment of the present invention, the iridium (Ir) complex may be represented by Chemical Formula 4-2a, or Chemical Formula 4-2b.

[Chemical Formula 4-2a]

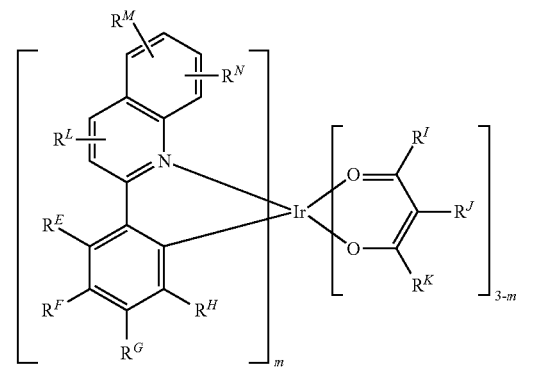

[Chemical Formula 4-2b]

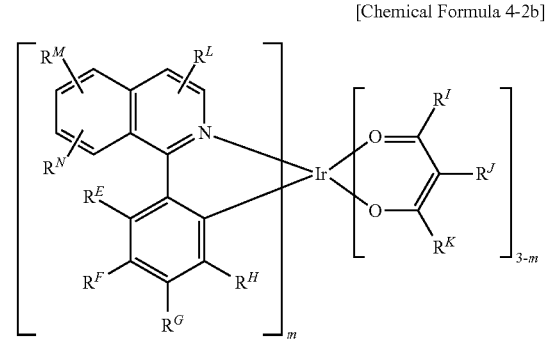

In Chemical Formula 4-2a and Chemical Formula 4-2b, definitions of $R^E$, $R^F$, $R^G$, $R^H$, $R^I$, $R^J$, $R^K$, and m are the same as described above, and definitions of $R^L$, $R^M$, and $R^N$ are the same as definitions of $R^E$, $R^F$, $R^G$, $R^H$, $R^I$, $R^J$, and $R^K$.

In a specific example embodiment of the present invention, $R^E$, $R^F$, $R^G$, $R^H$, $R^I$, $R^J$, $R^K$, $R^L$, $R^M$, and $R^N$ may be hydrogen, deuterium, a cyano group, a halogen, a C1 to C10 alkyl group, or a C1 to C10 fluoroalkyl group.

Meanwhile, specific examples of the present invention include structures where adjacent groups of $R^E$, $R^F$, $R^G$, and $R^H$ are fused to form a ring. For example, Compound 4-12 of Group 3 may be exemplified.

The phosphorescent dopant may be for example selected from compounds of Group 3, but is not limited thereto.

[Group 3]

[3-1]

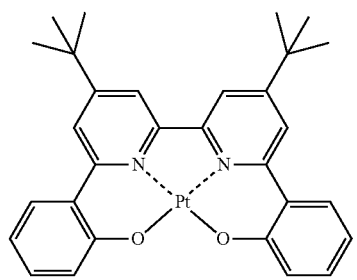

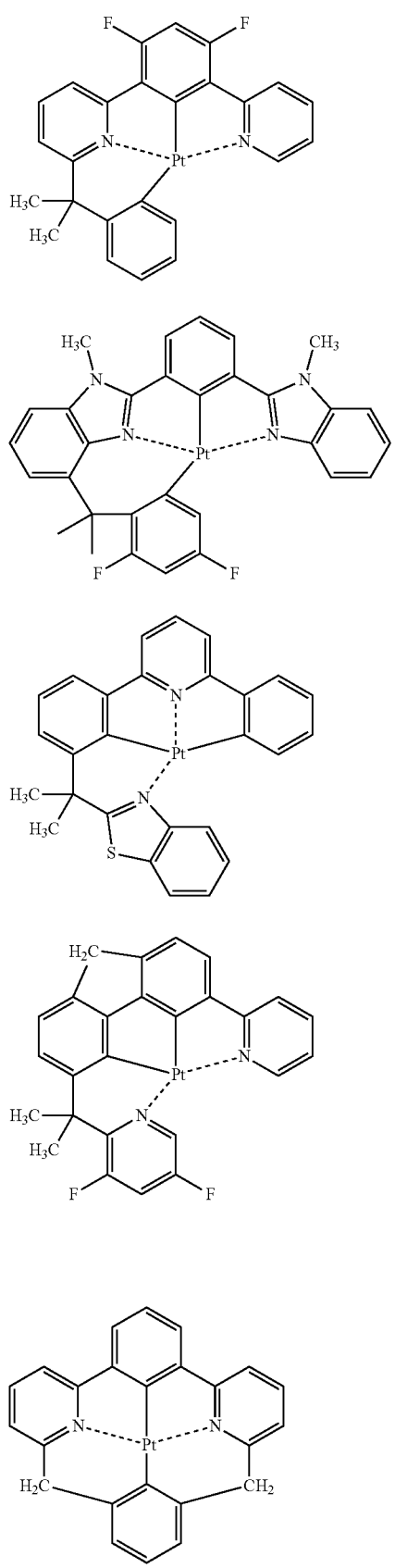
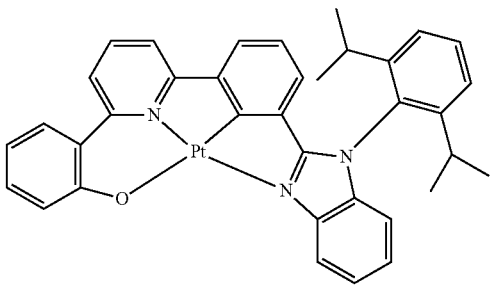
[3-2]
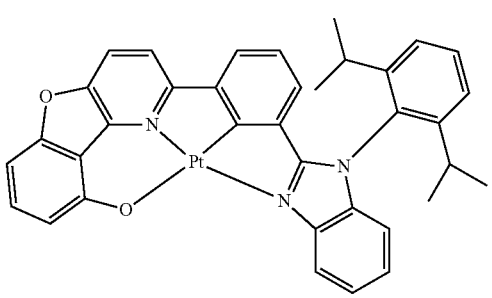
[3-7]
[3-3]
[3-8]
[3-4]
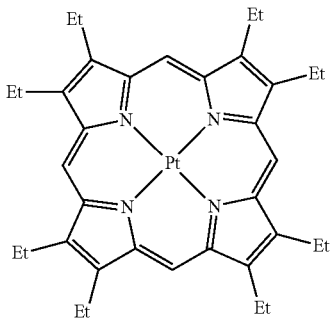
[3-9]
[3-5]
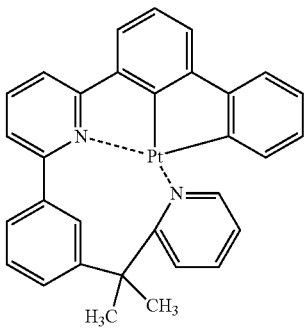
[3-10]
[3-6]
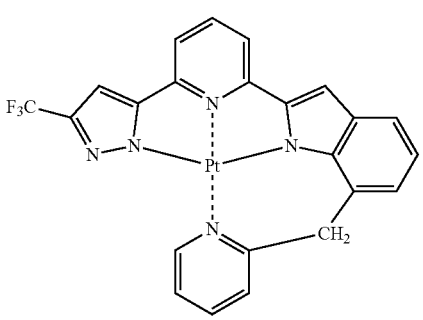
[3-11]

[4-1]
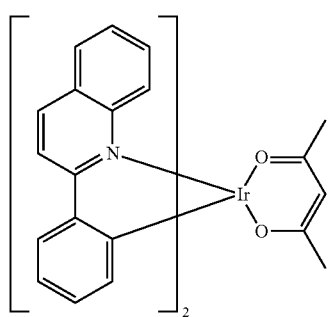
[4-2]
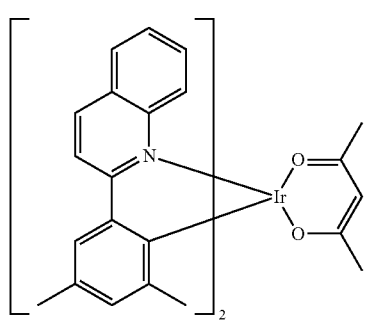
[4-3]
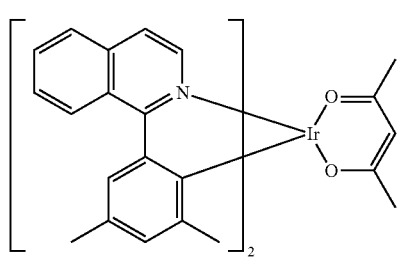
[4-4]
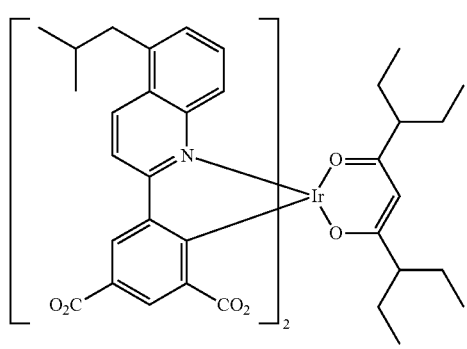
[4-5]
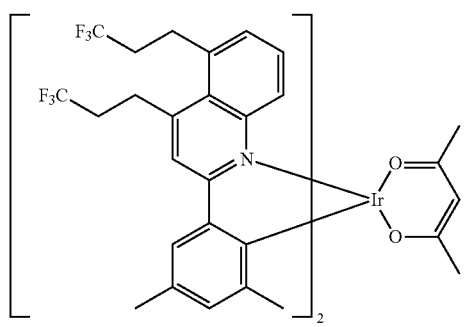
[4-6]
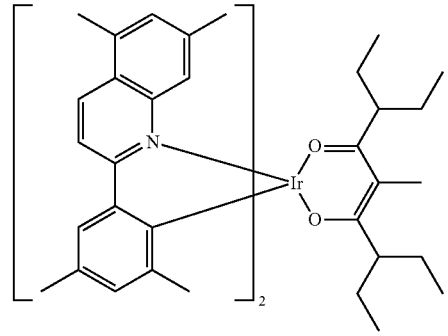
[4-7]
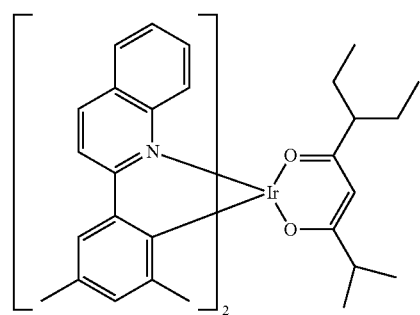
[4-8]
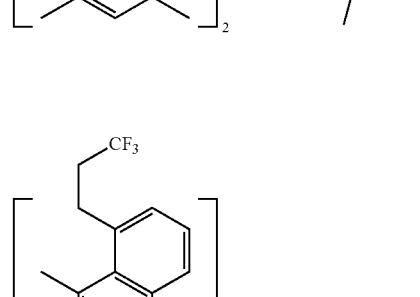
[4-9]
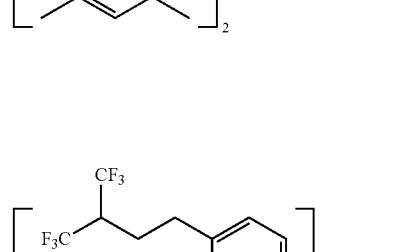

[4-10]
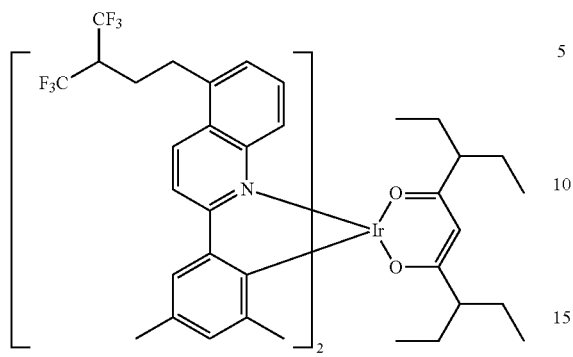
[4-13]
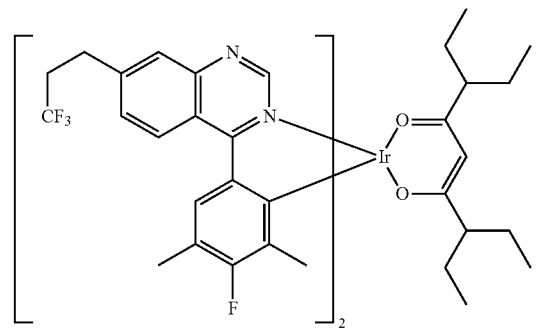
[4-11]
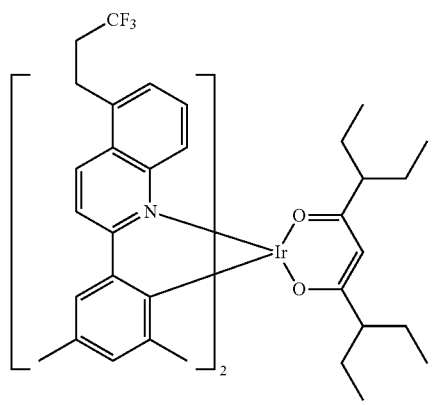
[4-14]
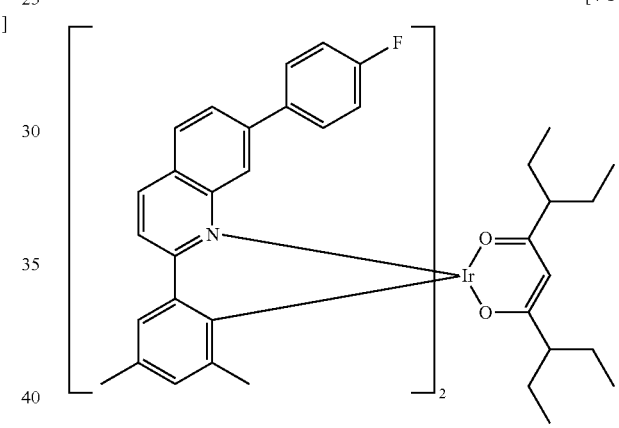
[4-12]
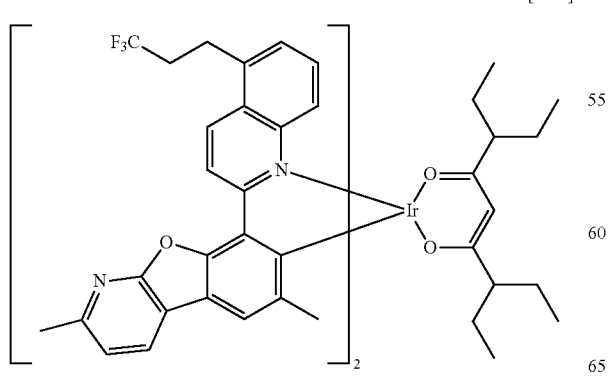
[4-15]
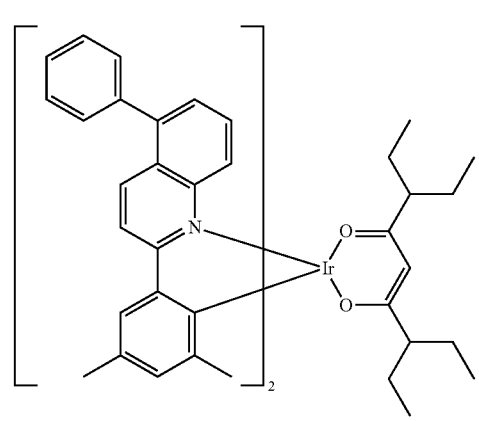

[4-16]
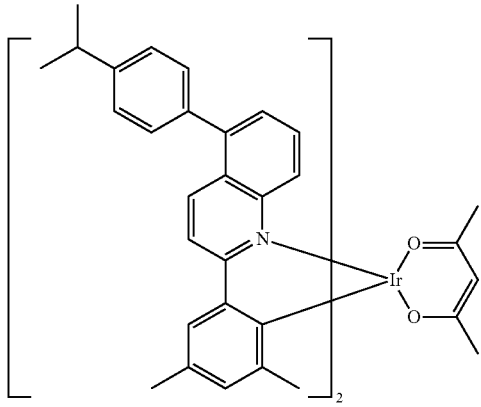

[4-17]
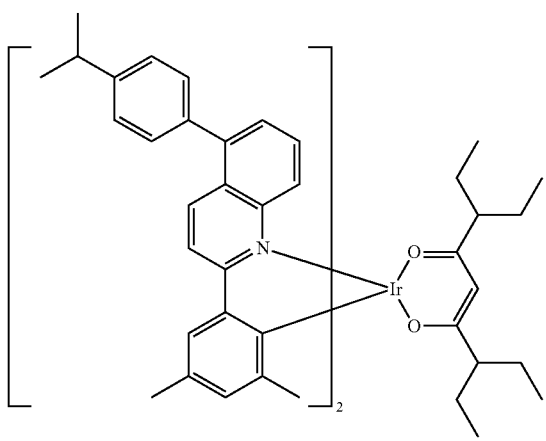

[4-18]
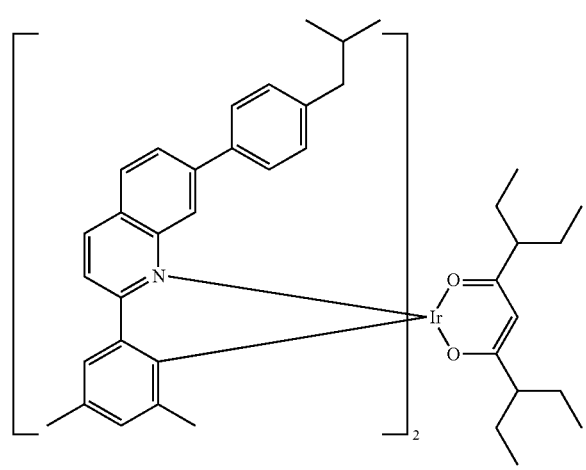

[4-19]
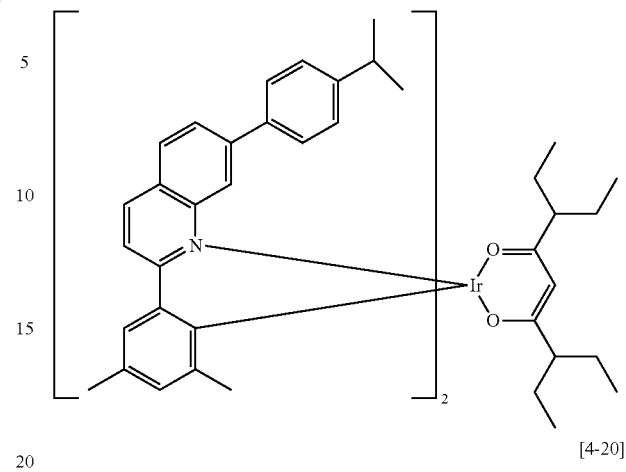

[4-20]
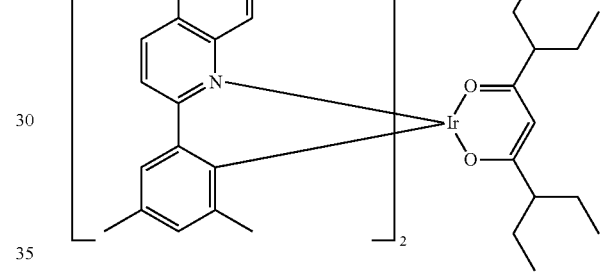

In the most specific example embodiment of the present invention, the phosphorescent dopant may be represented by Chemical Formula 4-2a.

More specifically, the phosphorescent dopant may be included in an amount of 0.1 to 50 wt % based on 100 wt % of the composition of the first compound for the organic optoelectronic device and the second compound for the organic optoelectronic device. The phosphorescent dopant may be included in an amount of 0.1 to 20 wt % based on 100 wt % of the composition of the first compound for the organic optoelectronic device and the second compound for the organic optoelectronic device. Most specifically, the phosphorescent dopant may be included in an amount of 0.5 to 10 wt % based on 100 wt % of the composition of the first compound for the organic optoelectronic device and the second compound for the organic optoelectronic device.

The composition may be formed by using a dry deposition method or a solution process such as chemical vapor deposition (CVD).

The aforementioned organic light emitting diode may be applied to an organic light emitting diode display.

Mode for Invention

Hereinafter, the embodiments are illustrated in more detail with reference to examples. These examples, however, are not in any sense to be interpreted as limiting the scope of the invention.

Hereinafter, starting materials and reactants used in Examples and Synthesis Examples were purchased from Sigma-Aldrich Co. Ltd. or TCI Inc. as far as there in no particular comment or were synthesized by known methods.

(Preparation of Compound for Organic Optoelectronic Device)

The compound as one specific examples of the present invention was synthesized through the following steps.

(First Compound for Organic Optoelectronic Device)

Synthesis Example 1

Synthesis of Compound A-1

First Step: Synthesis of 4-bromo-2-fluoro-1-(2-methoxyphenyl)benzene 2-methoxyphenylboronic acid (50.0 g, 329 mmol), 4-bromo-2-fluoro-1-iodobenzene (99.0 g, 329 mmol), tetrakis(triphenylphosphine)palladium (0) (19.0 g, 16 mmol), and potassium carbonate (113.7 g, 823 mmol) were dissolved in 2 L of a mixed solution of tetrahydrofuran: DIW=2:1 and then, refluxed and stirred at 80° C. for 12 hours. When a reaction was complete, 4-bromo-2-fluoro-1-(2-methoxyphenyl)benzene (78.0 g, Y=84.3%) was obtained by extracting an organic layer, evaporating all the solvents,

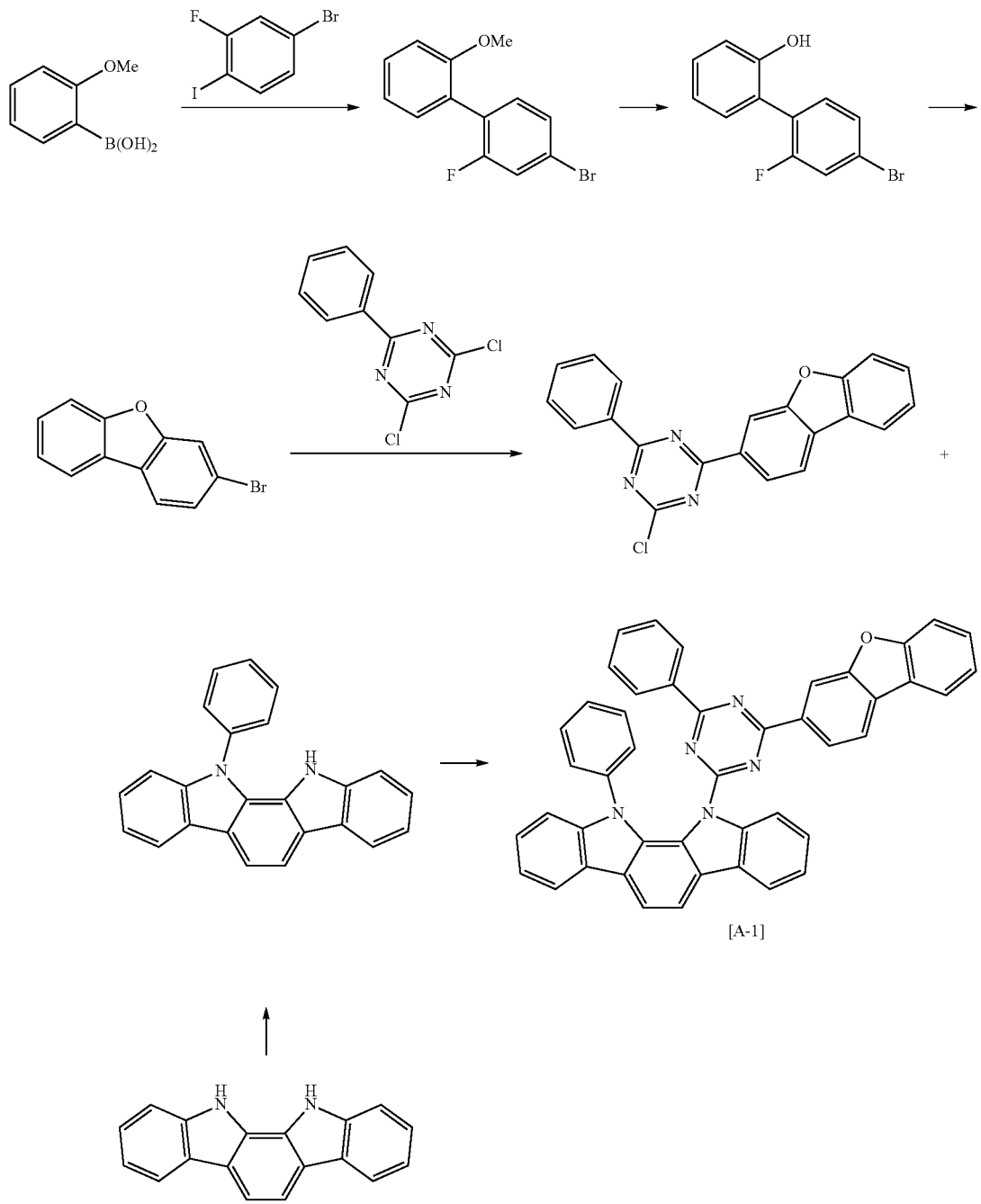

[Reaction Scheme 1]

[A-1]

and then, purifying the residue through column chromatography with a mixed solution of dichloromethane:n-hexane.

Second Step: Synthesis of 4-bromo-2-fluoro-1-(2-hydroxyphenyl)benzene 4-bromo-2-fluoro-1-(2-methoxyphenyl)benzene (78.0 g, 277 mmol) was dissolved in 500 mL dichloromethane, and then, 694 mL of a 1 M tribromoboron solution is dripped thereinto at 0° C. The mixture was stirred at room temperature under a nitrogen flow. When a reaction was complete, the solution was dripped into water and twice extracted with ethyl acetate. The organic layer was purified through column chromatography with a mixed solution of n-hexane:dichloromethane to obtain 4-bromo-2-fluoro-1-(2-hydroxyphenyl)benzene (70.2 g, Y=94.7%).

Third Step: Synthesis of 3-bromodibenzofuran 4-bromo-2-fluoro-1-(2-hydroxyphenyl)benzene (70.0 g, 262 mmol) and potassium carbonate (72.5 g, 524 mmol) was dissolved in 800 mL of N-methyl-2-pyrrolidone and then, stirred under a nitrogen flow at 130° C. for 3 hours. When a reaction was complete, the solvents were all evaporated and then, once extracted with dichloromethane and water. After removing the dichloromethane, slurry obtained therefrom was purified with methyl alcohol to obtain 3-bromodibenzofuran (57.4 g, Y=88.6%).

Fourth Step: Synthesis of 2-chloro-4-dibenzofuran-3-yl-6-phenyl-1,3,5-triazine 2-chloro-4-dibenzofuran-3-yl-6-phenyl-1,3,5-triazine (Y=48.3%) was synthesized according to the same method as the first step by using 2,4-dichloro-6-phenyl-1,3,5-triazine and 3-bromodibenzofuran as a starting material.

Fifth Step: Synthesis of 12-phenyl-11H-indolo[2,3-a]carbazole

Indolo[2,3-a]carbazole (20.0 g, 78 mmol), bromobenzene (12.3 g, 78 mmol), copper(I) iodide (2.97 g, 16 mmol), potassium carbonate (16.2 g, 117 mmol), and 1,10-phenanthroline (2.8 g, 16 mmol) were put in 260 mL of N,N-dimethylformamide and then, refluxed and stirred under a nitrogen flow for 12 hours. When a reaction was complete, after all evaporating the solvents, the residue thereof was dissolved in toluene and silica gel-filtered. The filtered solution was recrystallized to obtain 12-phenyl-11H-indolo[2,3-a]carbazole (19.6 g, Y=76%).

Sixth Step: Synthesis of Compound A-1

12-phenyl-11H-indolo[2,3-a]carbazole (10.0 g, 28 mmol) and 2-chloro-4-dibenzofuran-3-yl-6-phenyl-1,3,5-triazine (18.6 g, 56 mmol) were put in 100 mL of N,N-dimethylformamide and then, cooled down to 0° C. After 10 minutes, sodium hydride (1.34 g, 56 mmol) was added thereto and then, stirred under a nitrogen flow for 12 hours at room temperature. When a reaction was complete, after all evaporating the solvents, the residue thereof was dissolved in chlorobenzene and then, silica gel-filtered. The filtered solution was recrystallized to obtain Compound A-1 (16.5 g, Y=90%).

Synthesis Example 2

Synthesis of Compound A-74

[Reaction Scheme 2]

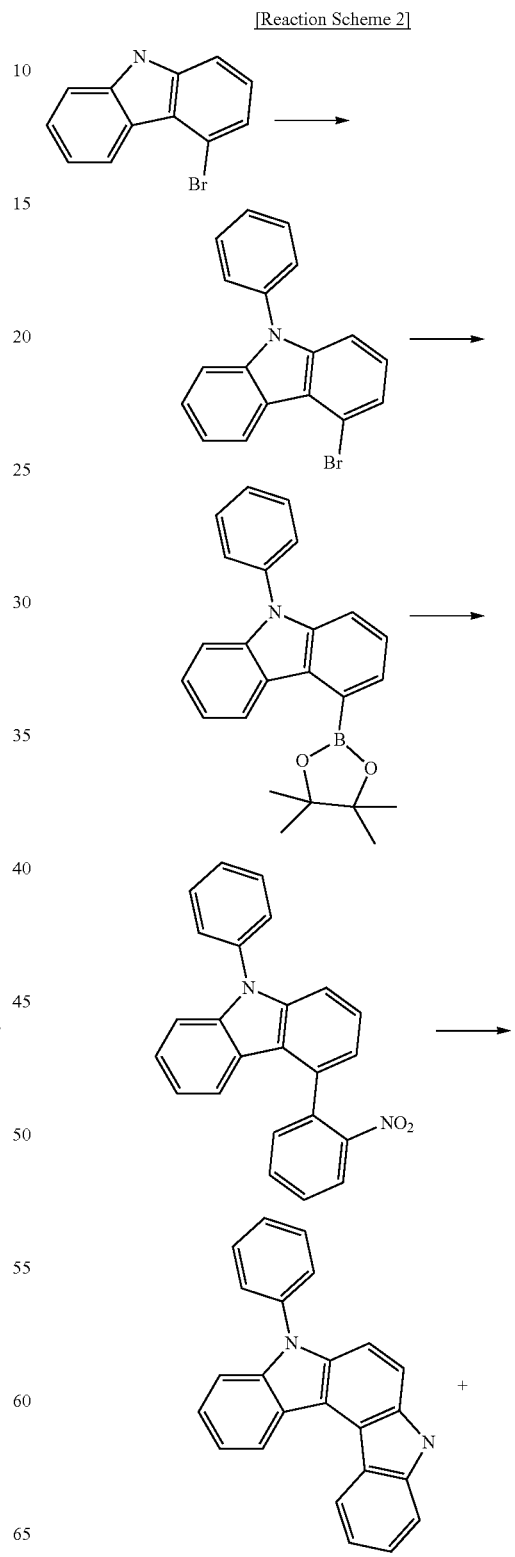

-continued

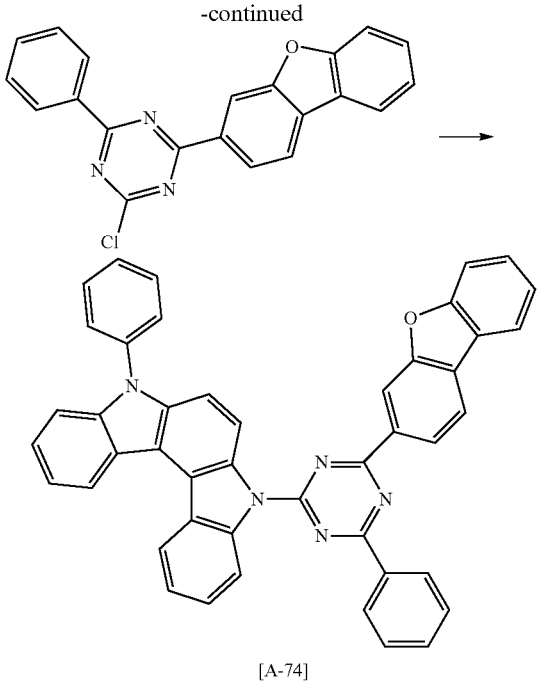

[A-74]

First Step: Synthesis of 4-bromo-9-phenyl-carbazole 4-bromo-9H-carbazole as a starting material was used to perform a synthesis according to the same method as the fifth step of Synthesis Example 1, and a mixed solution of n-hexane:dichloromethane was used for the column chromatography purification. (Y=72%)

Second Step: Synthesis of 9-phenyl-4-(4,4,5,5-tetramethyl-1,3,2-dioxaborolan-2-yl)carbazole 4-bromo-9-phenyl-carbazole (30.0 g, 93 mmol), bis(pinacolato)diboron (35.5 g, 140 mmol), potassium acetate (27.4 g, 279 mmol), and [1,1'-bis(diphenylphosphino)ferrocene]-dichloropalladium(II) (3.0 g, 4 mmol) were added to 450 mL of N,N-dimethylformamide and then, refluxed and stirred at 150° C. for 12 hours. When a reaction was complete, the solution was added to an excessive amount of DIW to form precipitates. The precipitates were filtered and then, boiled and dissolved in toluene and silica gel-filtered After all evaporating the solvents of the filtered solution, the residue thereof was recrystallized with a mixed solution of dichloromethane:n-hexane to obtain 9-phenyl-4-(4,4,5,5-tetramethyl-1,3,2-dioxaborolan-2-yl)carbazole (29.2 g, Y=84.9%).

Third Step: Synthesis of 4-(2-nitrophenyl)-9-phenyl-carbazole 9-phenyl-4-(4,4,5,5-tetramethyl-1,3,2-dioxaborolan-2-yl)carbazole and 1-bromo-2-nitrobenzene as a starting material were used to perform a synthesis according to the same method as the first step of Synthesis Example 1, and a mixed solution of n-hexane:dichloromethane were used for recrystallization to obtain 4-(2-nitrophenyl)-9-phenyl-carbazole. (Y=82%)

Fourth Step: Synthesis of 5-phenyl-5,8-dihydroindolo[2,3-c]carbazole 4-(2-nitrophenyl)-9-phenyl-carbazole (20.0 g, 55 mmol) and triphenylphosphine (28.8 g, 110 mmol) were put in 1,2-dichlorobenzene and then, stirred under a nitrogen flow at 180° C. for 12 hours. When a reaction was complete, the solvent was all evaporated, and a mixed solution of n-hexane:dichloromethane was used for the column chromatography purification to obtain 5-phenyl-5,8-dihydroindolo[2,3-c]carbazole (11 g, Y=60.3%).

Calcd. C18H12N2: C, 86.72; H, 4.85; N, 8.43. Found: C, 86.70; H, 4.83; N, 8.47.

Fifth Step: Synthesis of Compound A-74

5-phenyl-5,8-dihydroindolo[2,3-c]carbazole and 2-chloro-4-dibenzofuran-3-yl-6-phenyl-1,3,5-triazine as a starting material were used to perform a synthesis according to the same method as the sixth step of Synthesis Example 1 to obtain Compound A-74. (Y=70%)

Second Compound for Organic Optoelectronic Device

Synthesis Example 3

Synthesis of Compound B-1

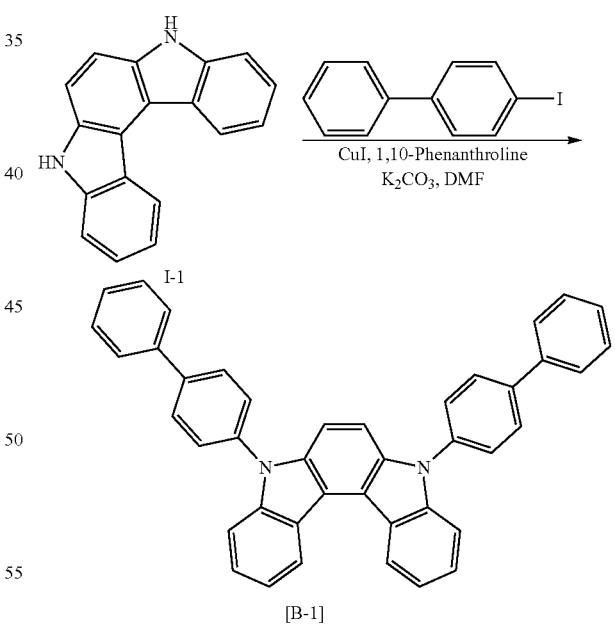

[B-1]

8 g (31.2 mmol) of Intermediate I-1, 20.5 g (73.32 mmol) of 4-iodobiphenyl, 1.19 g (6.24 mmol) of CuI, 1.12 g (6.24 mmol) of 1,10-phenanthoroline, and 12.9 g (93.6 mmol) of K$_2$CO$_3$ were put in a round-bottomed flask, 50 ml of DMF was added thereto, and the mixture was refluxed and stirred under a nitrogen atmosphere for 24 hours. When a reaction was complete, distilled water was added thereto for a precipitation, and a solid obtained therefrom was filtered. The solid was dissolved in 250 ml of xylene, filtered with silica gel, and precipitated into a white solid to obtain the target compound B-1 (16.2 g, Y=93%).

Synthesis Example 4

Synthesis of Compound B-2

Reaction Scheme 4

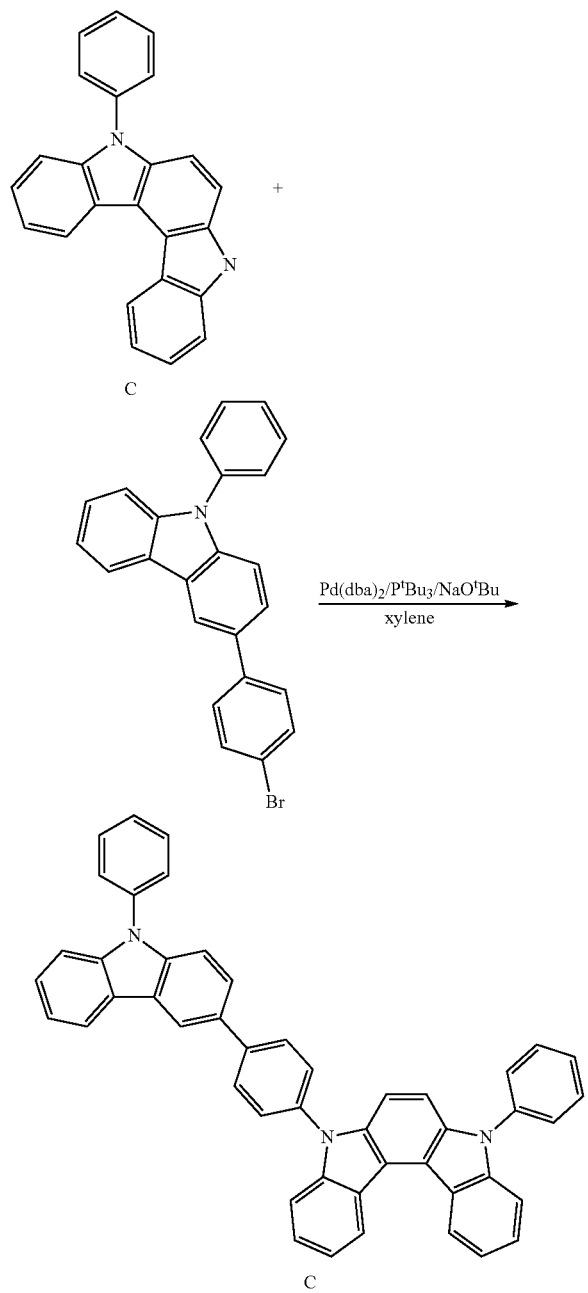

10.0 g (30.2 mmol) of 5-phenyl-5,8-dihydroindolo[2,3-c]carbazole synthesized in the fourth step of Synthesis Example 2, 14.4 g (36.2 mmol) of 3-(4-bromophenyl)-9-phenyl-9Hcarbazole, 4.3 g (45.3 mmol) of sodium t-butoxide (NaOtBu), 1.0 g (1.8 mmol) of Pd(dba)$_2$, and 2.2 g (50% in toluene) of tri t-butylphosphine (P(tBu)$_3$) were put in 150 mL of xylene in a 500 mL flask and then, heated and refluxed under a nitrogen flow for 12 hours. After removing the xylene, 200 mL of methanol was added to a mixture obtained therefrom, a solid crystallized therein was filtered, dissolved in dichloromethane, filtered with silica gel/Celite, and after removing an appropriate amount of the organic solvent, recrystallized with acetone to obtain Compound B-2 (15.0 g, yield of 77%).

calcd. C47H30N4S:C, 88.72; H, 4.81; N, 6.47. Found: C, 88.74; H, 4.82; N, 6.44.

Comparative Synthesis Example 1

Synthesis of Compound ET1

Compound ET1 was synthesized with reference to a synthesis method described in KR0955993B1.

Comparative Synthesis Example 2

Synthesis of Compound ET2

Compound ET2 was synthesized with reference to a synthesis method described in KR1477613B1.

Comparative Synthesis Example 3

Synthesis of Compound HT1

Compound HT1 was synthesized with reference to a synthesis method described in JP3139321B2.

Comparative Synthesis Example 4

Synthesis of Compound HT2

Compound HT2 was synthesized with reference to a synthesis method described in KR2011-068330A.

Comparative Synthesis Example 5

Synthesis of Compound HT3

Compound HT3 was synthesized with reference to a synthesis method described in KR2015-0003658A.

Comparative Synthesis Example 6

Synthesis of Compound HT4

Compound HT4 was synthesized with reference to a synthesis method described in KR2015-0003658A.

Comparative Synthesis Example 7

Synthesis of Compound HT5

Compound HT5 was synthesized with reference to a synthesis method described in KR2016-0126698A.

Comparative Synthesis Example 8

Synthesis of Compound HT6

Compound HT6 was synthesized with reference to a synthesis method described in KR1477613B1.

Comparative Synthesis Example 9
Synthesis of Compound HT7
Compound HT7 was synthesized with reference to a synthesis method described in KR1477613B1.
[ET1]
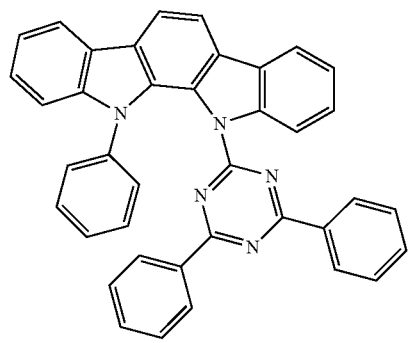
[ET2]
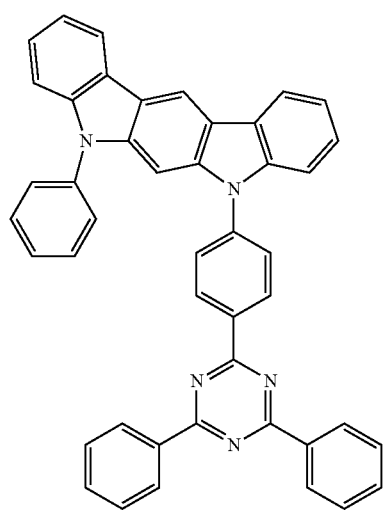
[HT1]
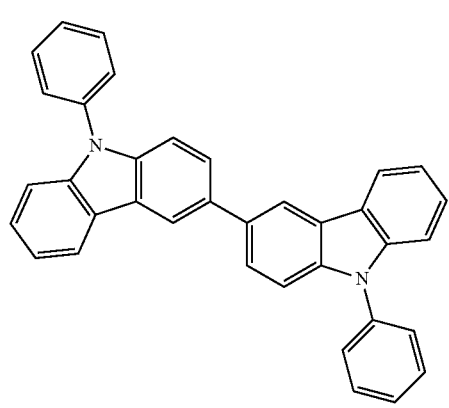
[HT2]
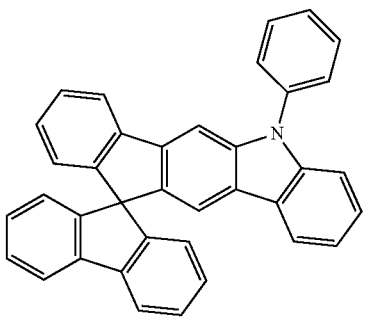
[HT3]
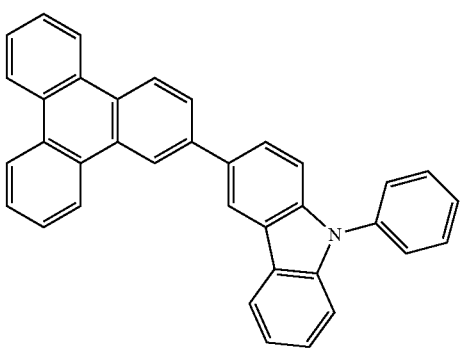
[HT4]
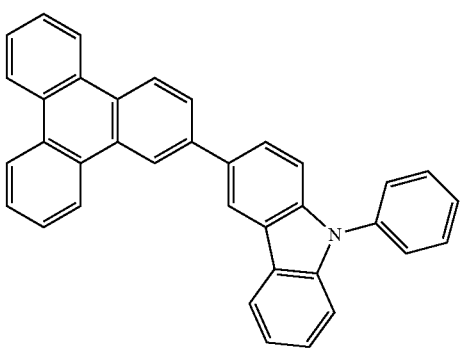
[HT5]
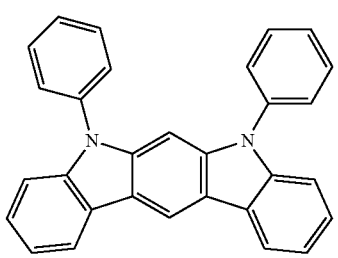

-continued

[HT6]
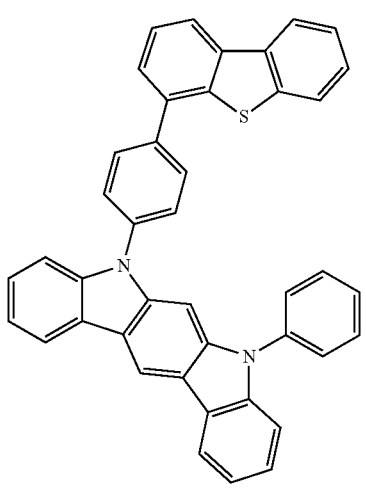

[HT7]
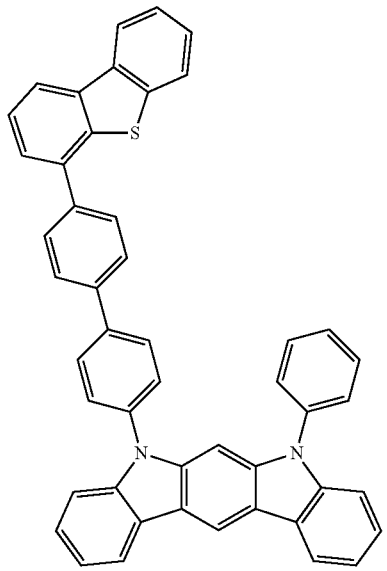

(Manufacture of Organic Light Emitting Diode)

Example 1

A glass substrate coated with ITO (indium tin oxide) as a 1500 Å-thick thin film was washed with distilled water. After washing with the distilled water, the glass substrate was ultrasonic wave-washed with a solvent such as isopropyl alcohol, acetone, methanol, and the like and dried and then, moved to a plasma cleaner, cleaned by using oxygen plasma for 10 minutes, and moved to a vacuum depositor. This obtained ITO transparent electrode was used as an anode, Compound A was vacuum-deposited on the ITO substrate to form a 700 Å-thick hole injection layer, Compound B was deposited to be 50 Å thick on the injection layer, and Compound C was deposited to be 1020 Å thick to form a hole transport layer. A 400 Å-thick light emitting layer was formed on the hole transport layer by vacuum-depositing Compound A-1 and Compound B-1 simultaneously as hosts and 5 wt % of [Ir(piq)$_2$acac] as a dopant. Herein, Compound A-1 and Compound B-1 were used in a 3:7 ratio and their ratios of the following examples were separately described. Subsequently, Compound D and Liq were vacuum-deposited simultaneously at a 1:1 ratio on the light emitting layer to form a 300 Å-thick electron transport layer and a cathode was formed by sequentially vacuum-depositing Liq to be 15 Å thick and Al to be 1200 Å thick on the electron transport layer, manufacturing an organic light emitting diode.

The organic light emitting diode had a five-layered organic thin layer structure, and specifically A structure of ITO/Compound A (700 Å)/Compound B (50 Å)/Compound C (1020 Å)/EML[Compound A-1: Compound B-1: [Ir(piq)$_2$acac]=27 wt %:63 wt %:5 wt %] (400 Å)/Compound D:Liq (300 Å)/Liq (15 Å)/Al (1200 Å).

Compound A: N4,N4'-diphenyl-N4,N4'-bis(9-phenyl-9H-carbazol-3-yl)biphenyl-4,4'-diamine, Compound B: 1,4,5,8,9,11-hexaazatriphenylene-hexacarbonitrile (HAT-CN), Compound C: N-(biphenyl-4-yl)-9,9-dimethyl-N-(4-(9-phenyl-9H-carbazol-3-yl)phenyl)-9H-fluoren-2-amine, and Compound D: 8-(4-(4,6-di(naphthalen-2-yl)-1,3,5-triazin-2-yl)phenyl)quinolone.

Examples 2 to 9 and Comparative Examples 1 to 7

Organic light emitting diodes according to Example 2 to Example 7 and Comparative Example 1 to 7 were respectively manufactured according to the same method as Example 1 by using the first and second hosts of the present invention as shown in Table 1 respectively.

Evaluation

Luminous efficiency and driving voltages of each organic light emitting diode according to Examples 1 to 7 and Comparative Examples 1 to 7 were evaluated.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

(4) Measurement of Driving Voltage

Driving voltages of each device was measured at 15 mA/cm$^2$ by using a current-voltage meter (Keithley 2400) to obtain the results.

(5) Measurement of Life-Span

T97 life-spans of the organic light emitting diodes according to Examples 1 to 9 and Comparative Examples 1 to Comparative Example 7 were measured as a time when their luminance decreased down to 97% relative to the initial luminance (cd/m$^2$) after emitting light with 6000 cd/m$^2$ as the initial luminance (cd/m$^2$) and measuring their luminance decrease depending on a time with a Polanonix life-span measurement system.

(6) Measurement of HOD (@7V) Current Density

As for HOD (Hole Only Device), an organic light emitting diode having a structure of two organic thin layers, a current flowing in a unit device was measured by using a current-voltage meter (Keithley 2400), while a voltage was increased from −6 V to 8 V, and the current value measured at 7 V was divided by an area to provide the following current density results.

Structure of HOD (Hole Only Device)

ITO/compound C (500 Å)/second host (400 Å)/Al (1200 Å)

TABLE 1

| Examples | First host | Second host | First host:Second host (wt:wt) | Color | Current density of second host HOD (@7 V) (mA/cm$^2$) | Δ HOMO (eV) | Life-span T97 | Luminous efficiency (cd/A) | Driving voltage (V) |
|---|---|---|---|---|---|---|---|---|---|
| Ex. 1 | Compound A-1 | Compound B-1 | 50:50 | red | 2248 | 0.24 | 141 | 18.5 | 3.35 |
| Ex. 2 | Compound A-1 | Compound B-1 | 40:60 | red | 2248 | 0.24 | 157 | 18.3 | 3.74 |
| Ex. 3 | Compound A-74 | Compound B-1 | 50:50 | red | 2248 | 0.24 | 106 | 21.5 | 3.52 |
| Ex. 4 | Compound A-74 | Compound B-1 | 40:60 | red | 2248 | 0.24 | 145 | 19.9 | 3.74 |
| Ex. 5 | Compound A-74 | Compound B-1 | 30:70 | red | 2248 | 0.24 | 89 | 18.1 | 3.80 |
| Ex. 6 | Compound A-1 | Compound B-2 | 50:50 | red | 2165 | 0.27 | 80 | 18.5 | 3.57 |
| Ex. 7 | Compound A-74 | Compound B-2 | 50:50 | red | 2165 | 0.28 | 71 | 20.3 | 3.69 |
| Comp. Ex. 1 | ET1 | HT1 | 50:50 | red | 1117 | 0.13 | 34 | 15.2 | 4.14 |
| Comp. Ex. 2 | ET1 | HT2 | 50:50 | red | 1325 | 0.15 | 11 | 16.7 | 4.02 |
| Comp. Ex. 3 | ET1 | HT3 | 50:50 | red | 877 | 0.09 | 19 | 16.3 | 4.23 |
| Comp. Ex. 4 | ET1 | HT4 | 50:50 | red | 633 | 0.04 | 17 | 17.5 | 4.29 |
| Comp. Ex. 5 | ET2 | HT5 | 50:50 | red | 874 | 0.31 | 2 | 15.9 | 3.91 |
| Comp. Ex. 6 | ET2 | HT6 | 50:50 | red | 938 | 0.33 | 5 | 16.4 | 3.82 |
| Comp. Ex. 7 | ET2 | HT7 | 50:50 | red | 958 | 0.33 | 6 | 16.1 | 3.84 |

* Life-spans of devices having luminance lower than 6000 cd/m$^2$ are not measurable Referring to Table 1, when the first compound for the organic optoelectronic device and the second compound for the organic optoelectronic device were combined to prepare a host, the organic light emitting diodes using the same according to Examples exhibited equivalent or deteriorated driving voltage or improved efficiency and life-span compared with those of Comparative Examples.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

The invention claimed is:
1. An organic optoelectronic device comprising
an anode and a cathode facing each other, and
at least one organic layer disposed between the anode and the cathode, wherein the organic layer comprises a composition for an organic optoelectronic device comprising a first compound for an organic optoelectronic device represented by a combination of Chemical Formula 1 and Chemical Formula 2 and a second compound for an organic optoelectronic device represented by Chemical Formula 3; and a dopant having a maximum emission wavelength of 570 nm to 750 nm:

[Chemical Formula 1]

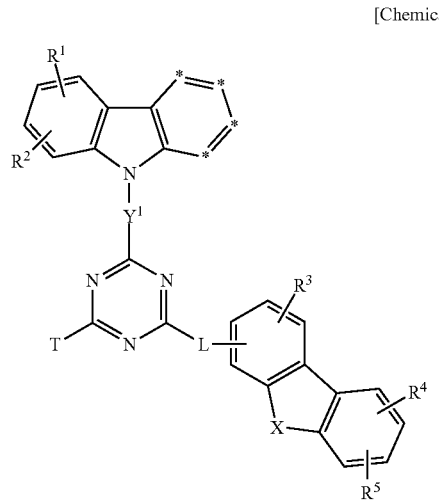

-continued

[Chemical Formula 2]

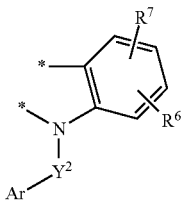

[Chemical Formula 3]

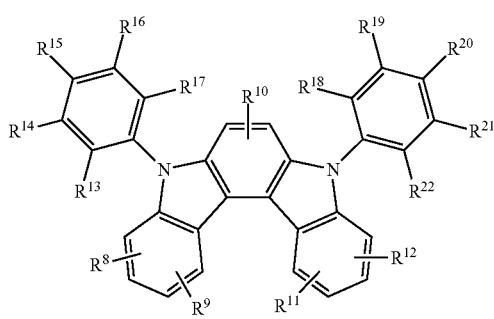

wherein, in Chemical Formula 1 to Chemical Formula 3,
X is O or S,
T is a substituted or unsubstituted C6 to C18 aryl group, a substituted or unsubstituted dibenzofuranyl group, or a substituted or unsubstituted dibenzothiophenyl group,
Ar is a substituted or unsubstituted C6 to C30 aryl group,
L, $Y^1$, and $Y^2$ are independently a single bond, or a substituted or unsubstituted C6 to C20 arylene group,
adjacent two *'s of Chemical Formula 1 are linked to *'s of Chemical Formula 2,
in Chemical Formula 1, *'s that are not linked to *'s of Chemical Formula 2 are independently $CR^a$,
$R^a$ and $R^1$ to $R^{12}$ are independently hydrogen, deuterium, a cyano group, a substituted or unsubstituted C1 to C20 alkyl group, or a substituted or unsubstituted C6 to C18 aryl group,
$R^{13}$ to $R^{22}$ are independently hydrogen, deuterium, a cyano group, an amino group, a substituted or unsubstituted C1 to C20 alkyl group, a substituted or unsubstituted C2 to C20 alkenyl group, a substituted or unsubstituted C6 to C18 aryl group, or a substituted or unsubstituted carbazolyl group,
$R^{13}$ to $R^{22}$ are independently present or adjacent groups thereof are linked to each other to form a substituted or unsubstituted aromatic ring or a substituted or unsubstituted heteroaromatic ring, and
when $R^{13}$ to $R^{22}$ are independently present, at least one of $R^{13}$ to $R^{22}$ is a substituted or unsubstituted C6 to C18 aryl group, or a substituted or unsubstituted carbazolyl group.

2. The organic optoelectronic device of claim 1, wherein the second compound for the organic optoelectronic device has a current density measured at a voltage of 7 V of 1500 mA/cm² to 2500 mA/cm² in the following HOD (Hole Only Device):
ITO/Compound C (500 Å)/second compound for an organic optoelectronic device (400 Å)/Al (1200 Å);
Compound C: N-(biphenyl-4-yl)-9,9-dimethyl-N-(4-(9-phenyl-9H-carbazol-3-yl)phenyl)-9H-fluoren-2-amine.

3. The organic optoelectronic device of claim 1, wherein a difference between HOMO energy levels of the first compound for the organic optoelectronic device and the second compound for the organic optoelectronic device is 0.2 eV to 0.5 eV.

4. The organic optoelectronic device of claim 1, wherein a maximum emission wavelength of the mixture of the first compound for the organic optoelectronic device and the second compound for the organic optoelectronic device is 450 nm to 550 nm.

5. The organic optoelectronic device of claim 1, wherein the first compound for the organic optoelectronic device is represented by Chemical Formula 1B or Chemical Formula 1C:

[Chemical Formula 1B]

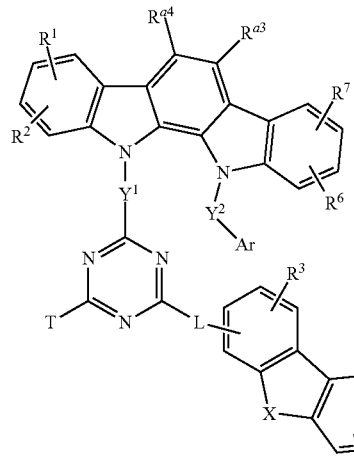

[Chemical Formula 1C]

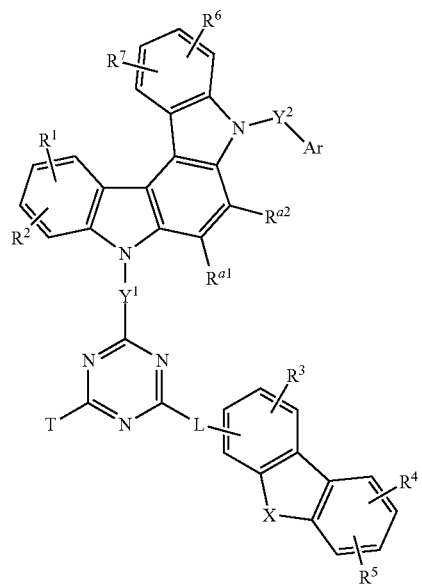

wherein, in Chemical Formula 1B and Chemical Formula 1C,
X is O or S,
T is a substituted or unsubstituted C6 to C18 aryl group, a substituted or unsubstituted dibenzofuranyl group, or a substituted or unsubstituted dibenzothiophenyl group,
Ar is a substituted or unsubstituted C6 to C30 aryl group,
L, $Y^1$ and $Y^2$ are independently a single bond, or a substituted or unsubstituted C6 to C20 arylene group, and
$R^{a1}$ to $R^{a4}$ and $R^1$ to $R^7$ are independently hydrogen, deuterium, a cyano group, a substituted or unsubstituted C1 to C20 alkyl group, or a substituted or unsubstituted C6 to C18 aryl group.

6. The organic optoelectronic device of claim 5, wherein Chemical Formula 1B is represented by Chemical Formula 1B-2 or Chemical Formula 1B-3:

[Chemical Formula 1B-2]

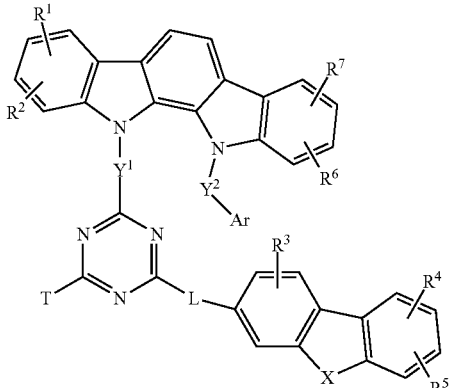

[Chemical Formula 1B-3]

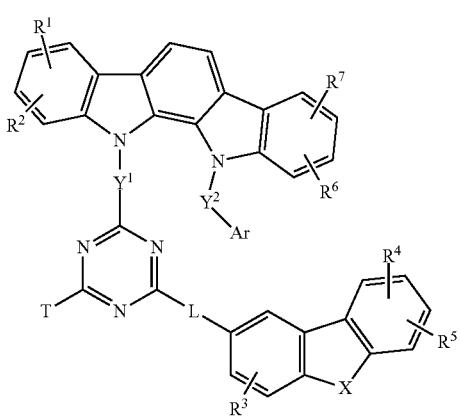

wherein, in Chemical Formula 1B-2 and Chemical Formula 1B-3,

X is O or S,

T is a substituted or unsubstituted C6 to C18 aryl group, a substituted or unsubstituted dibenzofuranyl group, or a substituted or unsubstituted dibenzothiophenyl group, Ar is a substituted or unsubstituted C6 to C30 aryl group, L, $Y^1$, and $Y^2$ are independently a single bond, or a substituted or unsubstituted C6 to C20 arylene group, and $R^1$ to $R^7$ are independently hydrogen, deuterium, a cyano group, a substituted or unsubstituted C1 to C20 alkyl group, or a substituted or unsubstituted C6 to C18 aryl group.

7. The organic optoelectronic device of claim 5, wherein Chemical Formula 1C is represented by Chemical Formula 1C-2 or Chemical Formula 1C-3:

[Chemical Formula 1C-2]

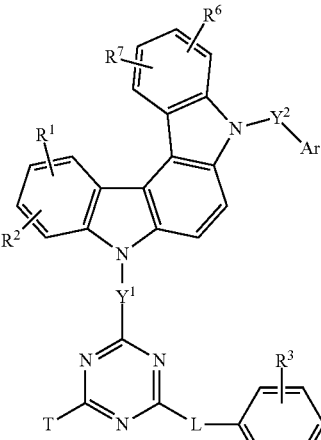

[Chemical Formula 1C-3]

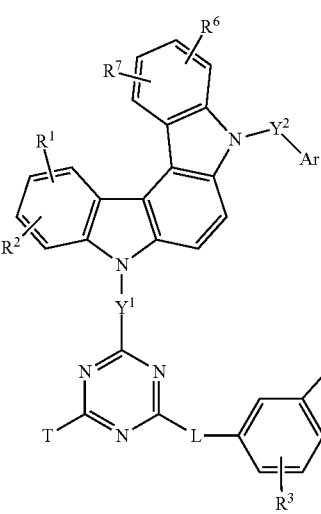

wherein, in Chemical Formula 1C-2 and Chemical Formula 1C-3,

X is O or S,

T is a substituted or unsubstituted C6 to C18 aryl group, a substituted or unsubstituted dibenzofuranyl group, or a substituted or unsubstituted dibenzothiophenyl group, Ar is a substituted or unsubstituted C6 to C30 aryl group, L, $Y^1$, and $Y^2$ are independently a single bond, or a substituted or unsubstituted C6 to C20 arylene group, and $R^1$ to $R^7$ are independently hydrogen, deuterium, a cyano group, a substituted or unsubstituted C1 to C20 alkyl group, or a substituted or unsubstituted C6 to C18 aryl group.

8. The organic optoelectronic device of claim 1, wherein T is a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, or a substituted or unsubstituted dibenzothiophenyl group, Ar is a substituted or unsubstituted phenyl group, a substituted or unsubstituted biphenyl group, a substituted or unsubstituted naphthyl group, or a substituted or unsubstituted terphenyl group, L, $Y^1$, and $Y^2$ are independently a single bond, a substituted or unsubstituted phenylene group, or a substituted or unsubstituted biphenylene group, and $R^1$ to $R^7$ are independently hydrogen, a substituted or unsubstituted C1 to C5 alkyl group, or a substituted or unsubstituted phenyl group of organic optoelectronic device.

9. The organic optoelectronic device of claim 1, wherein the second compound for the organic optoelectronic device is represented by Chemical Formula 3A-1:

[Chemical Formula 3A-1]

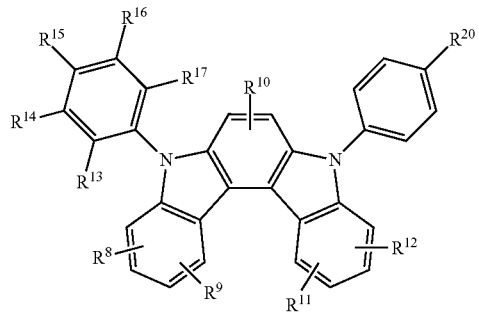

wherein, in Chemical Formula 3A-1, $R^8$ to $R^{12}$ are independently hydrogen, deuterium, a cyano group, a substituted or unsubstituted C1 to C20 alkyl group, or a substituted or unsubstituted C6 to C18 aryl group, $R^{13}$ to $R^{17}$ are independently hydrogen, deuterium, a cyano group, an amino group, a substituted or unsubstituted C1 to C20 alkyl group, a substituted or unsubstituted C2 to C20 alkenyl group, a substituted or unsubstituted C6 to C18 aryl group, or a substituted or unsubstituted carbazolyl group, $R^{13}$ to $R^{17}$ are independently present or adjacent groups thereof are linked to each other to form a substituted or unsubstituted aromatic ring or a substituted or unsubstituted heteroaromatic ring, and $R^{20}$ is a substituted or unsubstituted C6 to C18 aryl group, or a substituted or unsubstituted carbazolyl group.

10. The organic optoelectronic device of claim 9, wherein $R^{20}$ is a substituted or unsubstituted phenyl group, a substituted or unsubstituted biphenyl group, a substituted or unsubstituted naphthyl group, a substituted or unsubstituted terphenyl group, a substituted or unsubstituted anthracenyl group, a substituted or unsubstituted phenanthrenyl group, a substituted or unsubstituted triphenylene group, or a substituted or unsubstituted carbazolyl group.

11. The organic optoelectronic device of claim 9, wherein the first compound for the organic optoelectronic device is represented by Chemical Formula 1B-2 or Chemical Formula 1C-2:

[Chemical Formula 1B-2]

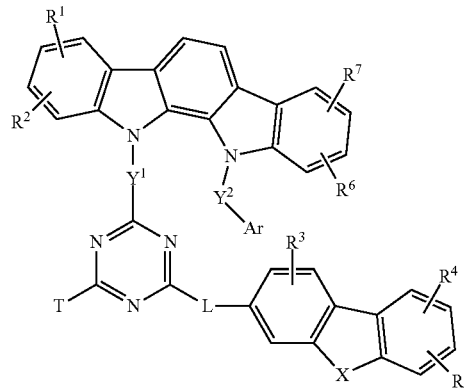

[Chemical Formula 1C-2]

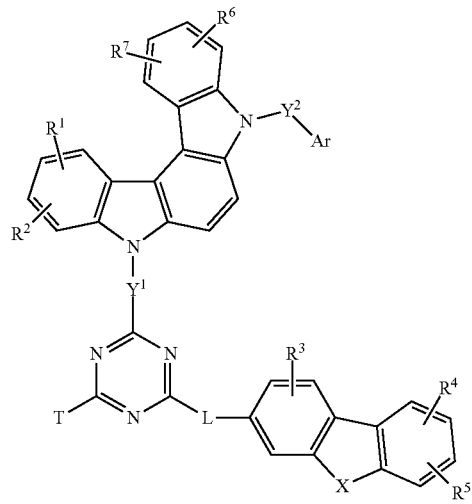

wherein, in Chemical Formula 1B-2 and Chemical Formula 1C-2,

X is O or S,

T is a substituted or unsubstituted phenyl group, a substituted or unsubstituted biphenyl group, a substituted or unsubstituted naphthyl group, a substituted or unsubstituted terphenyl group, a substituted or unsubstituted dibenzofuranyl group, or a substituted or unsubstituted dibenzothiophenyl group, Ar is a substituted or unsubstituted phenyl group, a substituted or unsubstituted biphenyl group, a substituted or unsubstituted naphthyl group, or a substituted or unsubstituted terphenyl group, L, $Y^1$, and $Y^2$ are independently a single bond, a substituted or unsubstituted phenylene group, or a substituted or unsubstituted biphenylene group, and $R^1$ to $R^7$ are independently hydrogen, a substituted or unsubstituted C1 to C5 alkyl group, or a substituted or unsubstituted phenyl group.

12. The organic optoelectronic device of claim 1, wherein the organic layer comprises a light emitting layer, and the composition for the organic optoelectronic device is included as a host of the light emitting layer.

13. A display device comprising the organic optoelectronic device of claim 1.

* * * * *